(12) United States Patent
Hatakeyama et al.

(10) Patent No.: US 9,063,413 B2
(45) Date of Patent: Jun. 23, 2015

(54) RESIST COMPOSITION, PATTERNING PROCESS, MONOMER, AND COPOLYMER

(71) Applicant: SHIN-ETSU CHEMICAL CO., LTD., Tokyo (JP)

(72) Inventors: Jun Hatakeyama, Joetsu (JP); Masayoshi Sagehashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 30 days.

(21) Appl. No.: 13/890,569

(22) Filed: May 9, 2013

(65) Prior Publication Data

US 2013/0309606 A1    Nov. 21, 2013

(30) Foreign Application Priority Data

May 16, 2012  (JP) ................................ 2012-112272

(51) Int. Cl.
| | |
|---|---|
| G03F 7/004 | (2006.01) |
| G03F 7/039 | (2006.01) |
| C08F 220/30 | (2006.01) |
| C07C 69/54 | (2006.01) |
| G03F 7/20 | (2006.01) |

(52) U.S. Cl.
CPC .............. *G03F 7/0041* (2013.01); *C07C 69/54* (2013.01); *G03F 7/20* (2013.01); *C08F 220/30* (2013.01); *G03F 7/0045* (2013.01); *G03F 7/0392* (2013.01)

(58) Field of Classification Search
CPC ....... G03F 7/004; G03F 7/039; G03F 7/0392; G03F 7/20; C08F 220/10; C08F 220/12; C08F 220/30; C08F 220/38
USPC ............ 526/318, 318.1, 319; 430/270.1, 326, 430/910, 921, 925
See application file for complete search history.

(56) References Cited

U.S. PATENT DOCUMENTS

| | | | |
|---|---|---|---|
| 5,879,851 | A | 3/1999 | Takahashi et al. |
| 6,448,420 | B1 | 9/2002 | Kinsho et al. |
| 7,482,108 | B2 | 1/2009 | Matsumaru et al. |
| 7,537,880 | B2 | 5/2009 | Harada et al. |
| 7,598,016 | B2 | 10/2009 | Kobayashi et al. |
| 7,858,289 | B2 | 12/2010 | Yamashita |
| 8,057,985 | B2 | 11/2011 | Ohashi et al. |
| 2008/0090170 | A1 | 4/2008 | Yoneda |
| 2010/0055608 | A1* | 3/2010 | Ohashi et al. ............. 430/270.1 |
| 2011/0318691 | A1* | 12/2011 | Tsuchimura et al. ...... 430/285.1 |
| 2012/0058429 | A1* | 3/2012 | Nishino et al. ........... 430/283.1 |
| 2012/0129103 | A1* | 5/2012 | Ohsawa et al. ........... 430/285.1 |
| 2012/0288795 | A1* | 11/2012 | Umezaki et al. .......... 430/271.1 |

FOREIGN PATENT DOCUMENTS

| | | | |
|---|---|---|---|
| JP | 2000-327633 A | | 11/2000 |
| JP | 3429592 B2 | | 7/2003 |
| JP | 2006-045311 A | | 2/2006 |
| JP | 2006-178317 A | | 7/2006 |
| JP | 2008-111103 A | | 5/2008 |
| JP | 2008-122932 A | | 5/2008 |
| JP | 2008-239918 A | | 10/2008 |
| JP | 2009-109595 A | | 5/2009 |
| JP | 2010-077404 A | | 4/2010 |
| JP | 2011-237477 | * | 11/2011 |
| WO | WO 2011-086757 | * | 7/2011 |

OTHER PUBLICATIONS

Machine translation of JP 2011-237477 published on Nov. 24, 2011.*
Y. Kishikawa et al., "Assessment of trade-off between resist resolution and sensitivity for optimization of hyper-NA immersion lithography", Proc. of SPIE, vol. 6520, pp. 65203L-1-65203L-9, (2007).
J. M. Hutchinson, "The Shot Noise Impact on Resist Roughness in EUV Lithography", Proc. of SPIE, vol. 3331, pp. 531-536, (1998).
R. L. Brainard et al., "Shot Noise, LER and Quantum Efficiency of EUV Photoresists", Proc. of SPIE, vol. 5374, pp. 74-85, (2004).
T. Kozawa et al., "Basic aspects of acid generation processes in chemically amplified resists for electron beam lithography", Proc. of SPIE, vol. 5753, pp. 361-367, (2005).
A. Nakano et al., "Deprotonation mechanism of poly(4-hydroxystyrene) and its derivative", Proc. of SPIE, vol. 5753, pp. 1034-1039, (2005).
M. Wang et al., "Novel Anionic Photoacid Generator (PAGs) and Photoresist for sub-50 nm patterning by EUVL and EBL", Proc. of SPIE, vol. 6519, pp. 65191F-1-65191F-6, (2007).

* cited by examiner

*Primary Examiner* — Anca Eoff
(74) *Attorney, Agent, or Firm* — Westerman, Hattori, Daniels & Adrian, LLP

(57) ABSTRACT

A polymer is obtained from copolymerization of a recurring unit having a carboxyl and/or phenolic hydroxyl group substituted with an acid labile group and a recurring unit having formula (1) wherein $R^1$ is methyl, ethyl, propyl, methoxy, ethoxy or propoxy, $R^2$ is H or $CH_3$, and m is 1 to 4. The polymer is used as a base resin to formulate a resist composition, which is improved in contrast of alkali dissolution rate before and after exposure, acid diffusion control, resolution, and profile and edge roughness of a pattern after exposure.

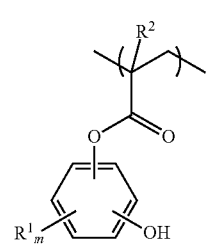

(1)

8 Claims, No Drawings

RESIST COMPOSITION, PATTERNING PROCESS, MONOMER, AND COPOLYMER

CROSS-REFERENCE TO RELATED APPLICATION

This non-provisional application claims priority under 35 U.S.C. §119(a) on Patent Application No. 2012-112272 filed in Japan on May 16, 2012, the entire contents of which are hereby incorporated by reference.

TECHNICAL FIELD

This invention relates to a resist composition, and more particularly to a chemically amplified positive resist composition; and a patterning process using the same. It also relates to a monomer and a polymer for use in the resist composition as base resin.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, extreme ultraviolet (EUV) lithography of wavelength 13.5 nm, and double patterning version of the ArF lithography, on which active research efforts have been made.

With respect to high-energy radiation of very short wavelength such as electron beam (EB) or x-ray, hydrocarbons and similar light elements used in resist materials have little absorption. Then polyhydroxystyrene base resist materials are under consideration.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the accelerating voltage increases, a lowering of sensitivity of resist film becomes of concern. As the accelerating voltage increases, the influence of forward scattering in a resist film becomes so reduced that the contrast of electron image writing energy is improved to ameliorate resolution and dimensional control whereas electrons can pass straightforward through the resist film so that the resist film becomes less sensitive. Since the mask exposure tool is designed for exposure by direct continuous writing, a lowering of sensitivity of resist film leads to an undesirably reduced throughput. Due to a need for higher sensitivity, chemically amplified resist compositions are contemplated.

As the feature size reduces, image blurs due to acid diffusion become a problem. To insure resolution for fine patterns with a size of 45 nm et seq., not only an improvement in dissolution contrast is important as previously reported, but control of acid diffusion is also important as reported in SPIE Vol. 6520 65203L-1 (2007). Since chemically amplified resist compositions are designed such that sensitivity and contrast are enhanced by acid diffusion, an attempt to minimize acid diffusion by reducing the temperature and/or time of post-exposure baking (PEB) fails, resulting in drastic reductions of sensitivity and contrast.

A triangular tradeoff relationship among sensitivity, resolution, and edge roughness has been pointed out. Specifically, a resolution improvement requires to suppress acid diffusion whereas a short acid diffusion distance leads to a loss of sensitivity.

The addition of an acid generator capable of generating a bulky acid is an effective means for suppressing acid diffusion. It was then proposed to incorporate in a polymer an acid generator of an onium salt having a polymerizable olefin. JP-A 2006-045311 discloses a sulfonium salt having polymerizable olefin capable of generating a specific sulfonic acid and a similar iodonium salt. JP-A 2006-178317 discloses a sulfonium salt having sulfonic acid directly attached to the main chain.

A tradeoff relationship between sensitivity and edge roughness has been pointed out. For example, SPIE Vol. 3331 p 531 (1998) describes that sensitivity is in inverse proportion to edge roughness. It is expected that the edge roughness of a resist film is reduced by increasing the exposure dose to reduce shot noise. SPIE Vol. 5374 p 74 (2004) describes a tradeoff between sensitivity and roughness in the EUV lithography in that a resist material containing a more amount of quencher is effective in reducing roughness, but suffers from a decline of sensitivity at the same time. There is a need to enhance the quantum efficiency of acid generation in order to overcome the problem.

With respect to the acid generating mechanism triggered by EB exposure, SPIE Vol. 5753 p 361 (2005) reports that PAG releases acid through the mechanism that a polymer is excited by exposure so that electrons migrate to the PAG. Since the irradiation energy of EB or EUV is higher than the threshold value (10 eV) of ionization potential energy of a base polymer, it is presumed that the base polymer is readily ionized. An exemplary material of accelerating electron migration is hydroxystyrene.

It is reported in SPIE Vol. 5753 p 1034 (2005) that poly-4-hydroxystyrene has a higher acid generation efficiency in EB exposure than poly-4-methoxystyrene, indicating that poly-4-hydroxystyrene provides for efficient migration of electrons to PAG upon EB exposure.

Reported in SPIE Vol. 6519 p 65191F-1 (2007) is a material obtained through copolymerization of hydroxystyrene for increasing the acid generation efficiency by electron migration, a methacrylate of PAG having sulfonic acid directly bonded to a polymer backbone for suppressing acid diffusion, and a methacrylate having an acid labile group. Since hydroxystyrene has a phenolic hydroxyl group which is weakly acidic, it is effective for reducing swell in alkaline developer, but causes to increase acid diffusion. On the other hand, a methacrylate having lactone as the adhesive group is widely employed in the ArF resist composition. Since this methacrylate has high hydrophilicity and no alkali solubility, it is ineffective for reducing swell, but effective for suppressing acid diffusion. A combination of hydroxystyrene and lactone-containing methacrylate as the adhesive group can establish a fairly good balance among sensitivity improvement, swell reduction, and acid diffusion control, but is still insufficient.

Copolymerization of hydroxyphenyl methacrylate with lactone-containing methacrylate and further methacrylate of PAG having sulfonic acid directly bonded to the polymer backbone makes it possible to form a resist having high sensitivity and high resolution while controlling acid diffusion. See JP-A 2010-077404. In this case, it is effective for further enhanced sensitivity to increase the proportion of hydroxyphenyl methacrylate. However, increasing the proportion of hydroxyphenyl methacrylate makes the polymer more alkaline soluble, resulting in a film thickness loss and hence, pattern collapse. It would be desirable to have a resist having higher sensitivity and resolution.

CITATION LIST

Patent Document 1: JP-A 2006-045311 (U.S. Pat. No. 7,482,108)
Patent Document 2: JP-A 2006-178317
Patent Document 3: JP-A 2010-077404
Non-Patent Document 1: SPIE Vol. 6520 65203L-1 (2007)
Non-Patent Document 2: SPIE Vol. 3331 p 531 (1998)
Non-Patent Document 3: SPIE Vol. 5374 p 74 (2004)
Non-Patent Document 4: SPIE Vol. 5753 p 361 (2005)
Non-Patent Document 5: SPIE Vol. 5753 p 1034 (2005)
Non-Patent Document 6: SPIE Vol. 6519 p 65191F-1 (2007)

SUMMARY OF INVENTION

An object of the present invention is to provide a resist composition comprising a specific polymer, typically chemically amplified positive resist composition comprising a specific polymer, which composition exhibits a higher resolution than the prior art positive resist compositions and minimal edge roughness (LER, LWR), and forms a pattern of good profile after exposure; a patterning process using the resist composition; a polymerizable monomer; and a polymer thereof for use in the resist composition as a base resin.

Making extensive investigations in search for a resist material capable of meeting the current requirements including high sensitivity, high resolution, and minimal edge roughness, the inventors have found that a polymer comprising recurring units derived from hydroxyphenyl methacrylate substituted with an alkyl or alkoxy group is quite effective as a base resin in a resist composition, typically chemically amplified positive resist composition.

The inventors have found that a polymer obtained from copolymerization of a recurring unit having a carboxyl group substituted with an acid labile group for suppressing acid diffusion and improving dissolution contrast with a hydroxyphenyl methacrylate substituted with an alkyl or alkoxy group as represented by the general formula (1) below is useful as a base resin in a resist composition, typically chemically amplified positive resist composition, that a resist composition comprising the polymer is improved in such properties as a contrast of alkali dissolution rate before and after exposure, acid diffusion suppressing effect, resolution, and profile and edge roughness of a pattern after exposure, and thus best suited as a micropatterning material for the fabrication of VLSI and photomasks.

A phenolic group is effective for sensitization with respect to EB and EUV and for preventing swell in alkaline aqueous developer. Since the inventive polymer contains a phenolic group and an alkyl or alkoxy group within a common molecule, it has a sensitizing effect and its alkaline dissolution rate is low enough to suppress a pattern film thickness loss after alkaline development. Since the pattern film thickness loss is suppressed, the phenolic group having an alkyl or alkoxy group can be incorporated in a higher proportion than the phenolic group free of alkyl or alkoxy group. This enables to increase sensitivity.

The resist composition has a satisfactory effect of suppressing acid diffusion and a high resolution, lends itself to the lithography process, and forms a pattern of good profile and minimal edge roughness after exposure. Because of these advantages, the composition is readily implemented in practice and best suited as a VLSI-forming resist material and mask pattern forming material.

In one aspect, the invention provides a resist composition comprising as a base resin a polymer comprising recurring units having a carboxyl and/or phenolic hydroxyl group whose hydrogen is substituted by an acid labile group, and recurring units having the general formula (1), the polymer having a weight average molecular weight of 1,000 to 500,000.

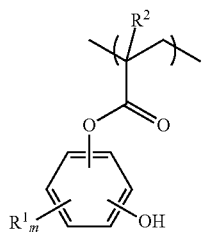

(1)

Herein $R^1$ is methyl, ethyl, propyl, methoxy, ethoxy or propoxy, $R^2$ is hydrogen or methyl, and m is an integer of 1 to 4.

In a preferred embodiment, the polymer comprises recurring units (a) and acid labile group-substituted recurring units (b1) and/or (b2) copolymerized together, as represented by the general formula (2).

(2)

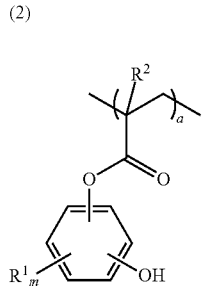

(a)

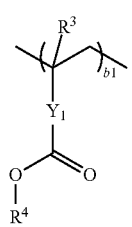

(b1)

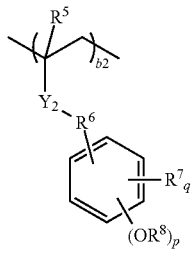
(b2)

Herein $R^1$, $R^2$ and m are as defined above, $R^3$ and $R^5$ each are hydrogen or methyl, $R^4$ and $R^8$ each are an acid labile group, $R^6$ is a single bond or a straight or branched $C_1$-$C_6$ alkylene group, $R^7$ is hydrogen, fluorine, trifluoromethyl, cyano, or straight, branched or cyclic $C_1$-$C_6$ alkyl group, p is 1 or 2, q is an integer of 0 to 4, $Y_1$ is a single bond, a divalent $C_1$-$C_{12}$ linking group having an ester radical, ether radical or lactone ring, phenylene group or naphthylene group, $Y_2$ is a single bond, —C(=O)—O— or —C(=O)—NH—, a, b1 and b2 are numbers in the range: $0<a<1.0$, $0 \le b1<1.0$, $0 \le b2<1.0$, $0<b1+b2<1.0$, and $0.1 \le a+b1+b2 \le 1.0$.

In addition to the recurring units (a) and acid labile group-substituted recurring units (b1) and/or (b2), as represented by the general formula (2), the polymer preferably further comprises recurring units (c) having an adhesive group selected from the class consisting of hydroxyl (exclusive of hydroxyl in formula (1)), carboxyl, lactone ring, carbonate, thiocarbonate, carbonyl, cyclic acetal, ether, ester, sulfonic acid ester, cyano, amide, and —O—C(=O)-G- wherein G is sulfur or NH and c is a number in the range: $0<c \le 0.9$ and $0.2 \le a+b1+b2+c \le 1.0$.

In addition to the recurring units (a), (b1), (b2) and (c), the polymer may further comprise recurring units (d) of at least one type selected from sulfonium salt units (d1) to (d3) represented by the general formula (3).

(3)
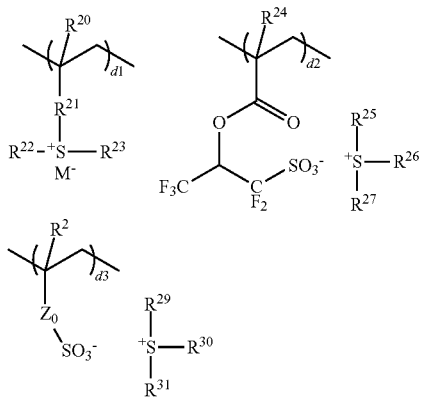

Herein $R^{20}$, $R^{24}$, and $R^{28}$ each are hydrogen or methyl, $R^{21}$ is a single bond, phenylene, —O—R—, or —C(=O)—$Y_0$—R—, $Y_0$ is oxygen or NH, R is a straight, branched or cyclic $C_1$-$C_6$ alkylene group, alkenylene or phenylene group, which may contain a carbonyl, ester, ether or hydroxyl radical, $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether radical, or a $C_6$-$C_{12}$ aryl, $C_7$-$C_{20}$ aralkyl, or thiophenyl group, $Z_0$ is a single bond, methylene, ethylene, phenylene, fluorophenylene, —O—$R^{32}$—, or —C(=O)—$Z_1$—$R^{32}$—, $Z_1$ is oxygen or NH, $R^{32}$ is a straight, branched or cyclic $C_1$-$C_6$ alkylene group, alkenylene or phenylene group, which may contain a carbonyl, ester, ether or hydroxyl radical, $M^-$ is a non-nucleophilic counter ion, d1, d2 and d3 are in the range: $0 \le d1 \le 0.5$, $0 \le d2 \le 0.5$, $0 \le d3 \le 0.5$, $0<d1+d2+d3 \le 0.5$, and $0.2 \le a+b1+b2+c<1.0$.

In a preferred embodiment, the resist composition further comprises an organic solvent and an acid generator, the composition being a chemically amplified resist composition. The resist composition may further comprise a basic compound and/or a surfactant as an additive.

In another aspect, the invention provides a polymerizable monomer having any one of the general formulae Ma1 to Ma8.

Ma1
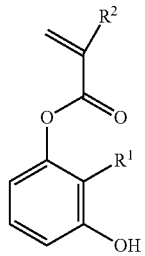

Ma2
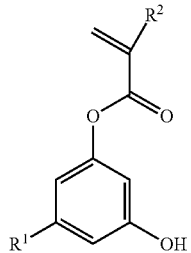

Ma3
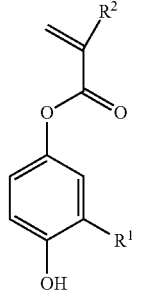

Ma4
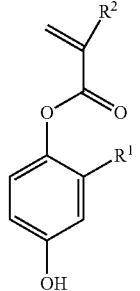

Ma5
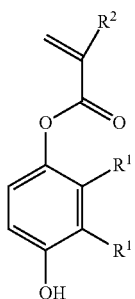
Ma6
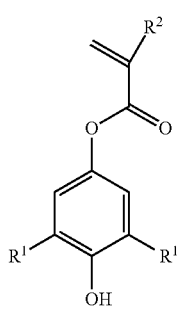
Ma7
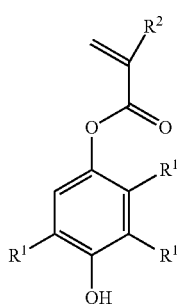
Ma8
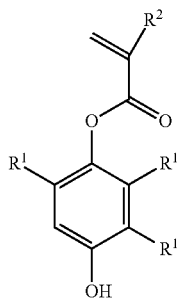
Herein R¹ is methyl, ethyl, propyl, methoxy, ethoxy or propoxy, and R² is hydrogen or methyl.
In a further aspect, the invention provides a polymer comprising recurring units (a') of at least one type selected from units (a1) to (a8) and acid labile group-containing recurring units (b1) and/or (b2) as copolymerized and having a weight average molecular weight of 1,000 to 500,000.
(a1)
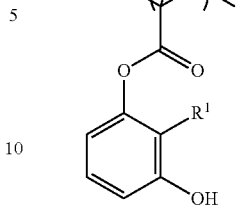
(a2)
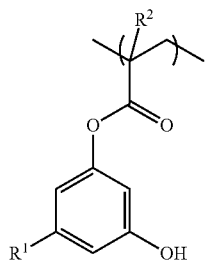
(a3)
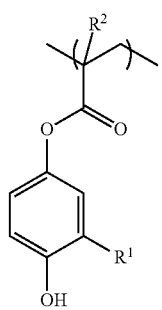
(a4)
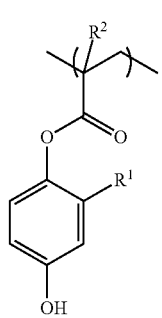
(a5)
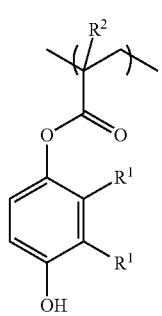

-continued

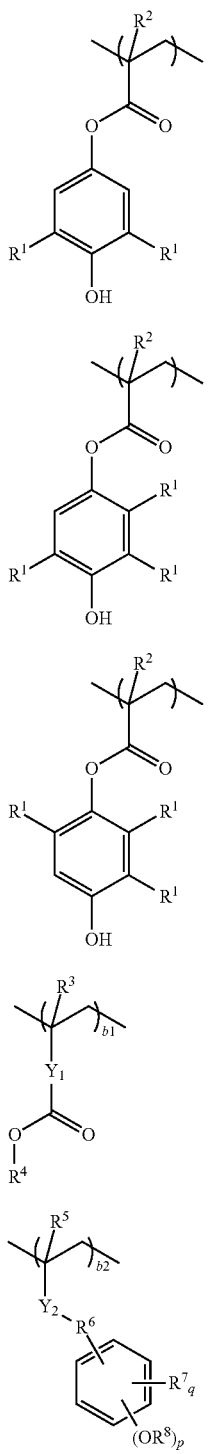

(a6)

(a7)

(a8)

(b1)

(b2)

Herein $R^1$ is methyl, ethyl, propyl, methoxy, ethoxy or propoxy, $R^2$ is hydrogen or methyl, $R^3$ and $R^5$ each are hydrogen or methyl, $R^4$ and $R^8$ each are an acid labile group, $R^6$ is a single bond or a straight or branched $C_1$-$C_6$ alkylene group, $R^7$ is hydrogen, fluorine, trifluoromethyl, cyano, or straight, branched or cyclic $C_1$-$C_6$ alkyl group, p is 1 or 2, q is an integer of 0 to 4, $Y_1$ is a single bond, a divalent $C_1$-$C_{12}$ linking group having an ester radical, ether radical or lactone ring, phenylene group or naphthylene group, $Y_2$ is a single bond,
—C(=O)—O— or —C(=O)—NH—, a', b1 and b2 are numbers in the range: 0<a'<1.0, 0≤b1<1.0, 0≤b2<1.0, 0<b1+b2<1.0, and 0.1≤a'+b1+b2≤1.0.

In a still further aspect, the invention provides a pattern forming process comprising the steps of applying the resist composition defined above onto a substrate to form a coating, baking, exposing the coating to high-energy radiation, and developing the exposed coating in a developer. Typically, the high-energy radiation is KrF excimer laser, ArF excimer laser, electron beam or soft X-ray having a wavelength of 3 to 15 nm.

The resist composition, typically chemically amplified positive resist composition, is used not only in the lithography for forming semiconductor circuits, but also in the formation of mask circuit patterns, micromachines, and thin-film magnetic head circuits.

Advantageous Effects of Invention

The resist composition has a satisfactory effect of suppressing acid diffusion and a high resolution, and forms a pattern of good profile and minimal edge roughness after exposure. The resist composition, typically chemically amplified positive resist composition is best suited as a micropatterning material by KrF excimer laser, ArF excimer laser, EB and EUV lithography processes for the microfabrication of VLSI and photomasks.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The acronym "PAG" stands for photoacid generator, "PEB" for post-exposure bake, "LER" for line edge roughness, and "LWR" for line width roughness.

One embodiment of the invention is a resist composition, typically positive resist composition comprising a polymer comprising recurring units having a carboxyl and/or phenolic hydroxyl group whose hydrogen is substituted by an acid labile group, and recurring units having the general formula (1) as a base resin.

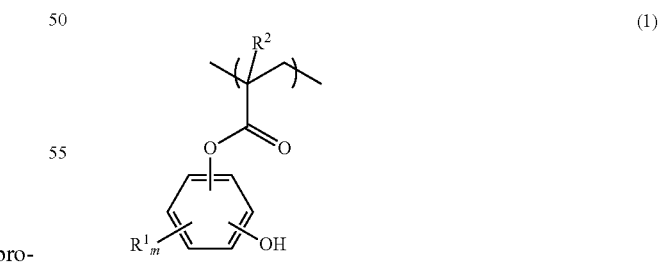

(1)

Herein $R^1$ is methyl, ethyl, propyl, methoxy, ethoxy or propoxy, $R^2$ is hydrogen or methyl, and m is an integer of 1 to 4.

The unit having formula (1) is preferably derived from (meth)acrylic acid having a carboxyl group whose hydrogen atom is substituted.

In a preferred embodiment, the polymer as the base resin is a copolymer comprising at least recurring units (a) and acid labile group-substituted recurring units (b1) and/or (b2), as represented by the general formula (2). The copolymer has a weight average molecular weight of 1,000 to 500,000.

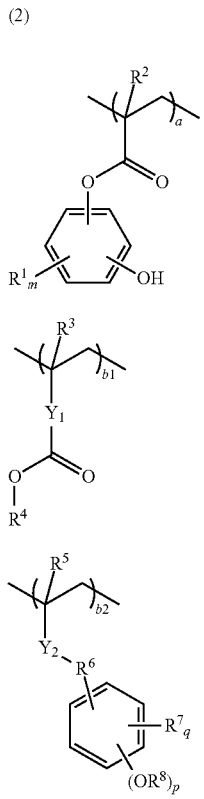

(2)

Herein $R^1$, $R^2$ and m are as defined above, $R^3$ and $R^5$ each are hydrogen or methyl, $R^4$ and $R^8$ each are an acid labile group, $R^6$ is a single bond or a straight or branched $C_1$-$C_6$ alkylene group, $R^7$ is hydrogen, fluorine, trifluoromethyl, cyano, or straight, branched or cyclic $C_1$-$C_6$ alkyl group, p is 1 or 2, q is an integer of 0 to 4, $Y_1$ is a single bond, a divalent $C_1$-$C_{12}$ linking group having an ester radical, ether radical or lactone ring, phenylene group or naphthylene group, $Y_2$ is a single bond, —C(=O)—O— or —C(=O)—NH—. The subscripts a, b1 and b2 are numbers in the range: 0<a<1.0, 0≤b1<1.0, 0≤b2<1.0, 0<b1+b2<1.0, and 0.1≤a+b1+b2≤1.0.

A monomer Ma from which the recurring unit (a) of formula (1) is derived may be illustrated by the following formula.

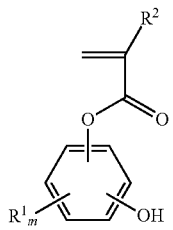

Ma

Herein $R^1$, $R^2$ and m are as defined above.

This monomer may be synthesized by converting one hydroxyl group of alkylated or alkoxylated hydroquinone, resorcinol or catechol to a methacrylate ester.

Examples of the monomer Ma from which the unit (a) is derived are given below, but not limited thereto.

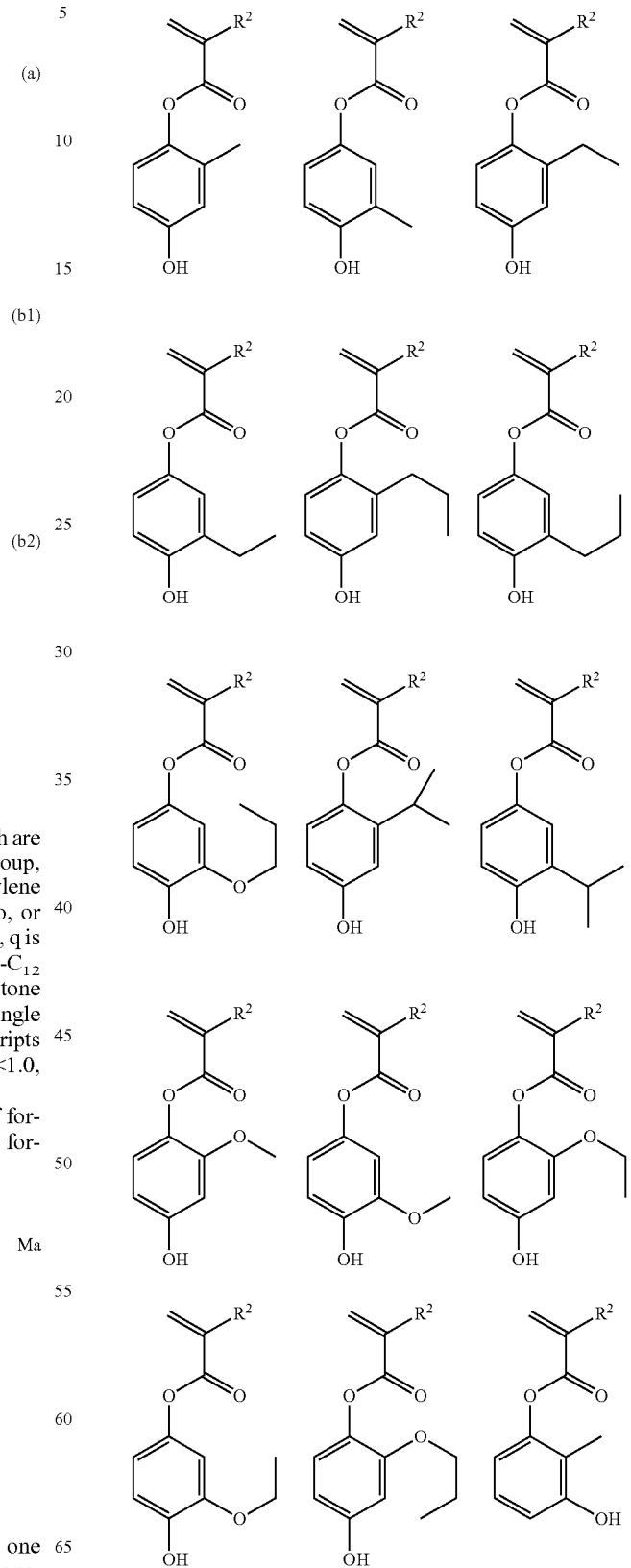

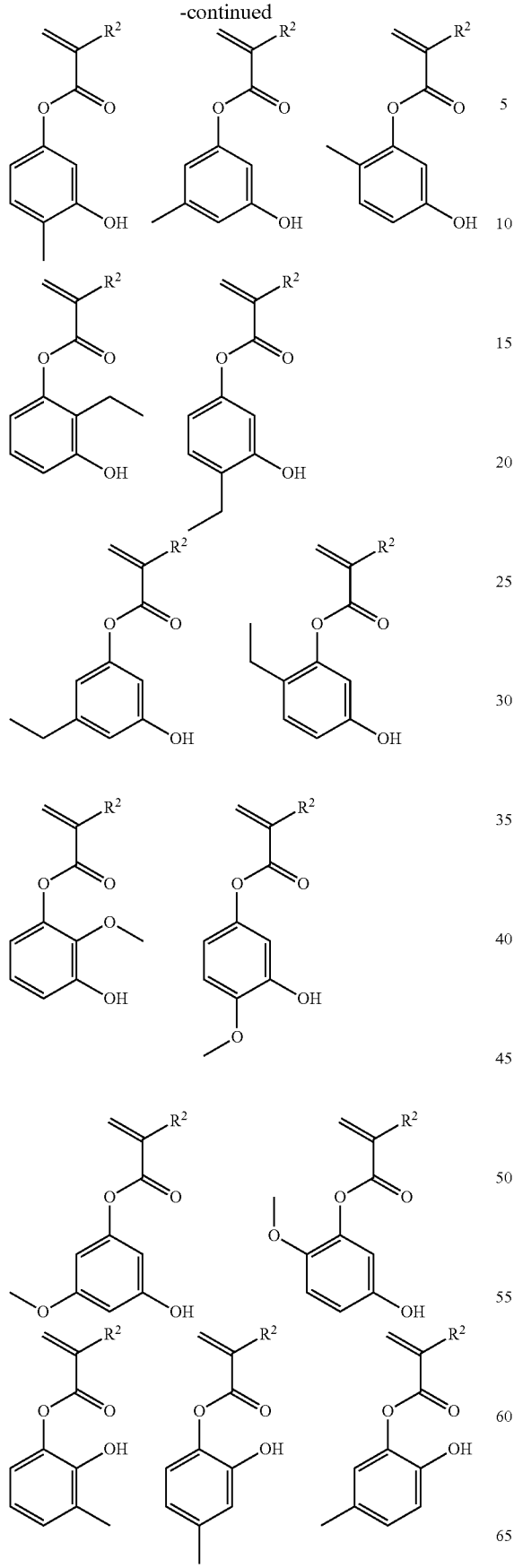

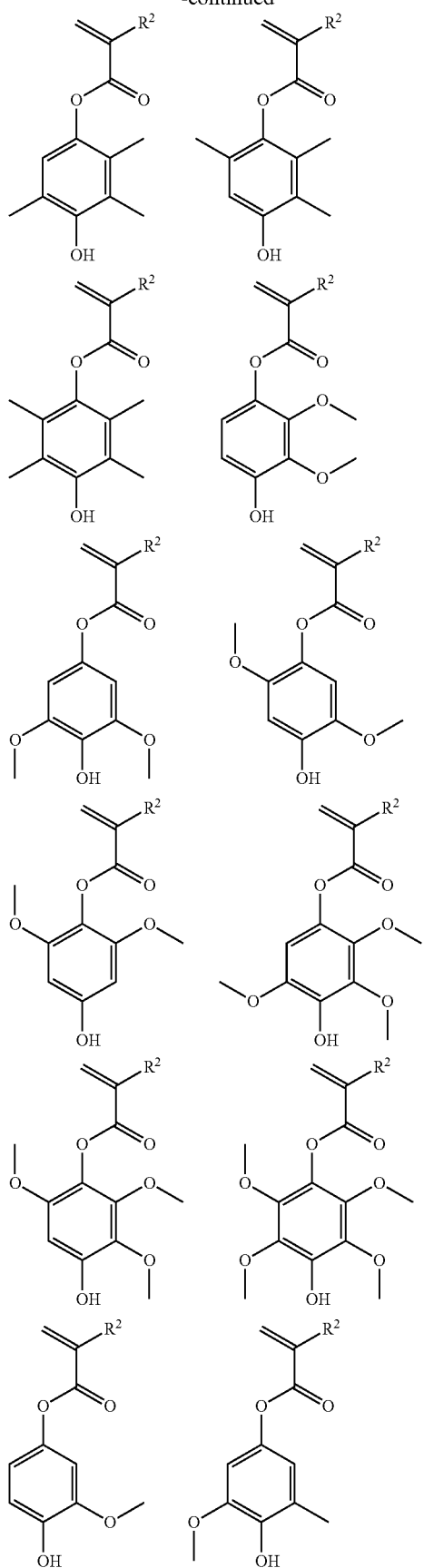
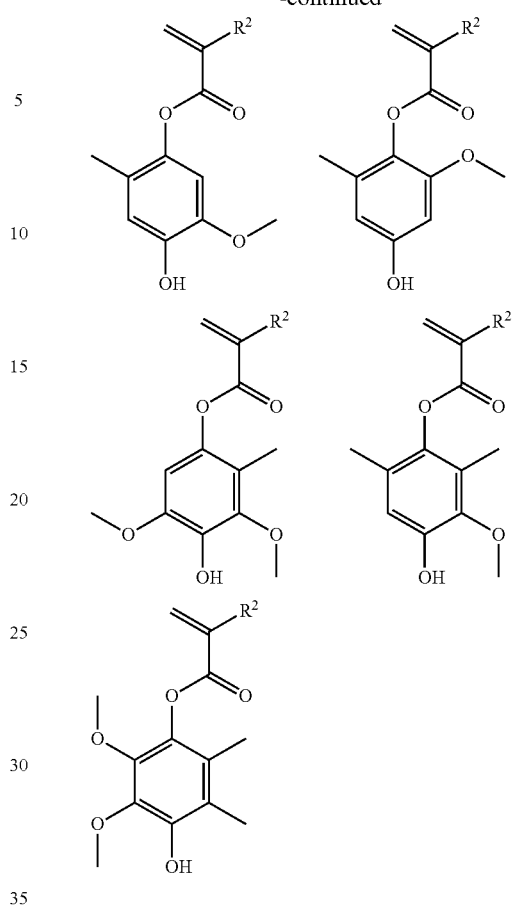
Herein R² is as defined above.
Most preferred of these monomers are monomers Ma1 to Ma8, as represented by the general formula.
Ma1
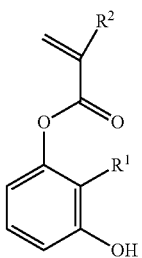
Ma2
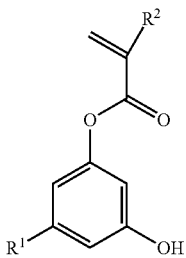

-continued

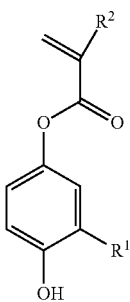
Ma3

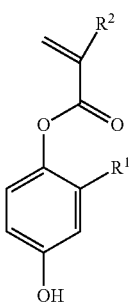
Ma4

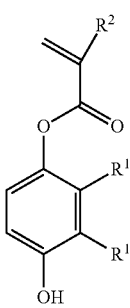
Ma5

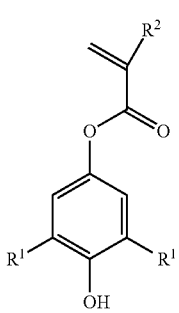
Ma6

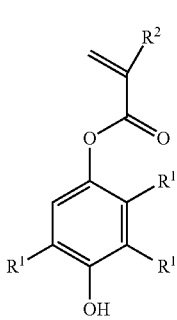
Ma7

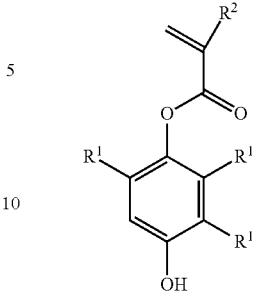
Ma8

Herein $R^1$ is methyl, ethyl, propyl, methoxy, ethoxy or propoxy, and $R^2$ is hydrogen or methyl.

While the polymer is used in the resist composition, the recurring unit (a) is methacrylate containing both an alkyl or alkoxy group and a phenolic hydroxyl group, each one, in a common molecule. Since this methacrylate unit offers a lower alkaline dissolution rate than hydroxyphenyl methacrylate free of alkyl or alkoxy group, it is effective for reducing a pattern film thickness loss after development and suppressing pattern collapse. Due to the electron donating effect of alkyl or alkoxy group, the electron density of benzene ring is increased. This increases the efficiency of secondary electron generation upon EUV or EB exposure, exerting a better sensitizing effect which leads to a further improvement in sensitivity. Most preferably, one alkyl or alkoxy group is introduced per phenyl group. While many examples of methyl or methoxy-substituted hydroxystyrene are known from JP-A 2009-109595, paragraph [0208], hydroxystyrene copolymers have a less sensitizing effect than hydroxyphenyl methacrylate copolymers. Copolymerization of hydroxyphenyl methacrylate substituted with an alkyl or alkoxy group ensures advantages including a high sensitivity, a reduced film thickness loss after alkaline development, and prevention of pattern collapse due to swell during development.

Monomers Mb1 and Mb2 from which the acid labile group-containing recurring units (b1) and (b2) in formula (2) are derived may be illustrated by the following formulae.

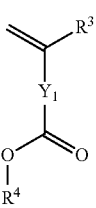
Mb1

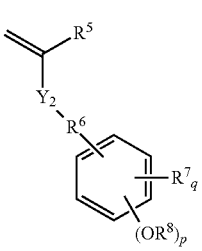
Mb2

Herein $R^3$ to $R^8$, $Y_1$, $Y_2$, p and q are as defined above.

Of the groups represented by $Y_1$, the $C_1$-$C_{12}$ linking group having a lactone ring may be exemplified by the following.

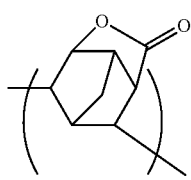
Examples of the monomer Mb1 from which recurring unit (b1) is derived are given below, but not limited thereto.
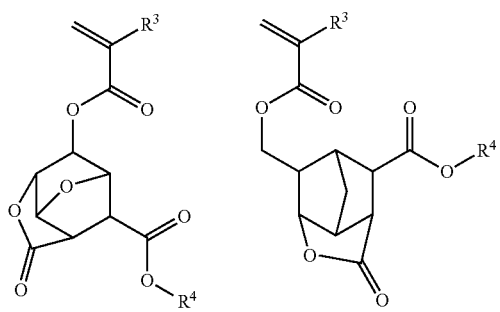
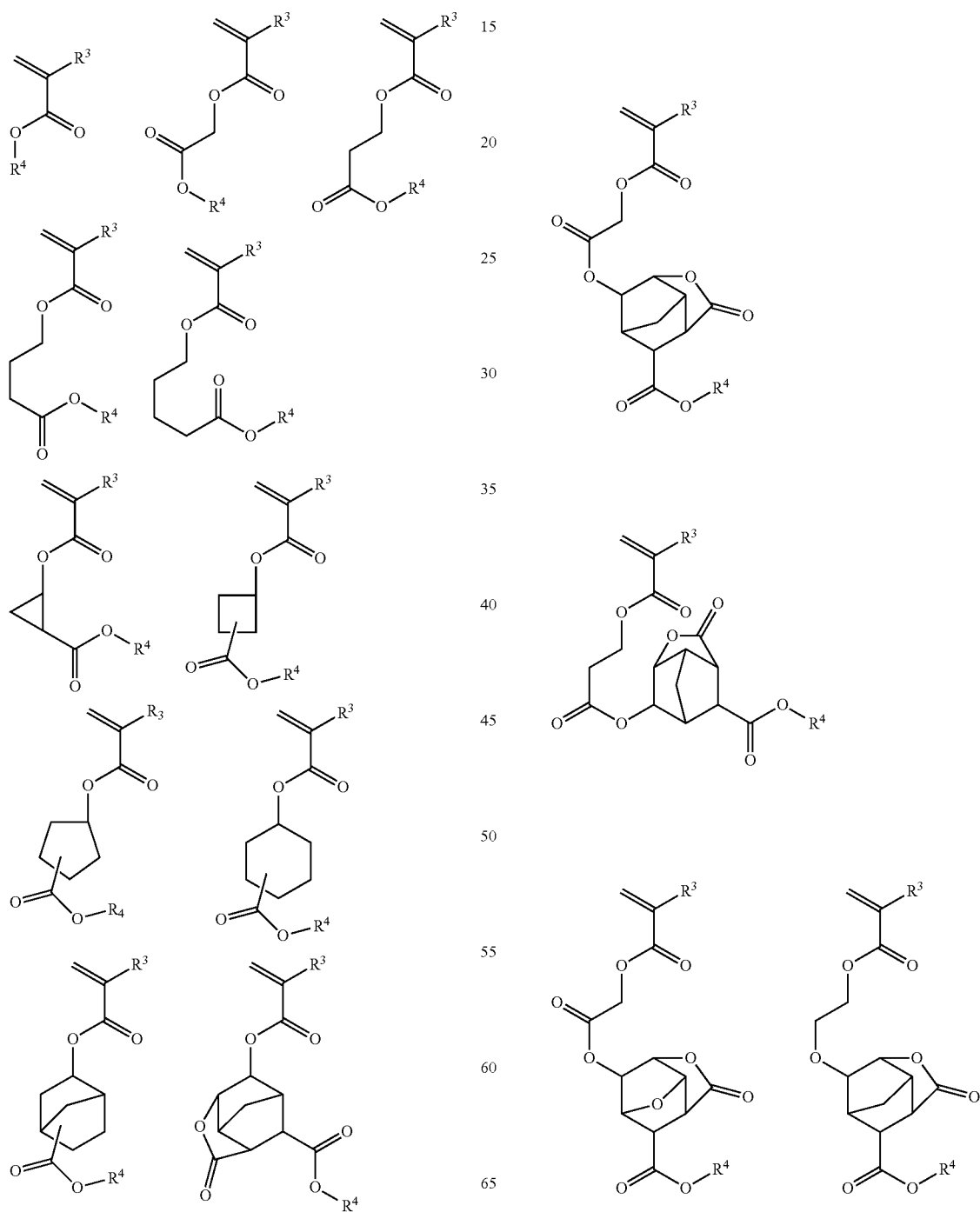

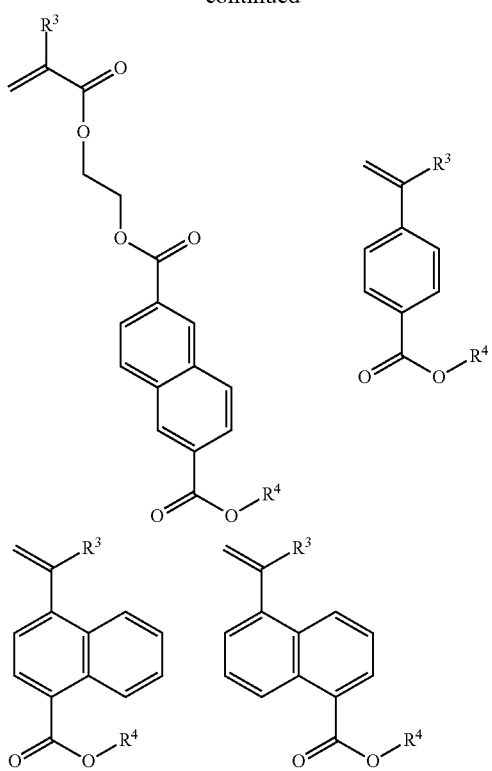
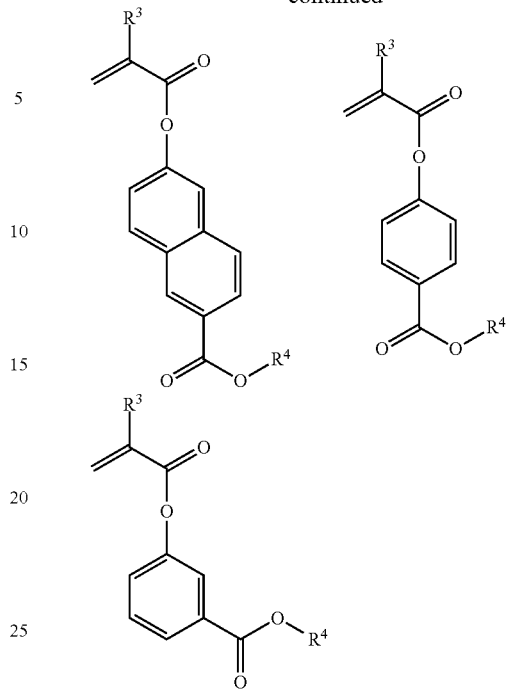
Herein $R^3$ and $R^4$ are as defined above.
Examples of the monomer Mb2 from which recurring unit (b2) is derived are given below, but not limited thereto.
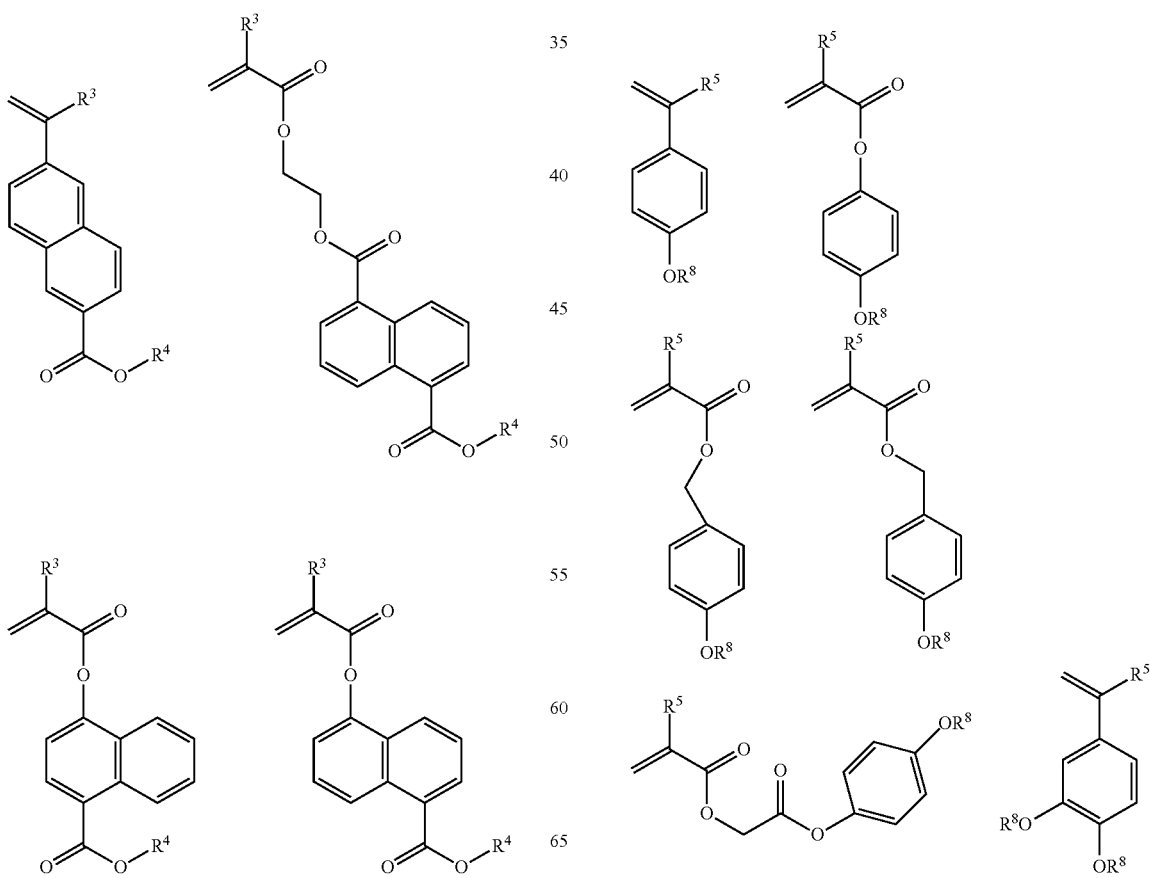

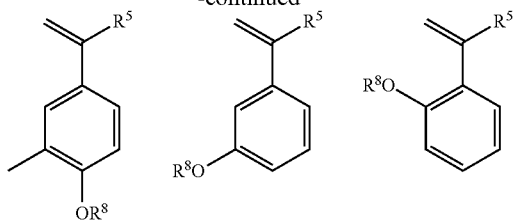
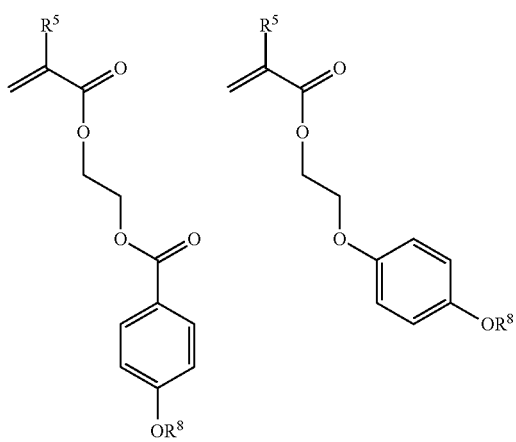
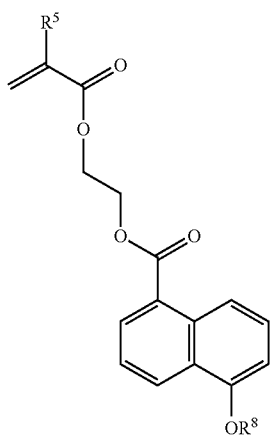
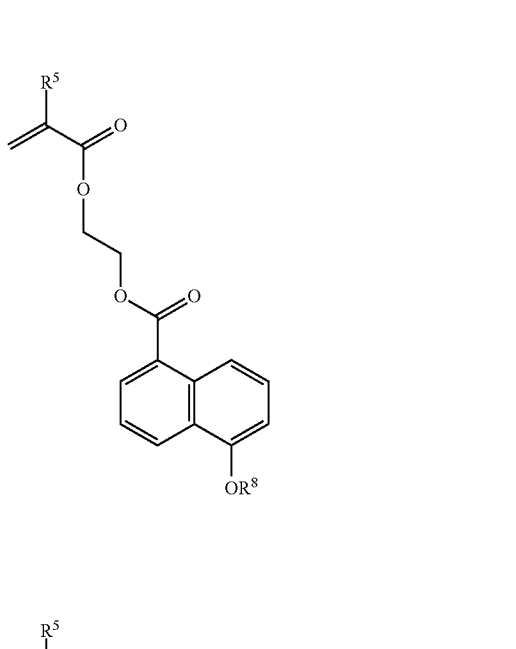
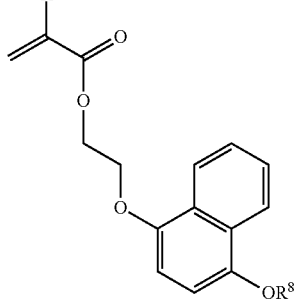
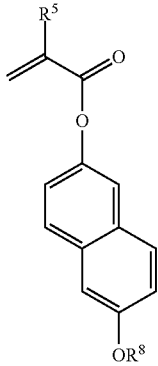
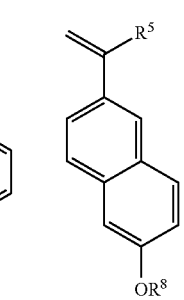
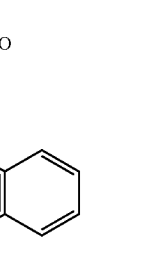
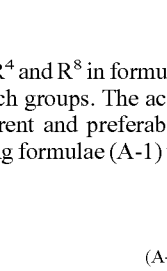
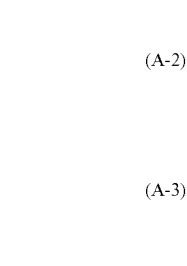

Herein $R^5$ and $R^8$ are as defined above.

The acid labile groups represented by $R^4$ and $R^8$ in formula (2) may be selected from a variety of such groups. The acid labile groups may be the same or different and preferably include substituent groups of the following formulae (A-1) to (A-3).

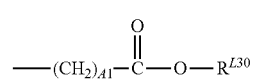

(A-1)

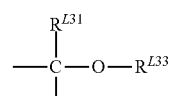

(A-2)

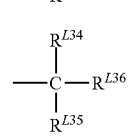

(A-3)

In formula (A-1), $R^{L30}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (A-3). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter A1 is an integer of 0 to 6.

In formula (A-2), $R^{L31}$ and $R^{L32}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L33}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

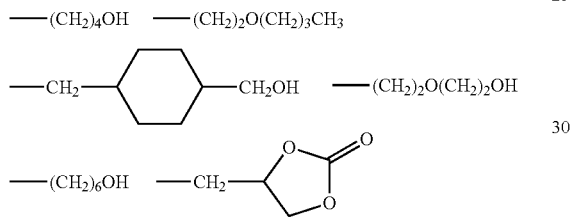

A pair of $R^{L31}$ and $R^{L32}$, $R^{L31}$ and $R^{L33}$, or $R^{L32}$ and $R^{L33}$ may bond together to form a ring with the carbon and oxygen atoms to which they are attached. Each of $R^{L31}$, $R^{L32}$ and $R^{L33}$ is a straight or branched alkylene group of 1 to 18 carbon atoms, preferably 1 to 10 carbon atoms when they form a ring, while the ring preferably has 3 to 10 carbon atoms, more preferably 4 to 10 carbon atoms.

Examples of the acid labile groups of formula (A-1) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Also included are substituent groups having the formulae (A-1)-1 to (A-1)-10.

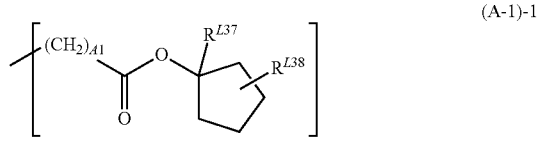
(A-1)-1

(A-1)-2

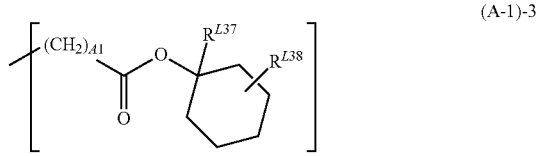
(A-1)-3

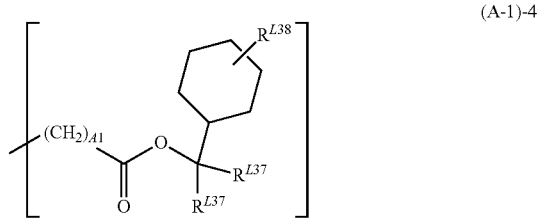
(A-1)-4

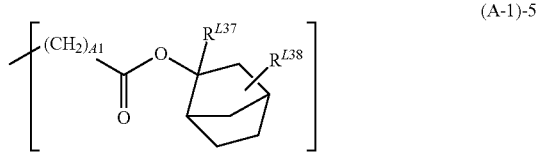
(A-1)-5

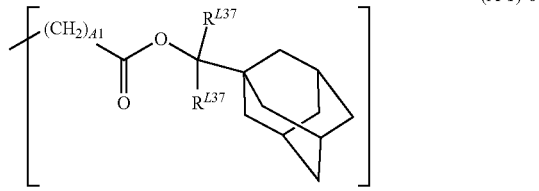
(A-1)-6

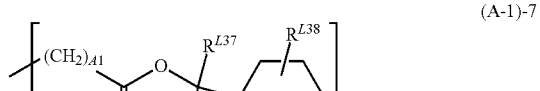
(A-1)-7

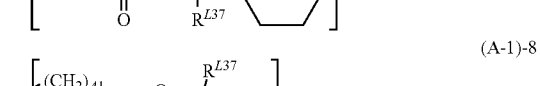
(A-1)-8

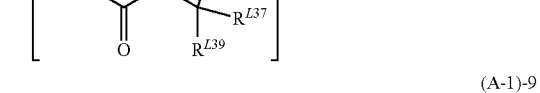
(A-1)-9

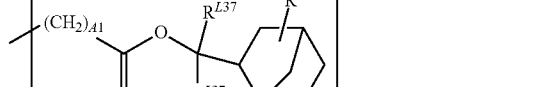
(A-1)-10

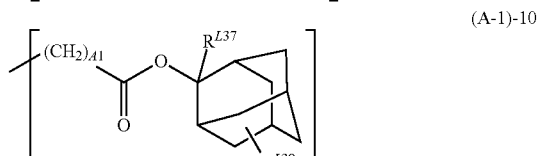

Herein $R^{L37}$ is each independently a straight, branched or cyclic $C_1$-$C_{10}$ alkyl group or $C_6$-$C_{20}$ aryl group, $R^{L38}$ is hydrogen or a straight, branched or cyclic $C_1$-$C_{10}$ alkyl group, $R^{L39}$ is each independently a straight, branched or cyclic $C_2$-$C_{10}$ alkyl group or $C_6$-$C_{20}$ aryl group, and A1 is as defined above.

Of the acid labile groups of formula (A-2), the straight and branched ones are exemplified by the following groups having formulae (A-2)-1 to (A-2)-69.

(A-2)-1

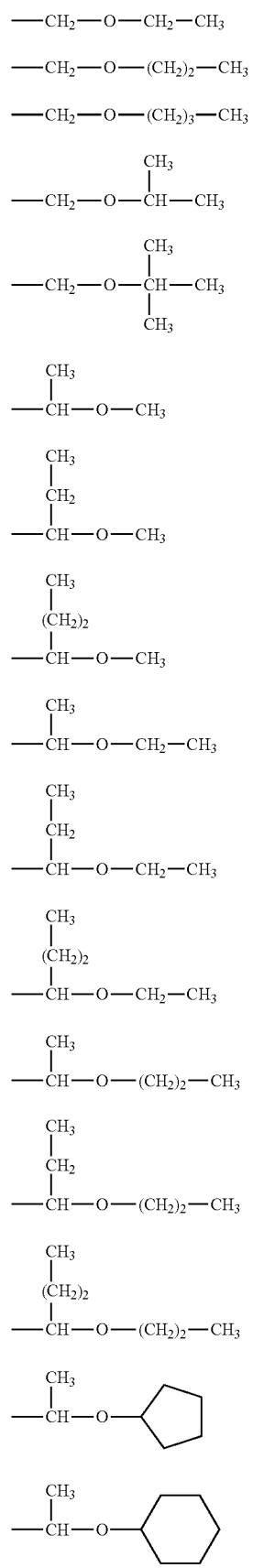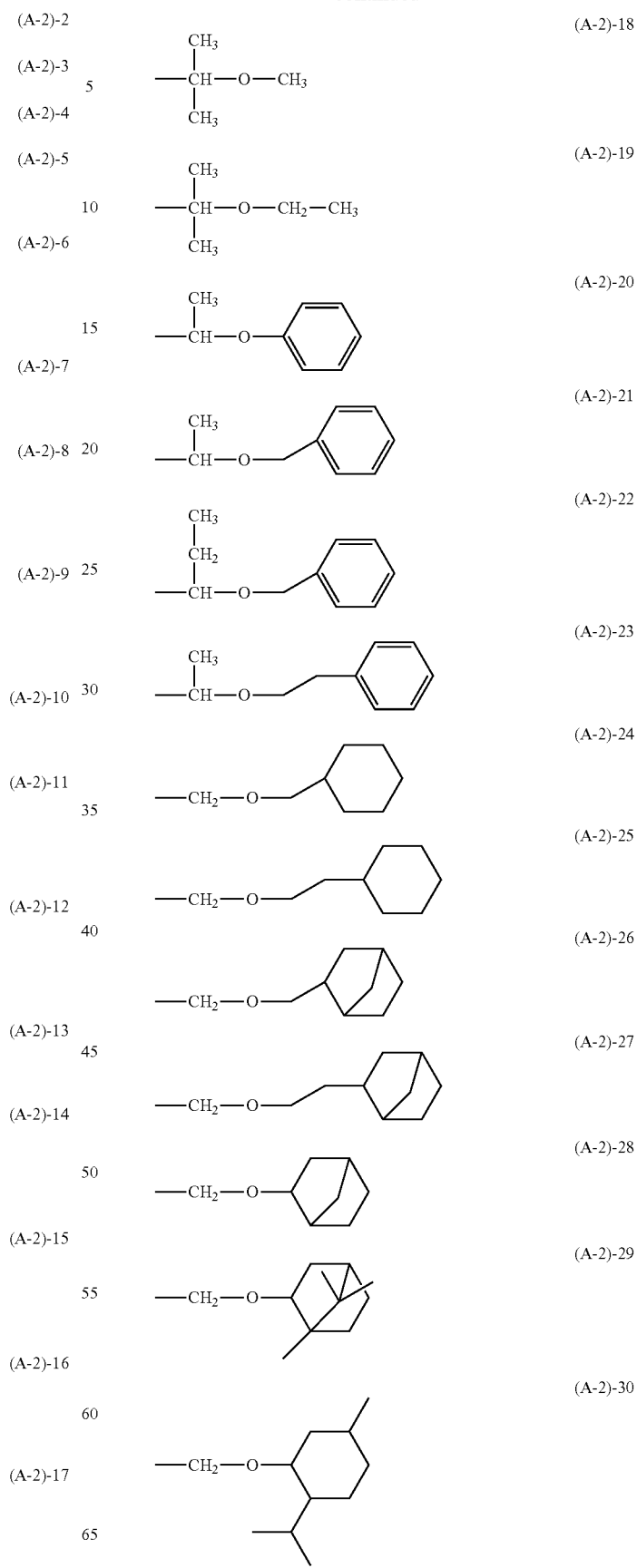

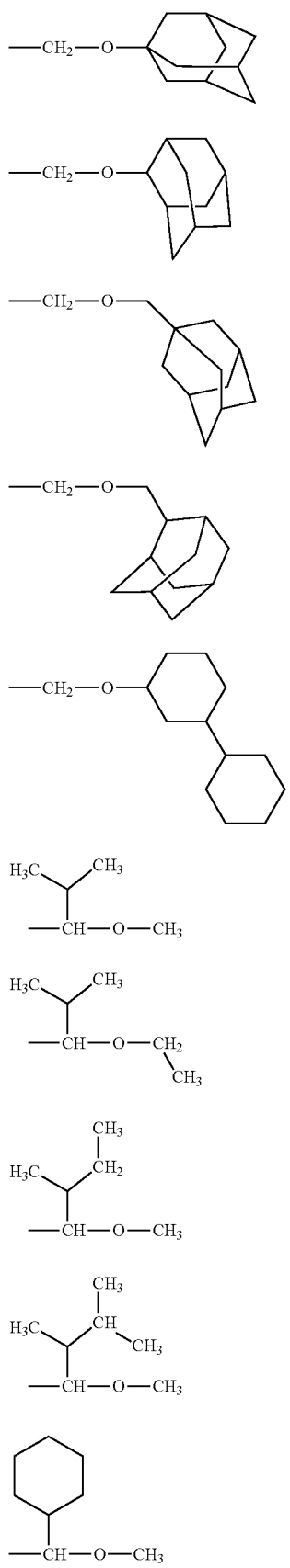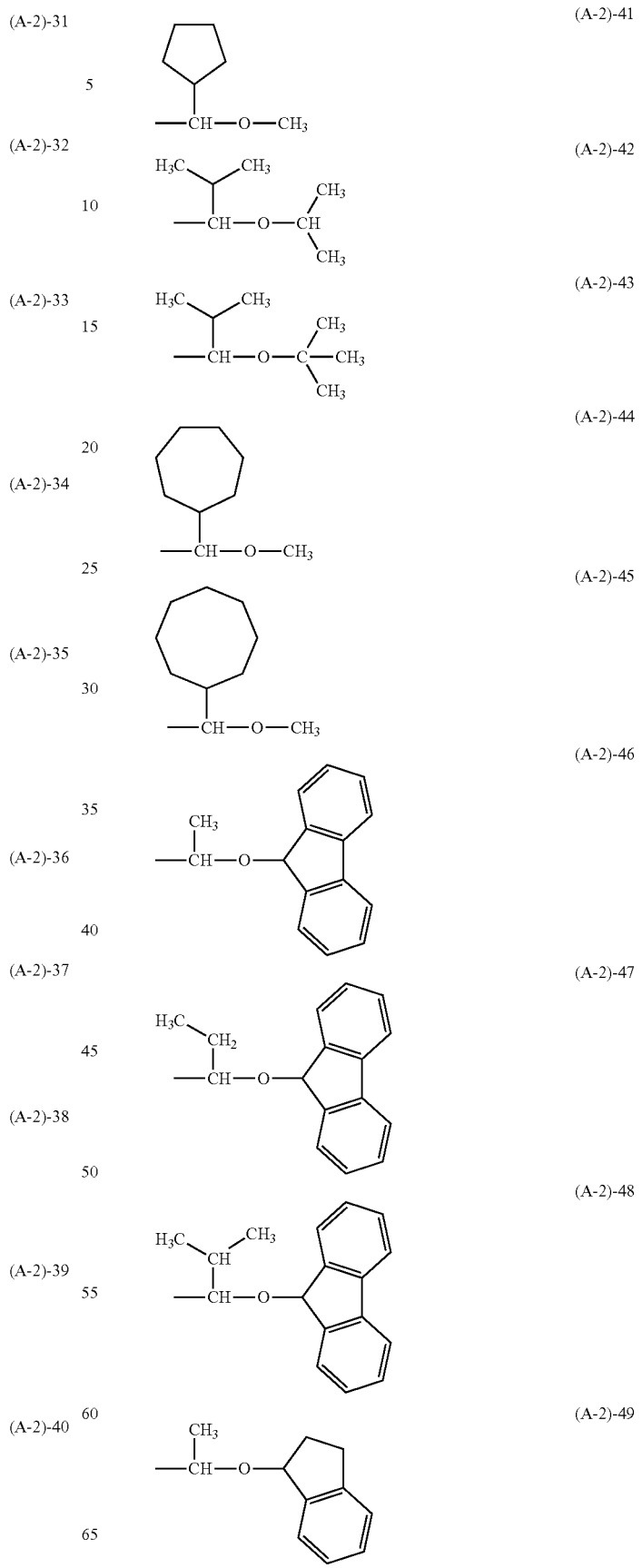

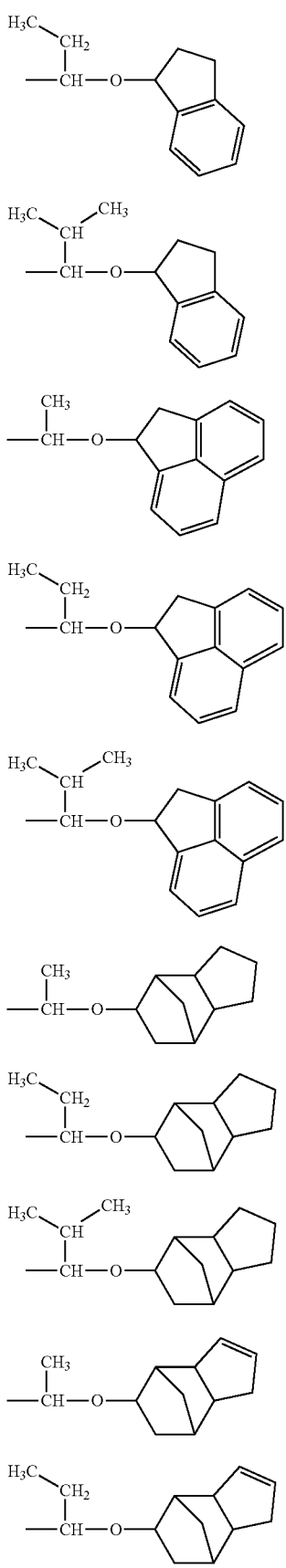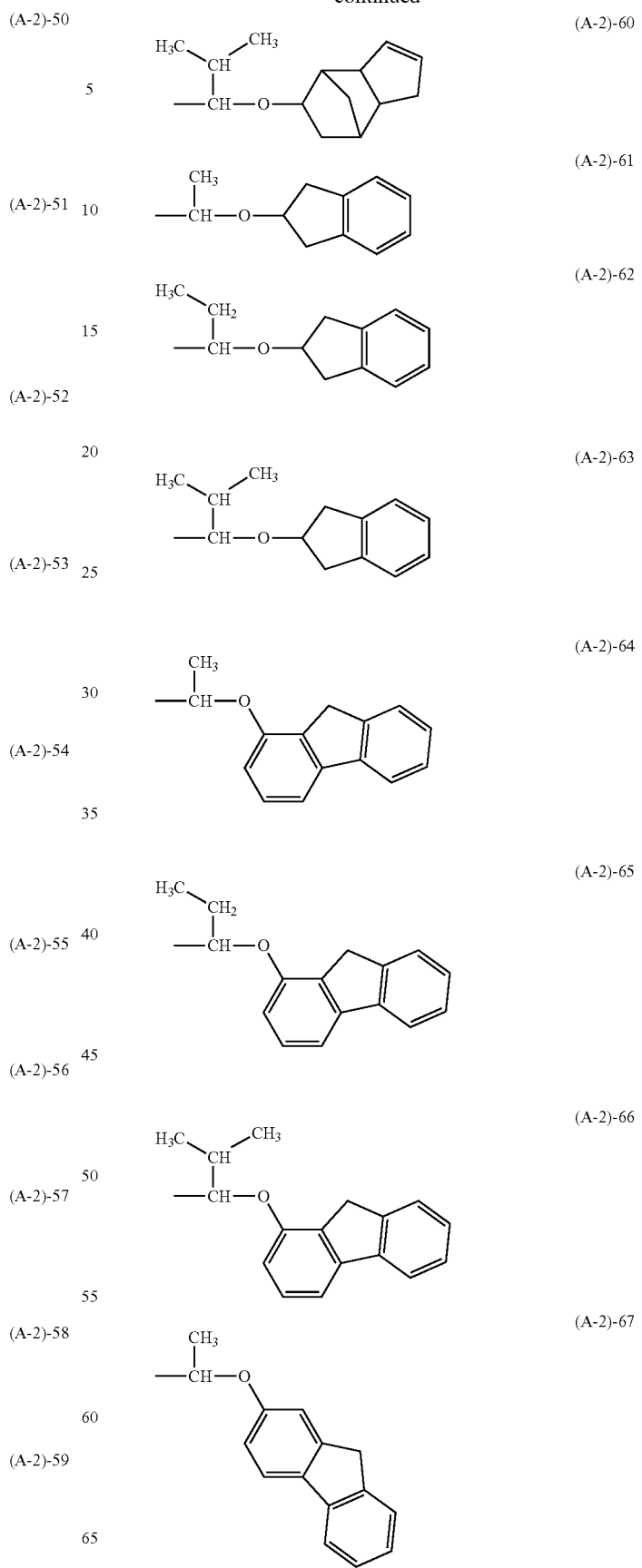

-continued

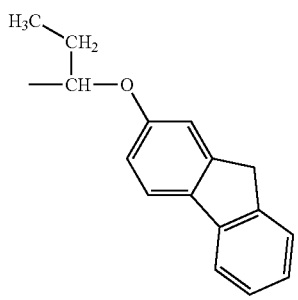
(A-2)-68

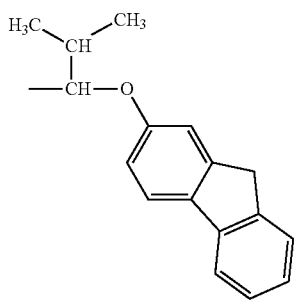
(A-2)-69

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the following formula (A-2a) or (A-2b) while the polymer may be crosslinked within the molecule or between molecules with these acid labile groups.

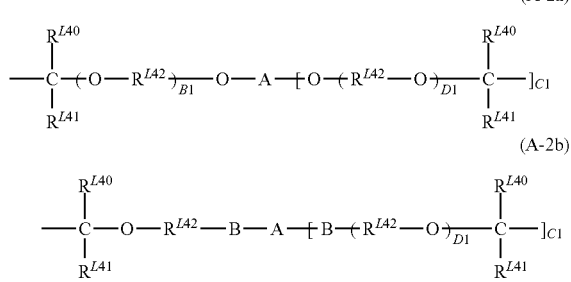

Herein $R^{L40}$ and $R^{L41}$ each are hydrogen or a straight, branched or cyclic $C_1$-$C_8$ alkyl group, or $R^{L40}$ and $R^{L41}$, taken together, may form a ring with the carbon atom to which they are attached, and $R^{L40}$ and $R^{L41}$ are straight or branched $C_1$-$C_8$ alkylene groups when they form a ring. $R^{L42}$ is a straight, branched or cyclic $C_1$-$C_{10}$ alkylene group. Each of B1 and D1 is 0 or an integer of 1 to 10, preferably 0 or an integer of 1 to 5, and C1 is an integer of 1 to 7. "A" is a (C1+1)-valent aliphatic or alicyclic saturated hydrocarbon group, aromatic hydrocarbon group or heterocyclic group having 1 to 50 carbon atoms, which may be separated by a heteroatom or in which some of the hydrogen atoms attached to carbon atoms may be substituted by hydroxyl, carboxyl, carbonyl groups or fluorine atoms. "B" is —CO—O—, —NHCO—O— or —NHCONH—.

Preferably, "A" is selected from divalent to tetravalent, straight, branched or cyclic $C_1$-$C_{20}$ alkylene, alkyltriyl and alkyltetrayl groups, and $C_6$-$C_{30}$ arylene groups, which may be separated by a heteroatom or in which some of the hydrogen atoms attached to carbon atoms may be substituted by hydroxyl, carboxyl, acyl groups or halogen atoms. The subscript C1 is preferably an integer of 1 to 3.

The crosslinking acetal groups of formulae (A-2a) and (A-2b) are exemplified by the following formulae (A-2)-70 through (A-2)-77.

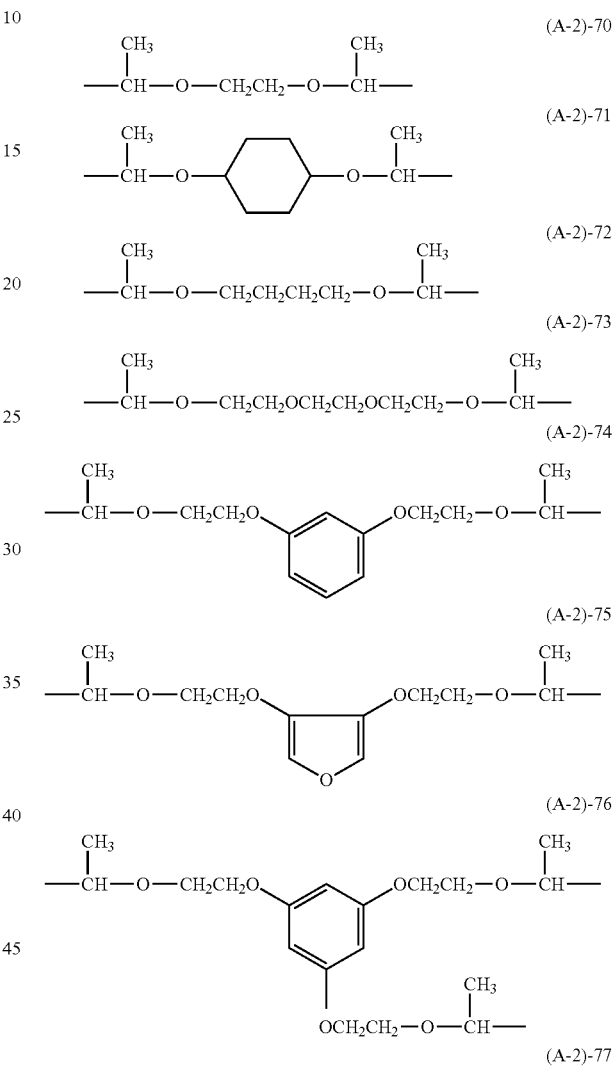

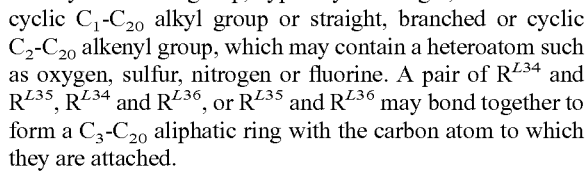

In formula (A-3), $R^{L34}$, $R^{L35}$ and $R^{L36}$ each are a monovalent hydrocarbon group, typically a straight, branched or cyclic $C_1$-$C_{20}$ alkyl group or straight, branched or cyclic $C_2$-$C_{20}$ alkenyl group, which may contain a heteroatom such as oxygen, sulfur, nitrogen or fluorine. A pair of $R^{L34}$ and $R^{L35}$, $R^{L34}$ and $R^{L36}$, or $R^{L35}$ and $R^{L36}$ may bond together to form a $C_3$-$C_{20}$ aliphatic ring with the carbon atom to which they are attached.

Exemplary tertiary alkyl groups of formula (A-3) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, and tert-amyl.

Other exemplary tertiary alkyl groups include those of the following formulae (A-3)-1 to (A-3)-18.
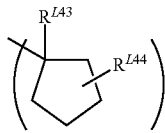 (A-3)-1
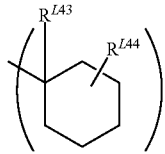 (A-3)-2
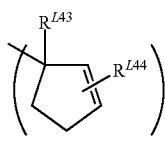 (A-3)-3
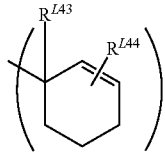 (A-3)-4
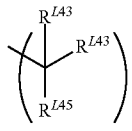 (A-3)-5
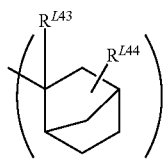 (A-3)-6
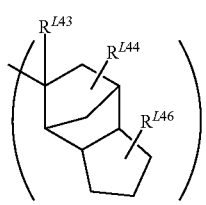 (A-3)-7
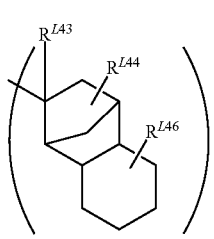 (A-3)-8
-continued
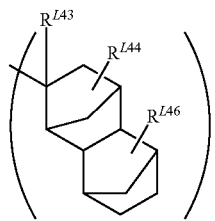 (A-3)-9
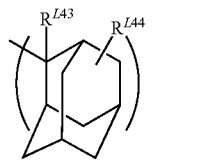 (A-3)-10
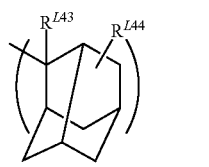 (A-3)-11
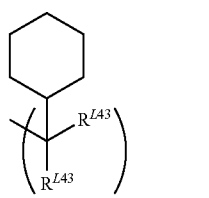 (A-3)-12
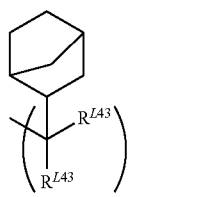 (A-3)-13
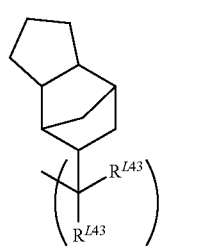 (A-3)-14
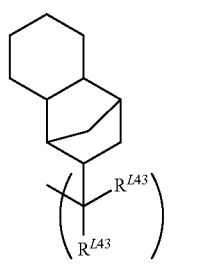 (A-3)-15

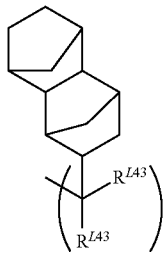
(A-3)-16

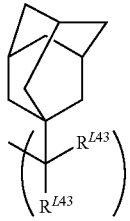
(A-3)-17

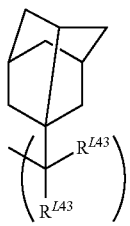
(A-3)-18

Herein $R^{L43}$ is each independently a straight, branched or cyclic $C_1$-$C_8$ alkyl group or $C_6$-$C_{20}$ aryl group, typically phenyl, $R^{L44}$ and $R^{L46}$ each are hydrogen or a straight, branched or cyclic $C_1$-$C_{20}$ alkyl group, and $R^{L45}$ is a $C_6$-$C_{20}$ aryl group, typically phenyl.

The polymer may be crosslinked within the molecule or between molecules with groups having $R^{L47}$ which is a di- or multi-valent alkylene or arylene group, as shown by the following formulae (A-3)-19 and (A-3)-20.

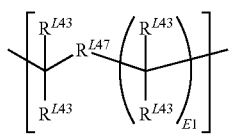
(A-3)-19

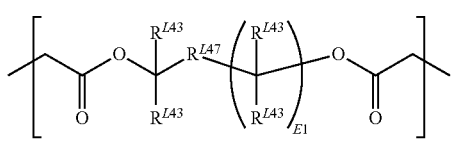
(A-3)-20

Herein $R^{L43}$ is as defined above, $R^{L47}$ is a straight, branched or cyclic $C_1$-$C_{20}$ alkylene group or arylene group, typically phenylene, which may contain a heteroatom such as oxygen, sulfur or nitrogen, and E1 is an integer of 1 to 3.

Of recurring units having acid labile groups of formula (A-3), recurring units of (meth)acrylate having an exo-form structure represented by the formula (A-3)-21 are preferred.

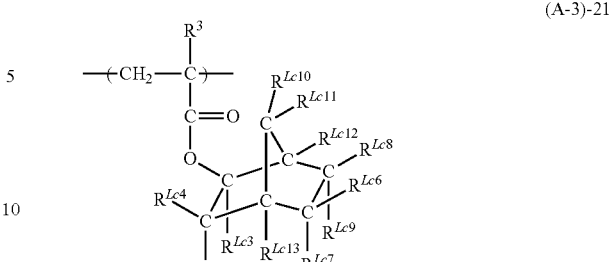
(A-3)-21

Herein, $R^3$ is hydrogen or methyl; $R^{Lc3}$ is a straight, branched or cyclic $C_1$-$C_8$ alkyl group or an optionally substituted $C_6$-$C_{20}$ aryl group; $R^{Lc4}$ to $R^{Lc9}$, $R^{Lc12}$ and $R^{Lc13}$ are each independently hydrogen or a monovalent $C_1$-$C_{15}$ hydrocarbon group which may contain a heteroatom; and $R^{Lc10}$ and $R^{Lc11}$ are hydrogen or a monovalent $C_1$-$C_{15}$ hydrocarbon group which may contain a heteroatom. Alternatively, a pair of $R^{Lc4}$ and $R^{Lc5}$, $R^{Lc6}$ and $R^{Lc8}$, $R^{Lc6}$ and $R^{Lc9}$, $R^{Lc7}$ and $R^{Lc9}$, $R^{Lc7}$ and $R^{Lc13}$, $R^{Lc8}$ and $R^{Lc12}$, $R^{Lc10}$ and $R^{Lc11}$, or $R^{Lc11}$ and $R^{Lc12}$, taken together, may form a ring, and in that event, each ring-forming R is a divalent $C_1$-$C_{15}$ hydrocarbon group which may contain a heteroatom. Also, a pair of $R^{Lc4}$ and $R^{Lc13}$, $R^{Lc10}$ and $R^{Lc13}$, or $R^{Lc6}$ and $R^{Lc8}$ which are attached to vicinal carbon atoms may bond together directly to form a double bond. The formula also represents an enantiomer.

The ester form monomers from which recurring units having an exo-form structure represented by formula (A-3)-21 are derived are described in U.S. Pat. No. 6,448,420 (JP-A 2000-327633). Illustrative non-limiting examples of suitable monomers are given below.

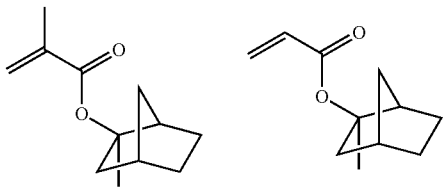

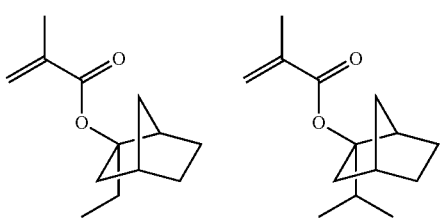

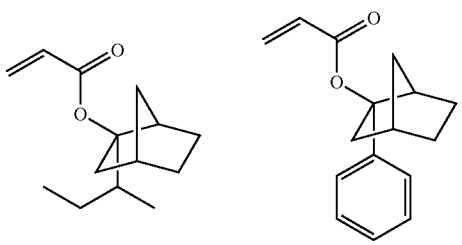

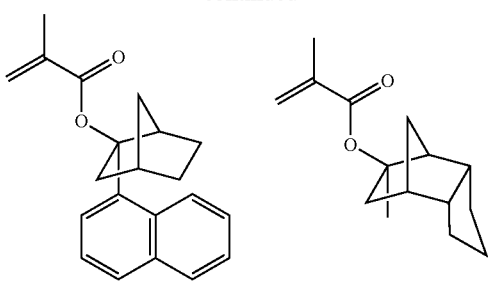
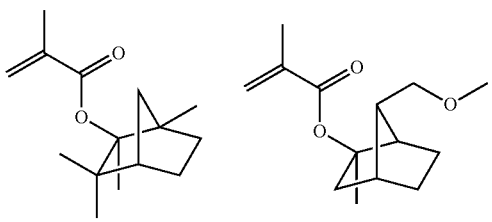
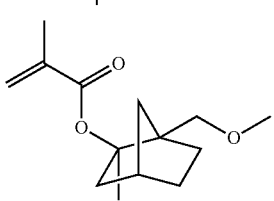
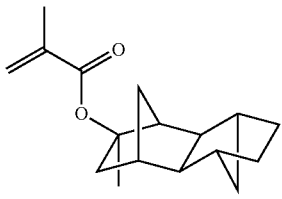
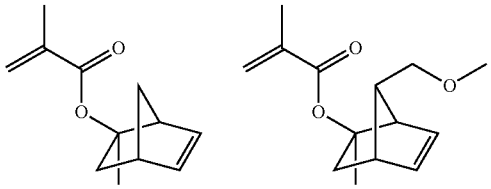
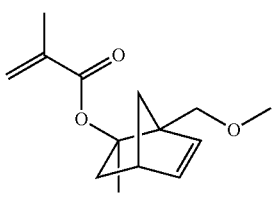
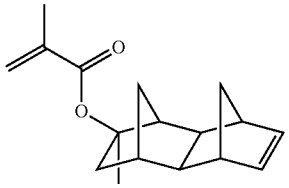
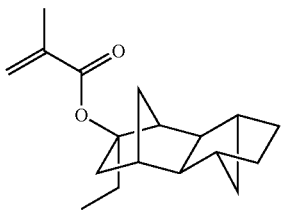

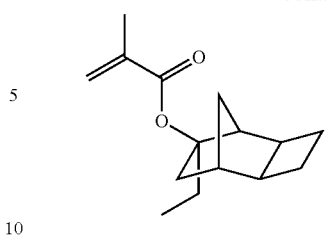
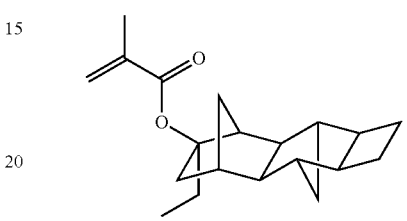

Also included in the acid labile groups of formula (A-3) are acid labile groups of (meth)acrylate having furandiyl, tetrahydrofurandiyl or oxanorbornanediyl as represented by the following formula (A-3)-22.

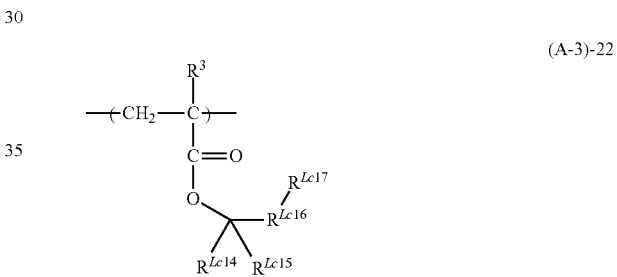

(A-3)-22

Herein, $R^3$ is as defined above; $R^{Lc14}$ and $R^{Lc15}$ are each independently a monovalent, straight, branched or cyclic $C_1$-$C_{10}$ hydrocarbon group, or $R^{Lc14}$ and $R^{Lc15}$, taken together, may form an aliphatic hydrocarbon ring with the carbon atom to which they are attached. $R^{Lc16}$ is a divalent group selected from furandiyl, tetrahydrofurandiyl and oxanorbornanediyl. $R^{Lc17}$ is hydrogen or a monovalent, straight, branched or cyclic $C_1$-$C_{10}$ hydrocarbon group which may contain a heteroatom.

Examples of the monomers from which the recurring units substituted with acid labile groups having furandiyl, tetrahydrofurandiyl and oxanorbornanediyl are derived are shown below. Note that Me is methyl and Ac is acetyl.

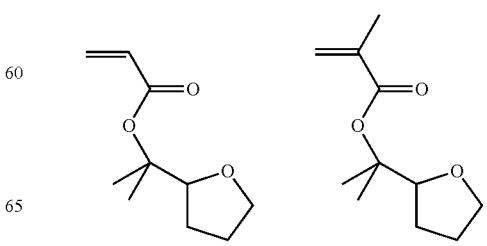

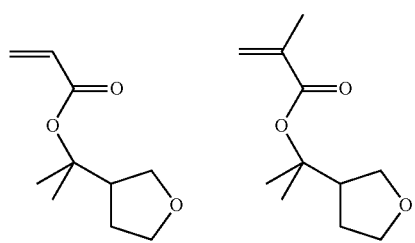
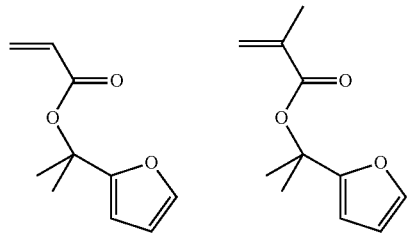
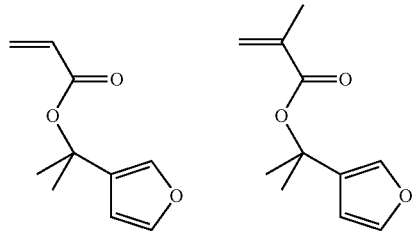
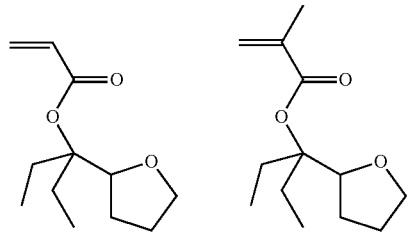
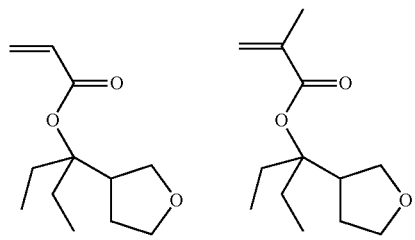
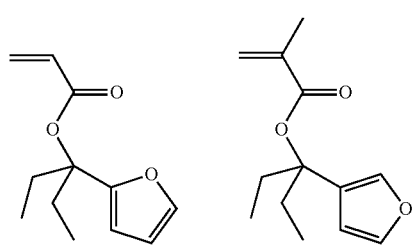
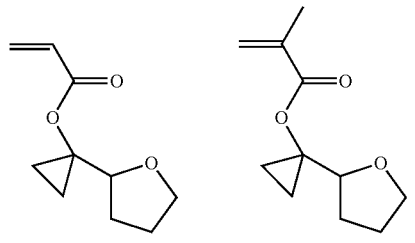
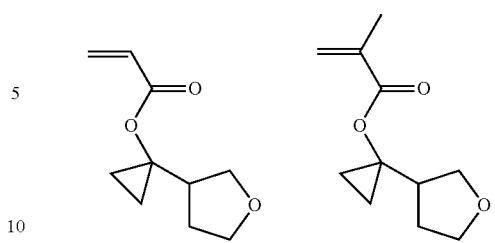
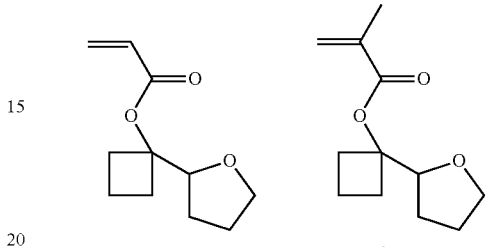
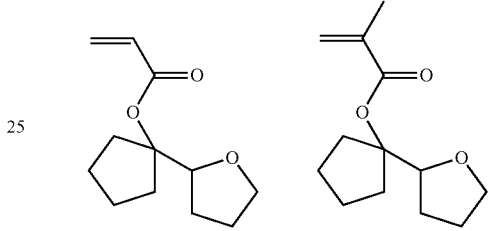
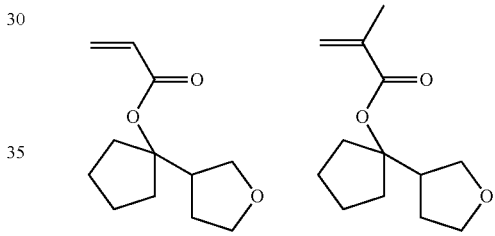
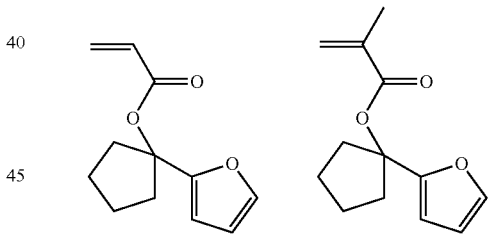
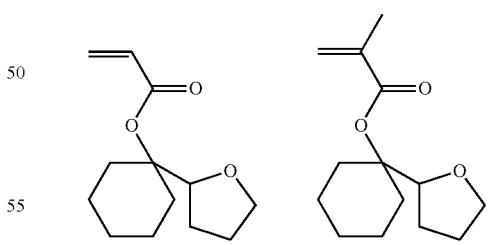
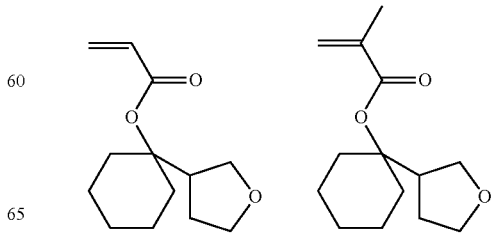

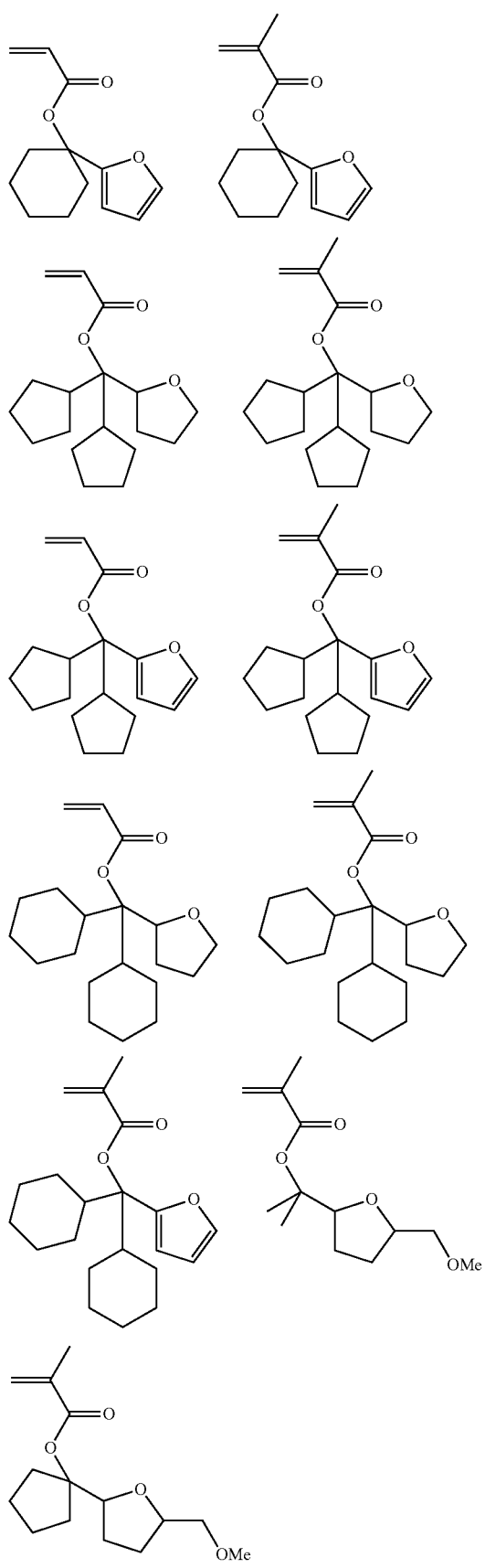
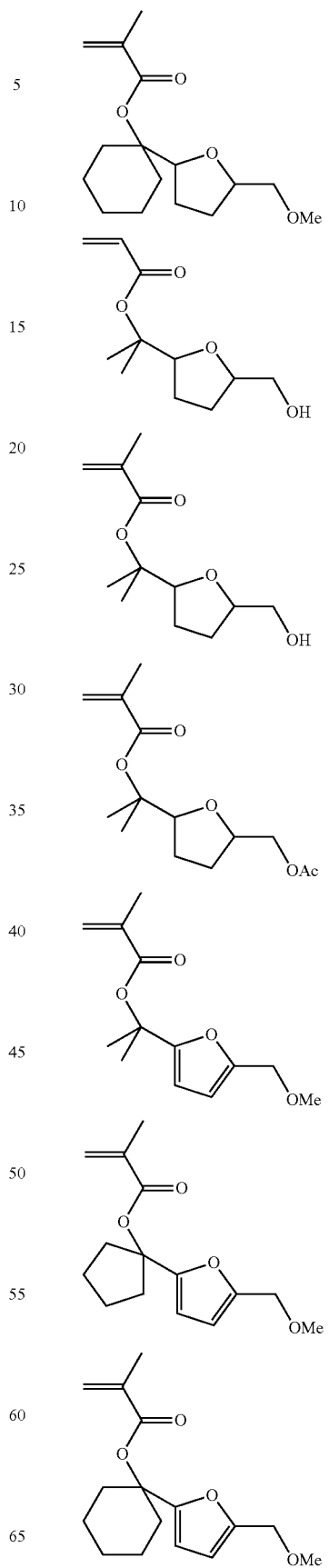

-continued
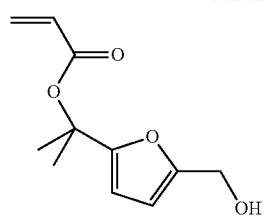
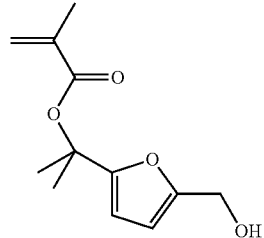
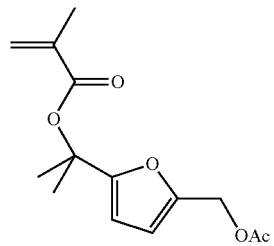
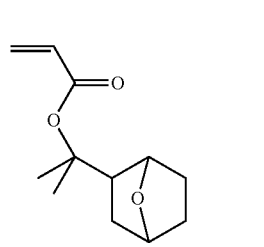
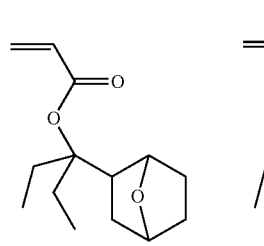
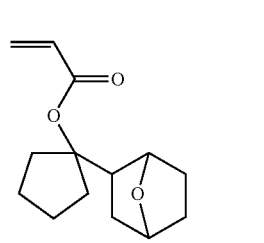
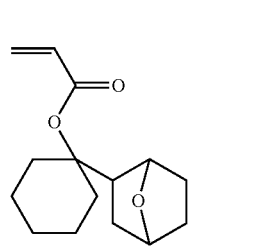
-continued
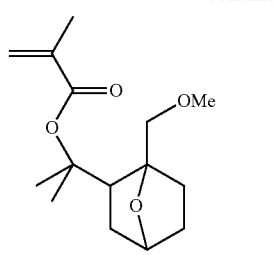
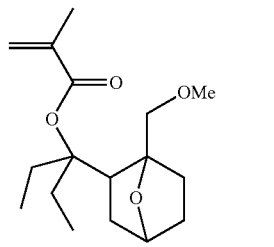
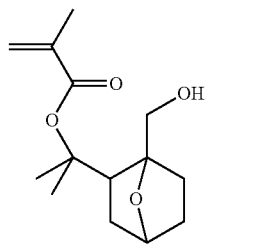
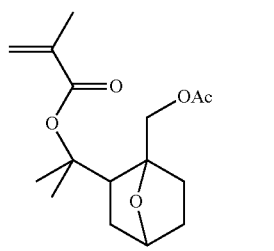
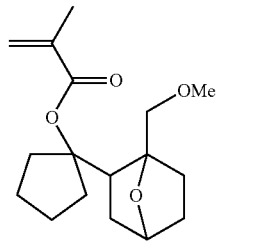

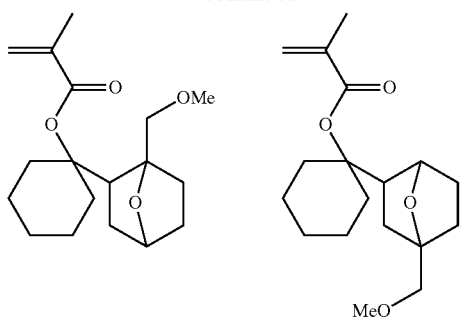
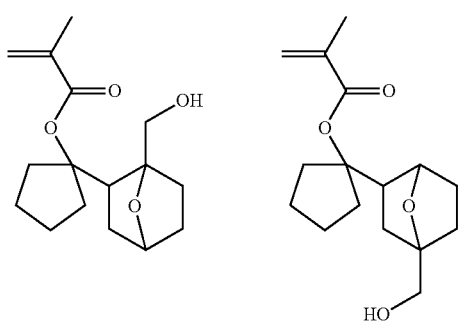
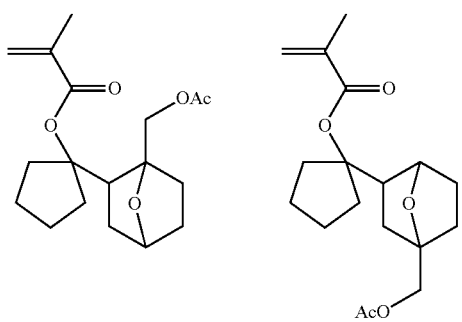

In the recurring unit (b1), the hydrogen atom of the carboxyl group may be substituted by an acid labile group having the general formula (A-3)-23.

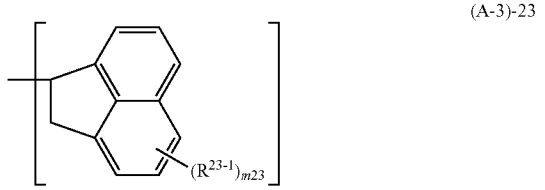

(A-3)-23

Herein $R^{23-1}$ is hydrogen, $C_1$-$C_4$ alkyl, alkoxy, alkanoyl, alkoxycarbonyl, $C_6$-$C_{10}$ aryl, halogen, or cyano group, and m23 is an integer of 1 to 4.

Examples of the monomer having a carboxyl group substituted with an acid labile group of formula (A-3)-23 are given below.

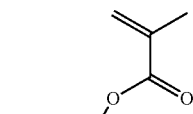 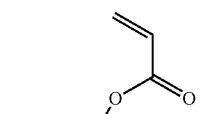
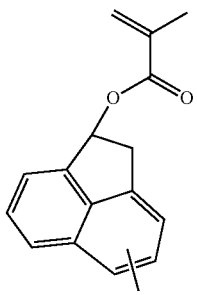 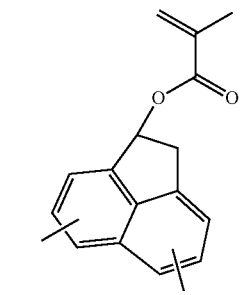
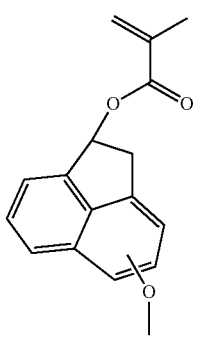 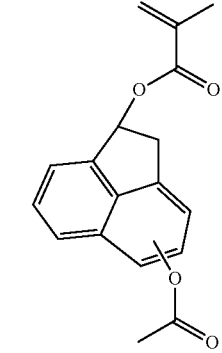
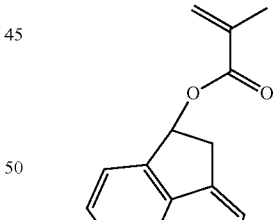 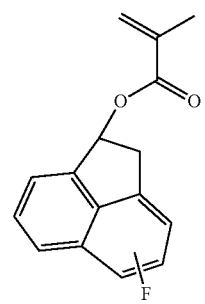
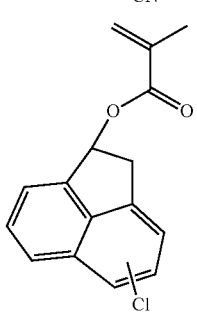

-continued

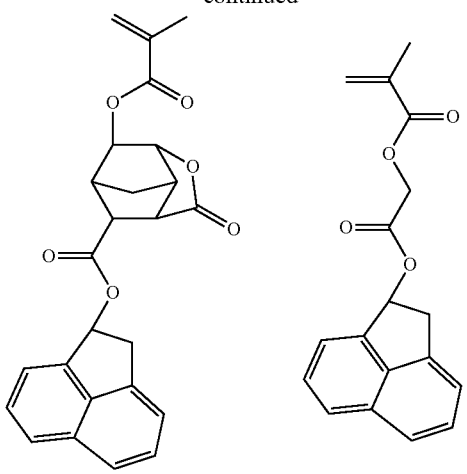

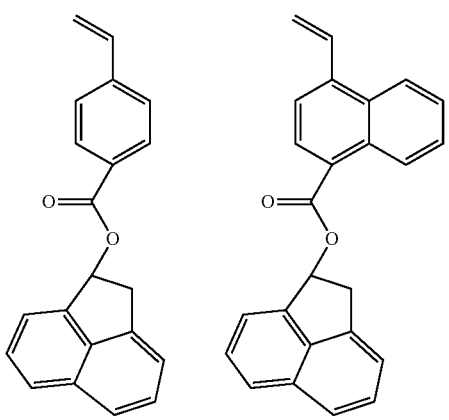

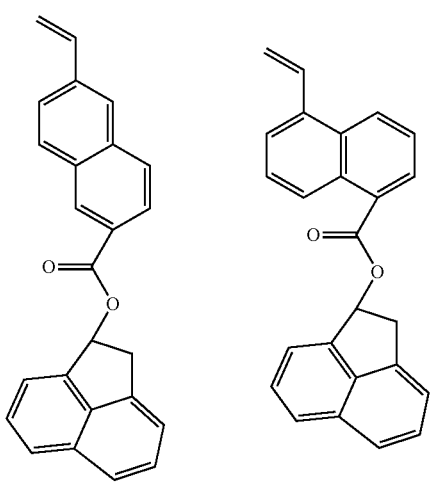 [SMILES: C=Cc1ccc2cc(C(=O)OC3Cc4cccc5cccc3c45)ccc2c1 ; C=Cc1cccc2c(C(=O)OC3Cc4cccc5cccc3c45)cccc12]

In the recurring unit (b1), the hydrogen atom of the carboxyl group may be substituted by an acid labile group having the general formula (A-3)-24.

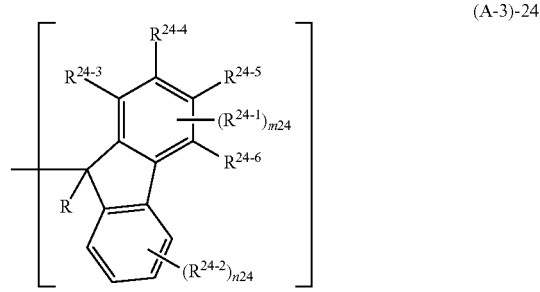

(A-3)-24

Herein $R^{24-1}$ and $R^{24-2}$ each are hydrogen, $C_1$-$C_4$ alkyl, alkoxy, alkanoyl, alkoxycarbonyl, hydroxyl, $C_6$-$C_{10}$ aryl, halogen, or cyano group; R is hydrogen, a straight, branched or cyclic $C_1$-$C_{12}$ alkyl group which may contain an oxygen or sulfur atom, $C_2$-$C_{12}$ alkenyl, $C_2$-$C_{12}$ alkynyl, or $C_6$-$C_{10}$ aryl group; $R^{24-3}$, $R^{24-4}$ $R^{24-5}$, and $R^{24-6}$ each are hydrogen, or a pair of $R^{24-3}$ and $R^{24-4}$, $R^{24-4}$ and $R^{24-5}$, or $R^{24-5}$ and $R^{24-6}$ may bond together to form a benzene ring; m24 and n24 each are an integer of 1 to 4.

Examples of the monomer having a carboxyl group substituted with an acid labile group of formula (A-3)-24 are given below.

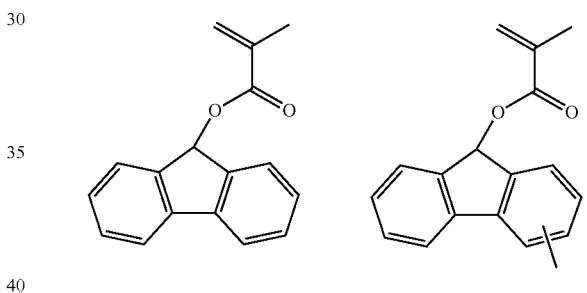

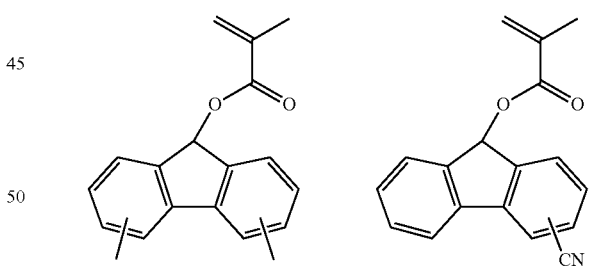

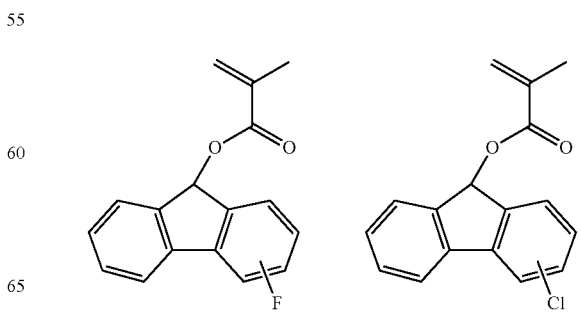

51
-continued
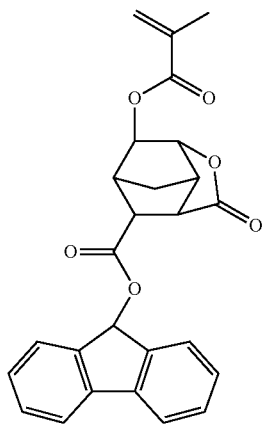
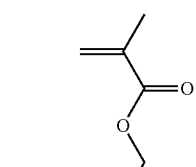
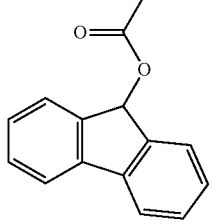
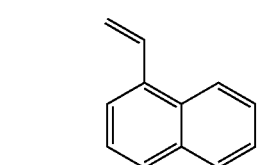
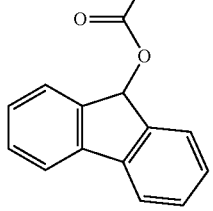
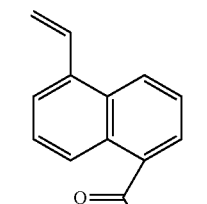
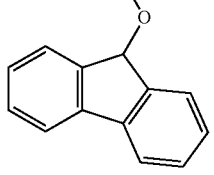
52
-continued
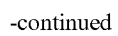
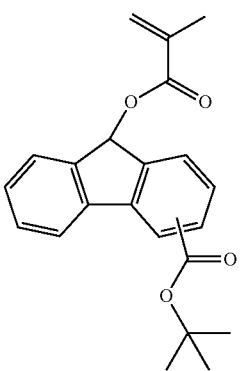
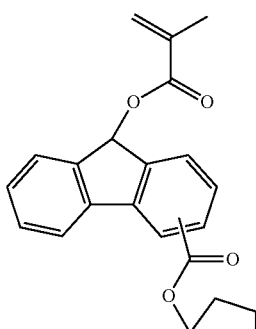
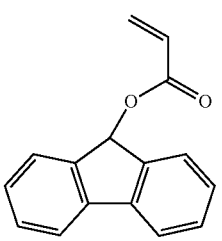
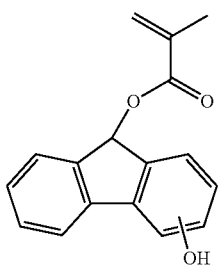
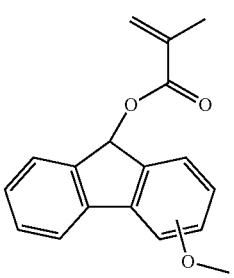
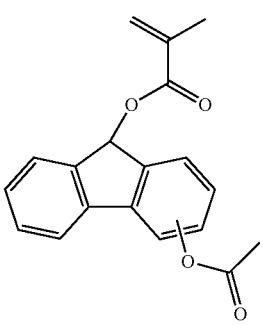
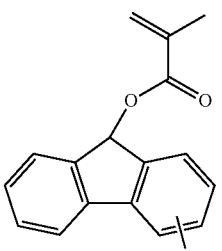
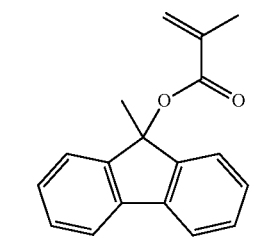
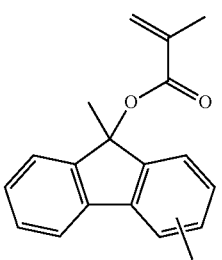
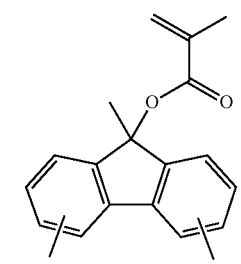

-continued
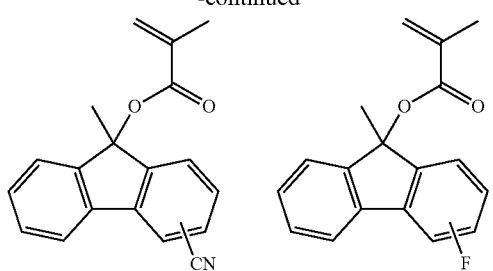
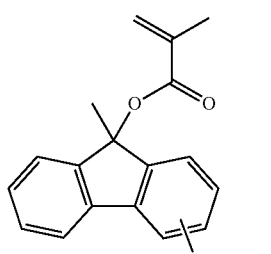
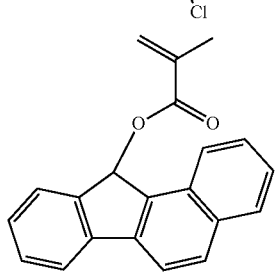
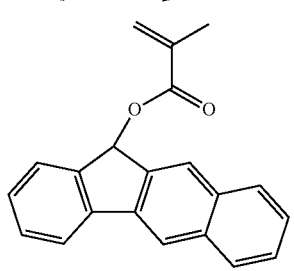
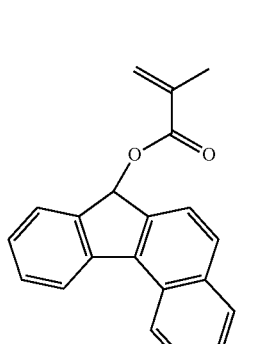
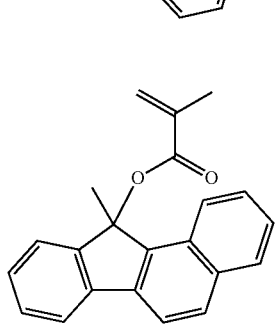
-continued
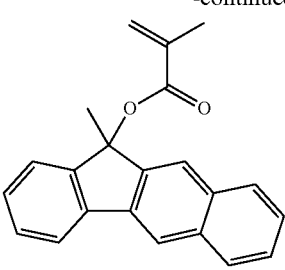
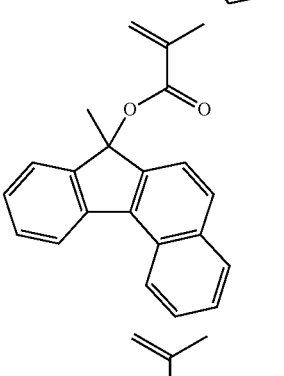
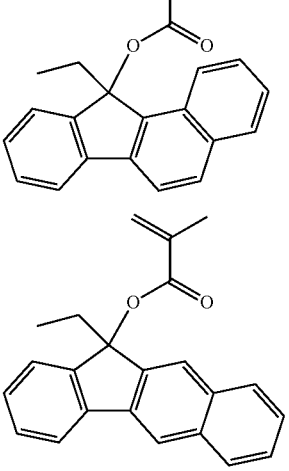
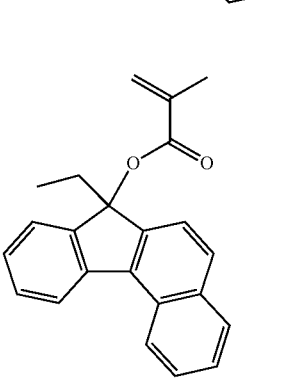
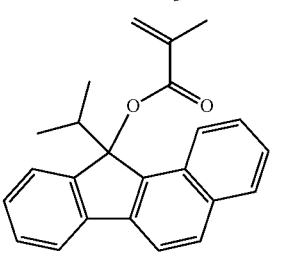

55
-continued
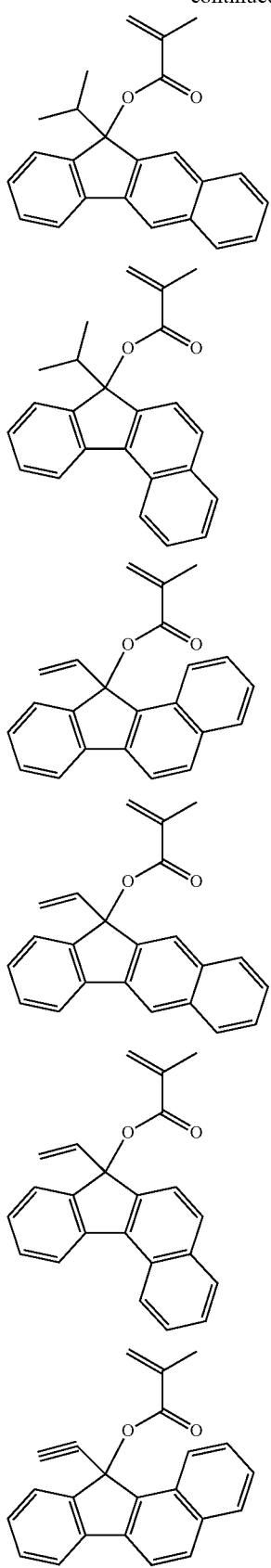
56
-continued
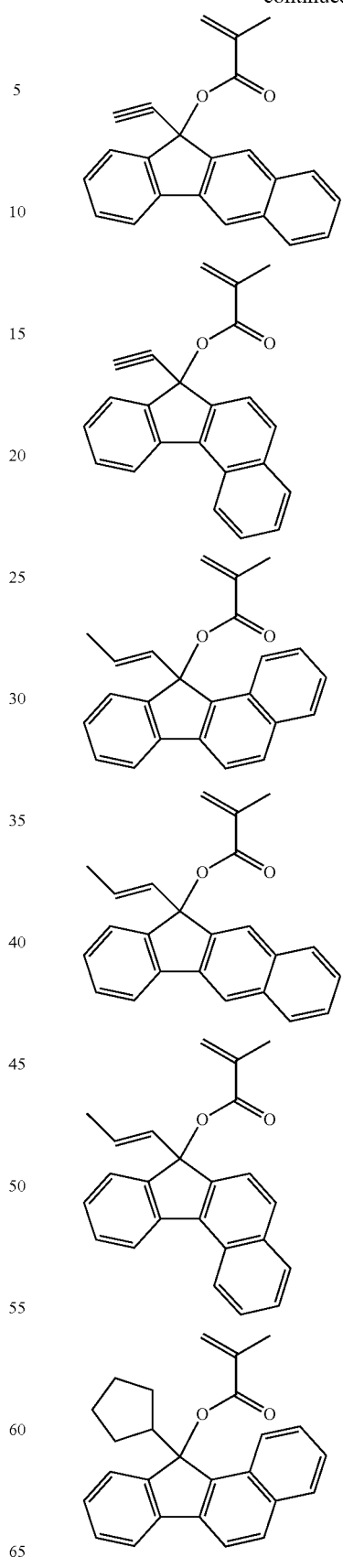

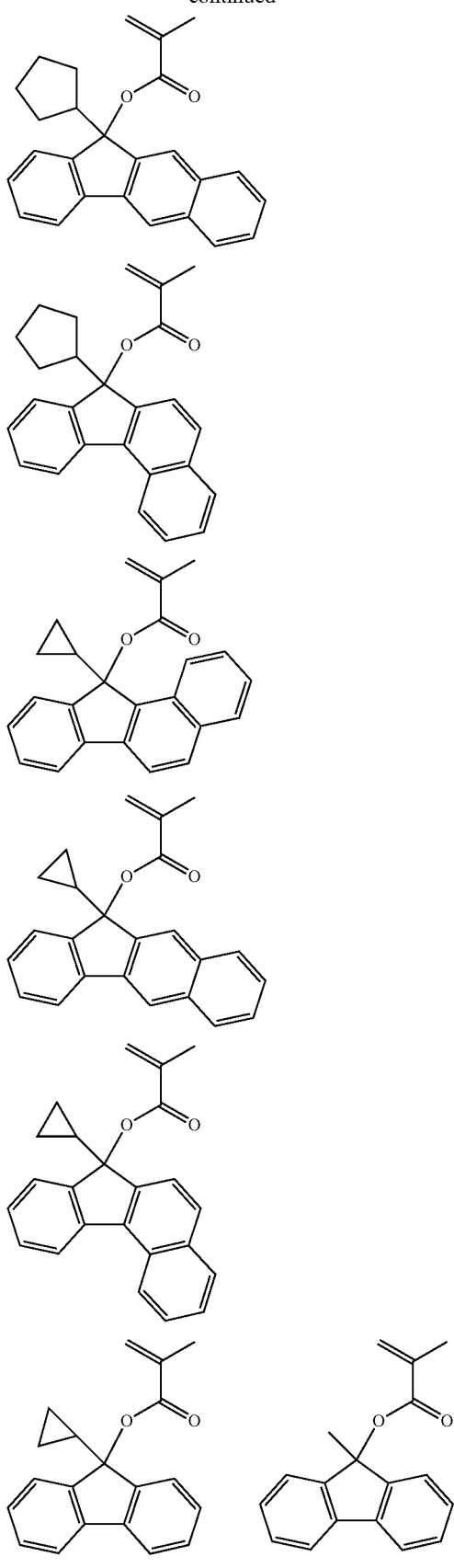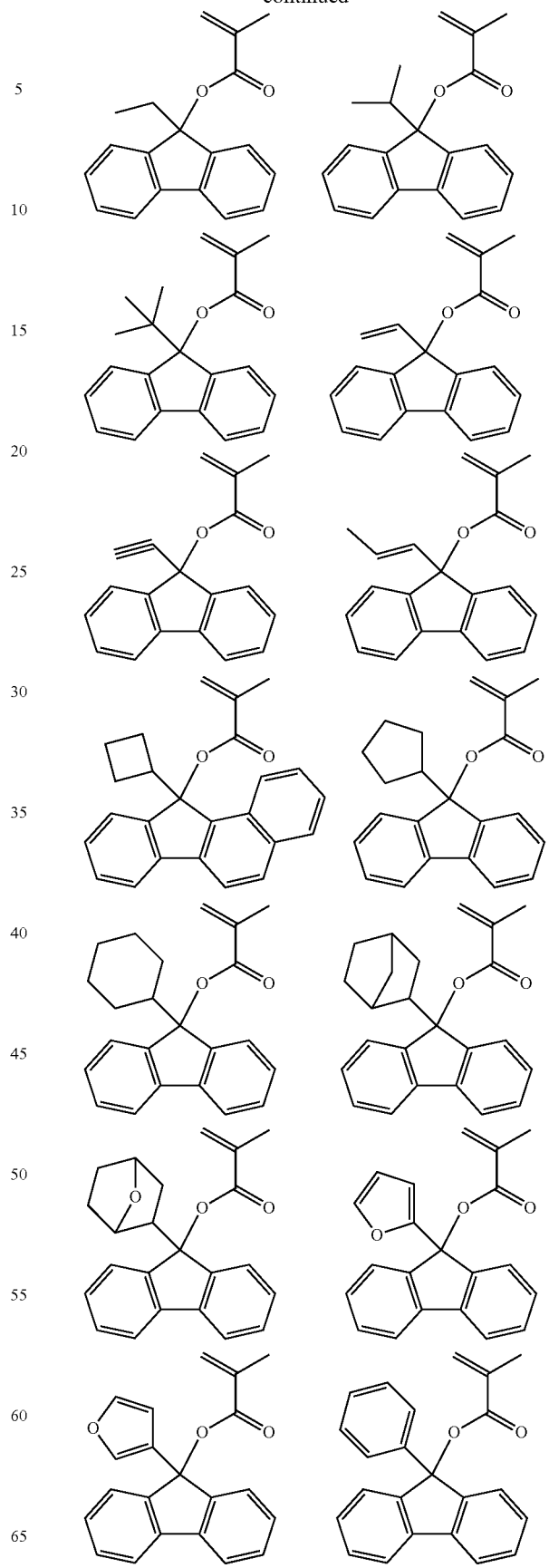

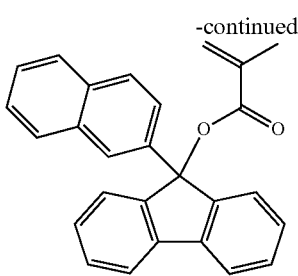
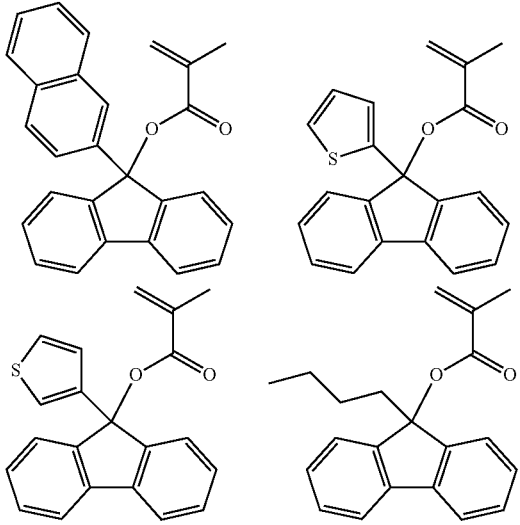
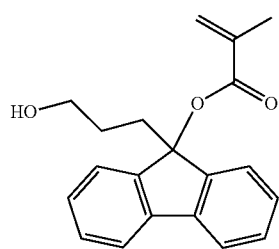
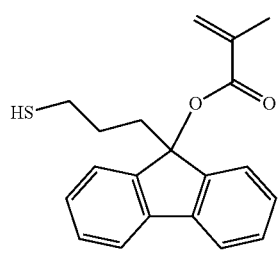
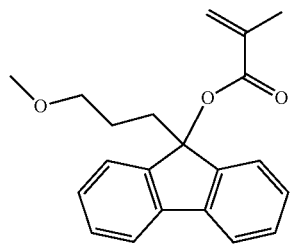

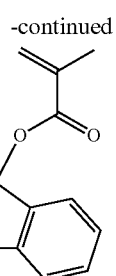

In the recurring unit (b1), the hydrogen atom of the carboxyl group may be substituted by an acid labile group having the general formula (A-3)-25.

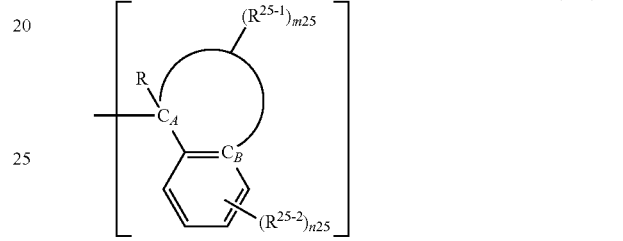

(A-3)-25

Herein $R^{25-1}$ is each independently hydrogen or a straight, branched or cyclic $C_1$-$C_6$ alkyl group, and in case m25 is 2 or more, $R^{25-1}$ may bond together to form a non-aromatic ring of 2 to 8 carbon atoms; the circle denotes a link between carbons $C_A$ and $C_B$, selected from among ethylene, propylene, butylene and pentylene; $R^{25-1}$ is not hydrogen when the circle denotes ethylene or propylene; $R^{25-2}$ is $C_1$-$C_4$ alkyl, alkoxy, alkanoyl, alkoxycarbonyl, hydroxyl, nitro, $C_6$-$C_{10}$ aryl, halogen, or cyano group; R is as defined above; m25 and n25 each are an integer of 1 to 4.

Examples of the monomer having a carboxyl group substituted with an acid labile group of formula (A-3)-25 are given below.

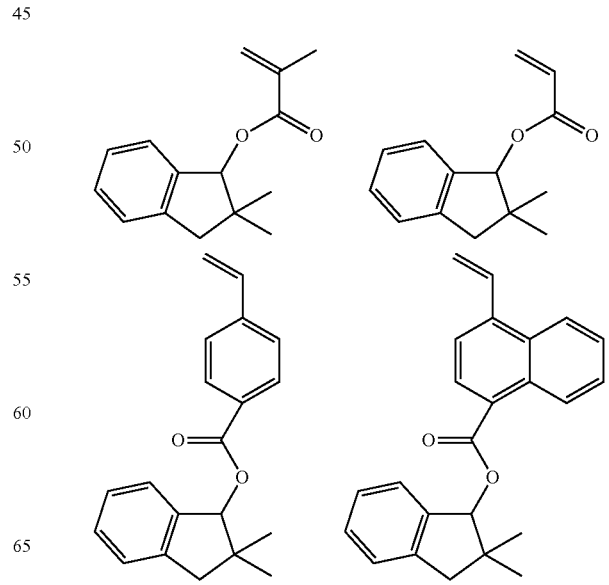

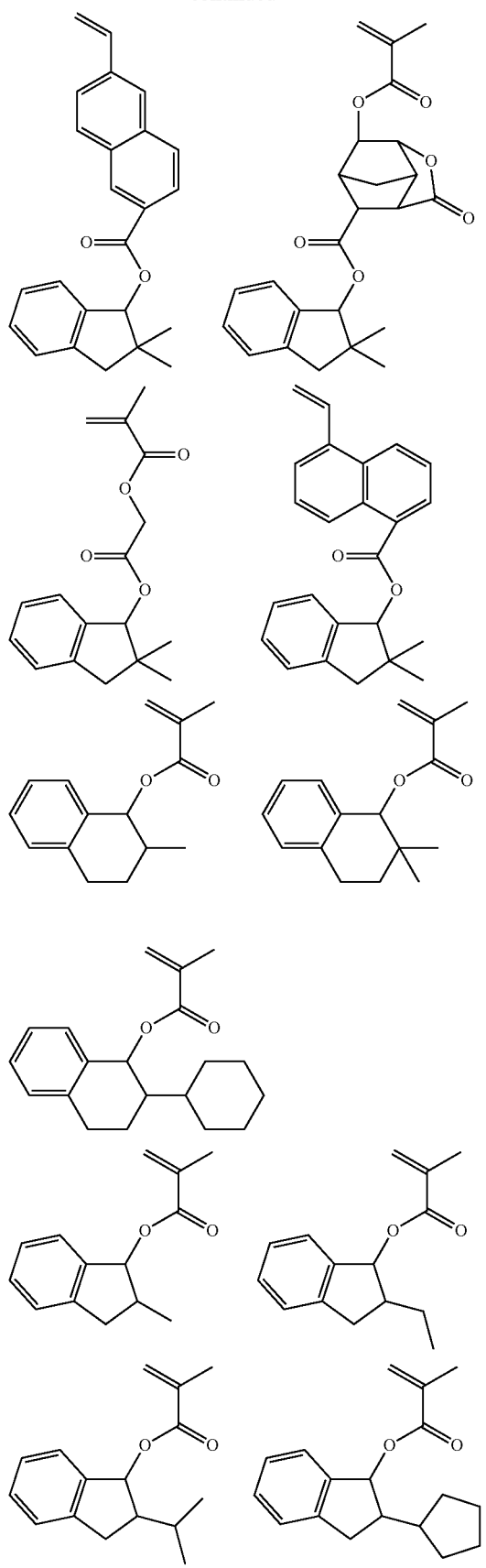
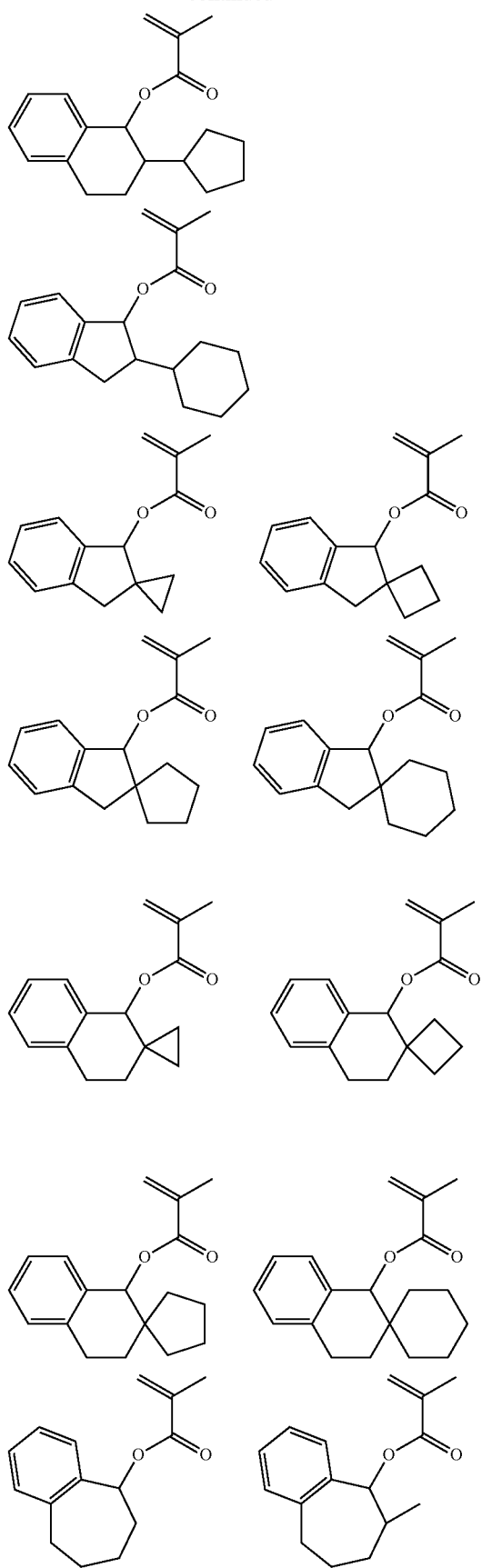

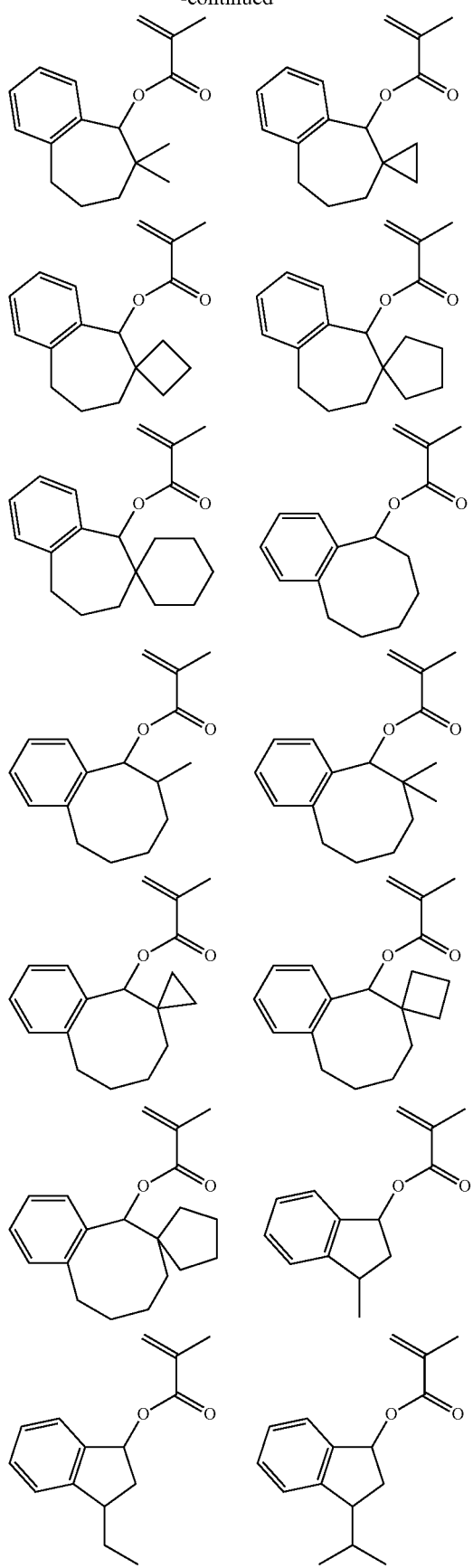
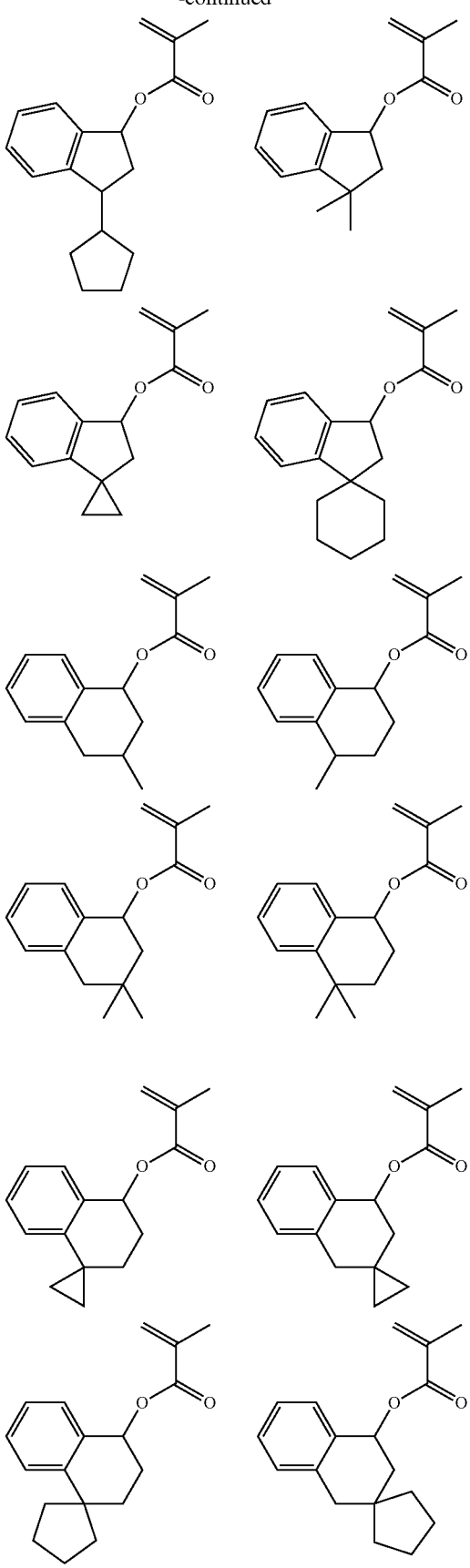

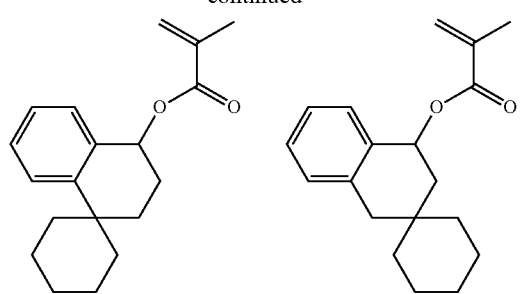
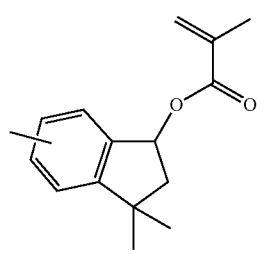
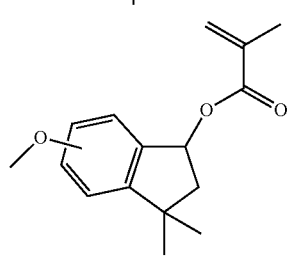
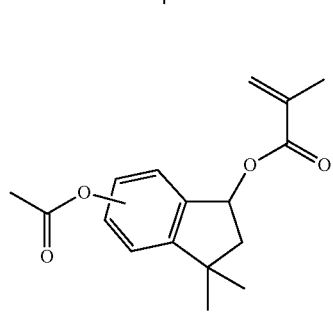
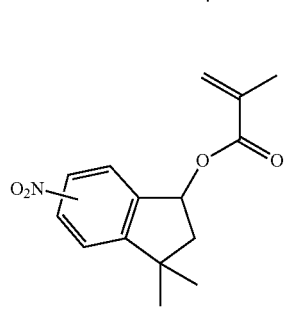
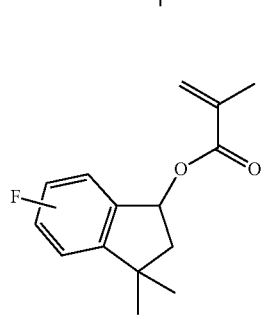
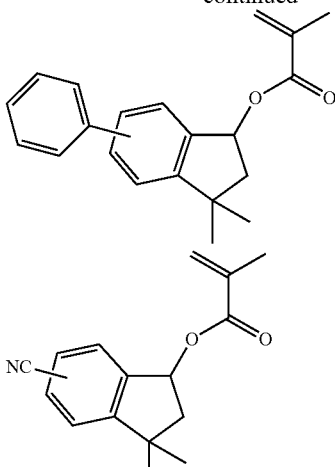
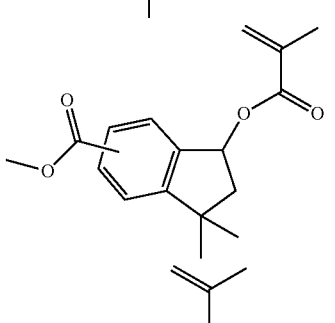
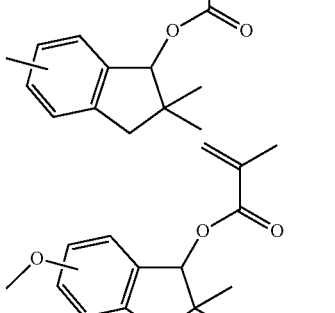
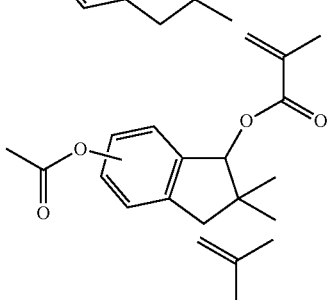
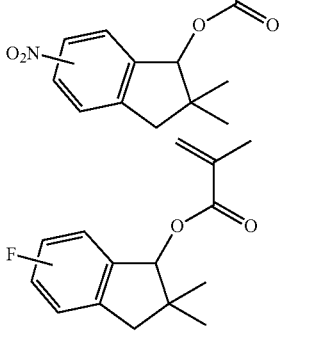

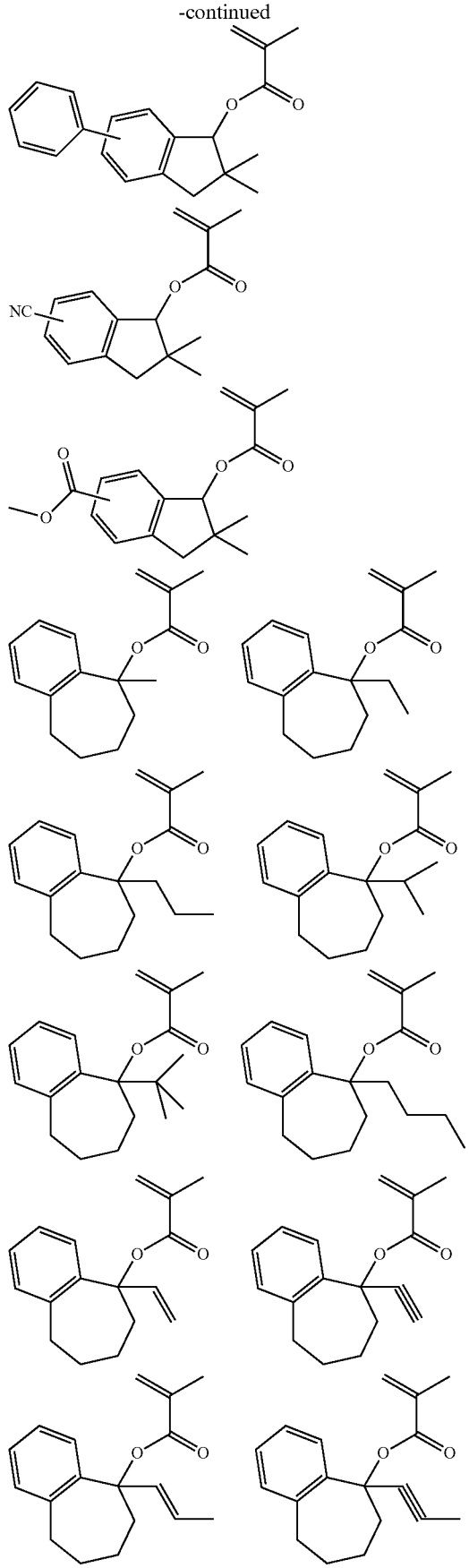
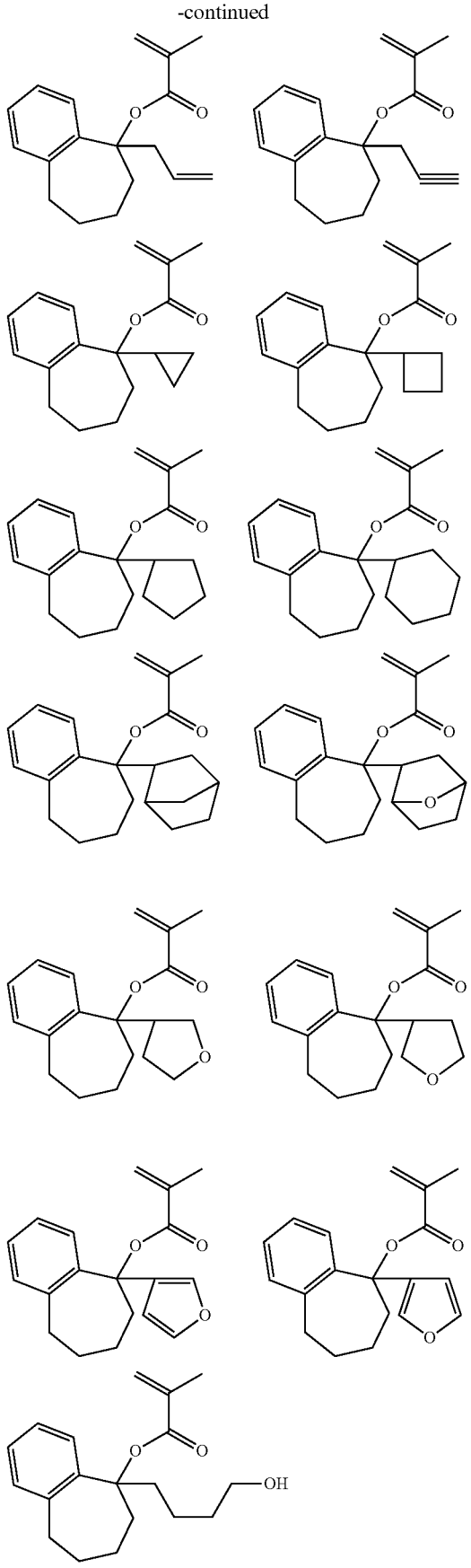

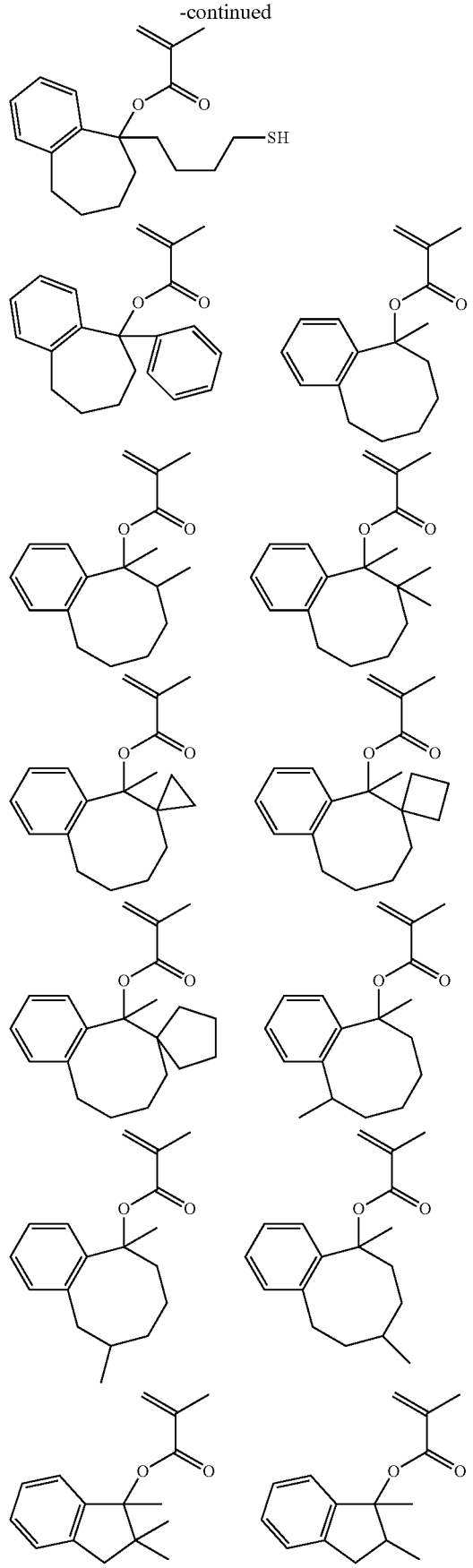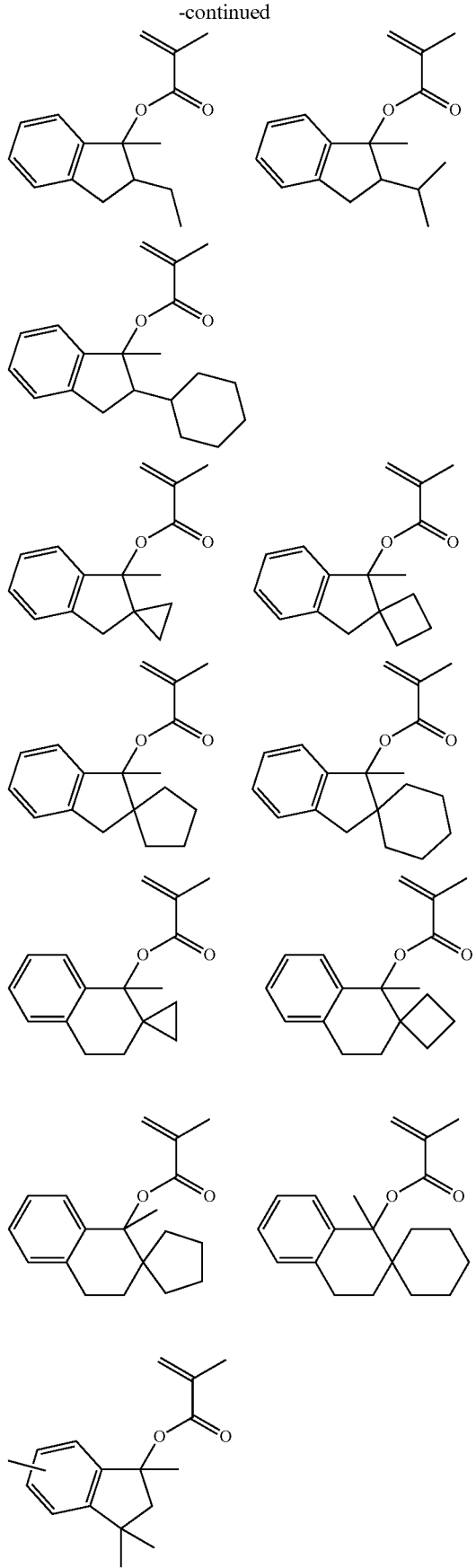

-continued
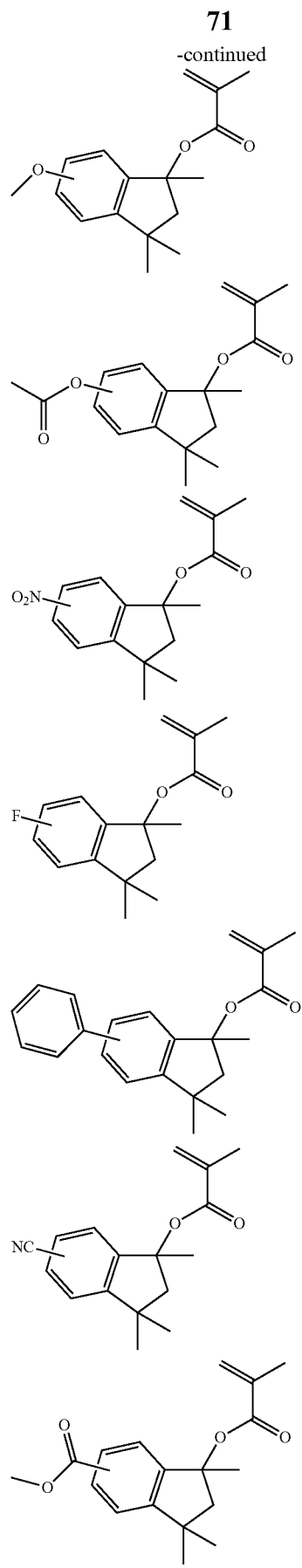
-continued
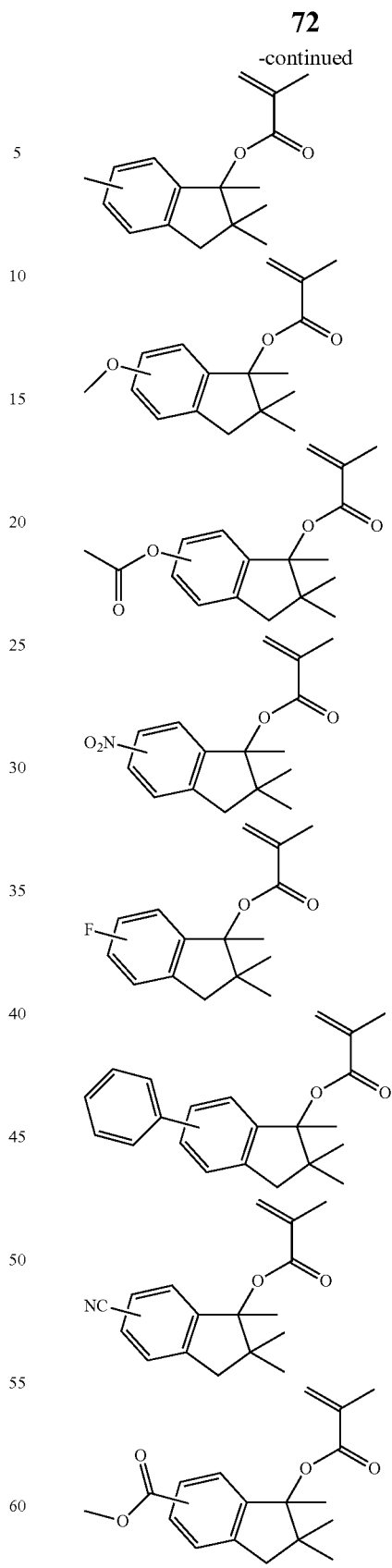
In the recurring unit (b1), the hydrogen atom of the carboxyl group may be substituted by an acid labile group having the general formula (A-3)-26.

(A-3)-26
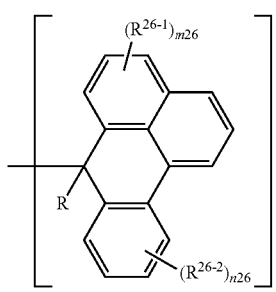
Herein $R^{26-1}$ and $R^{26-2}$ each are hydrogen, $C_1$-$C_4$ alkyl, alkoxy, alkanoyl, alkoxycarbonyl, hydroxyl, nitro, $C_6$-$C_{10}$ aryl, halogen, or cyano group; R is as defined above; and m26 and n26 each are an integer of 1 to 4.
Examples of the monomer having a carboxyl group substituted with an acid labile group of formula (A-3)-26 are given below.
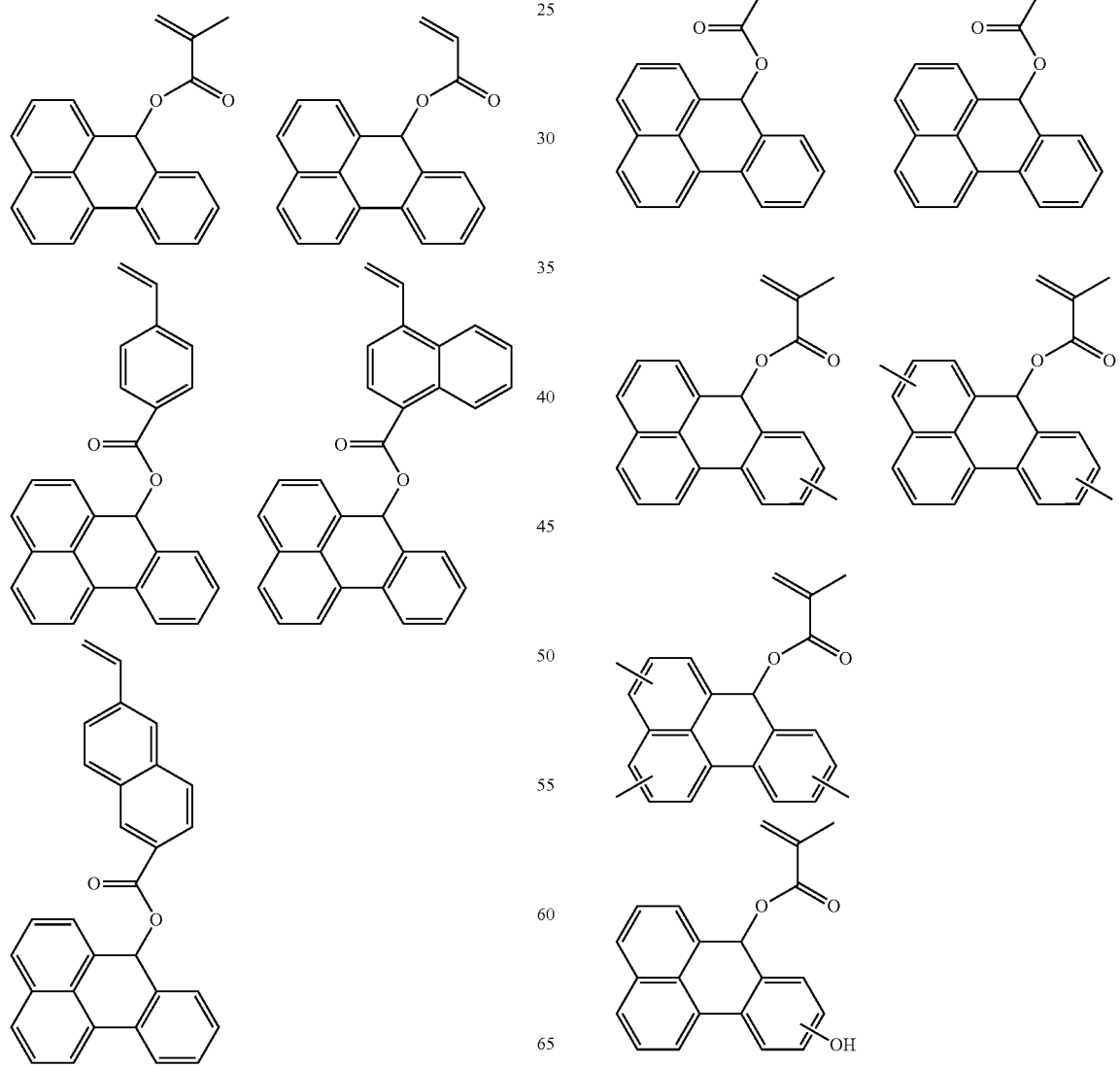
-continued

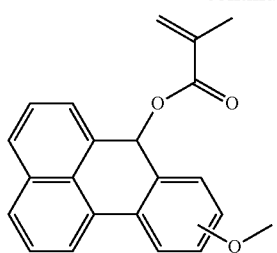
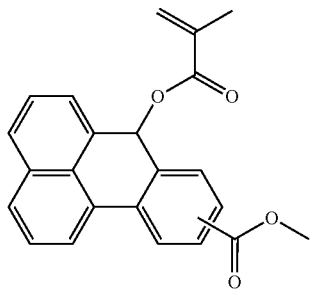
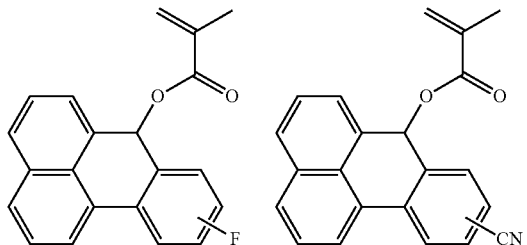
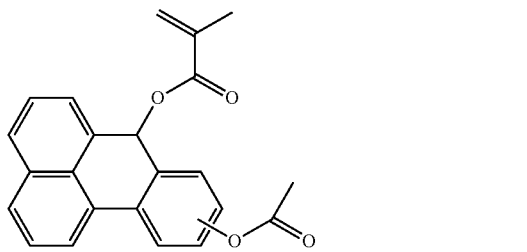
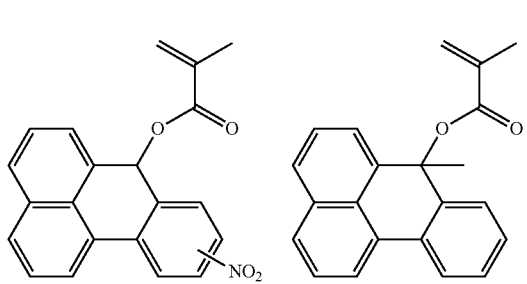
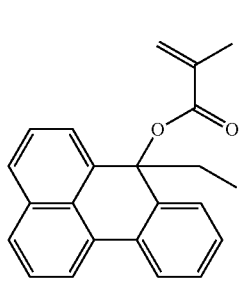
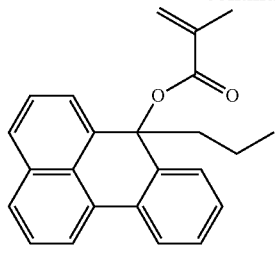
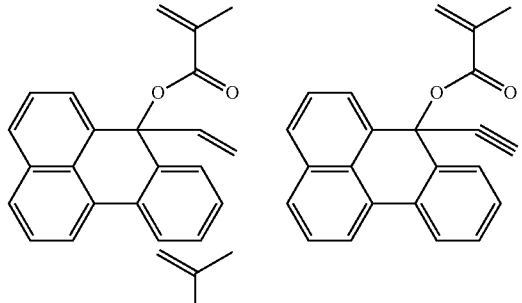
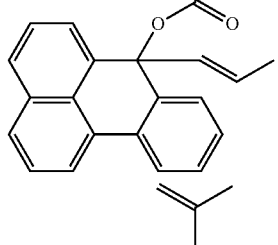
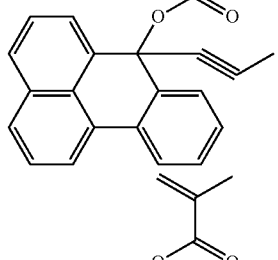
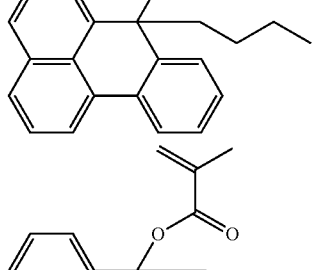
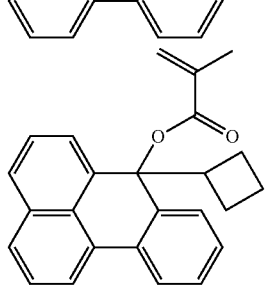

77
-continued
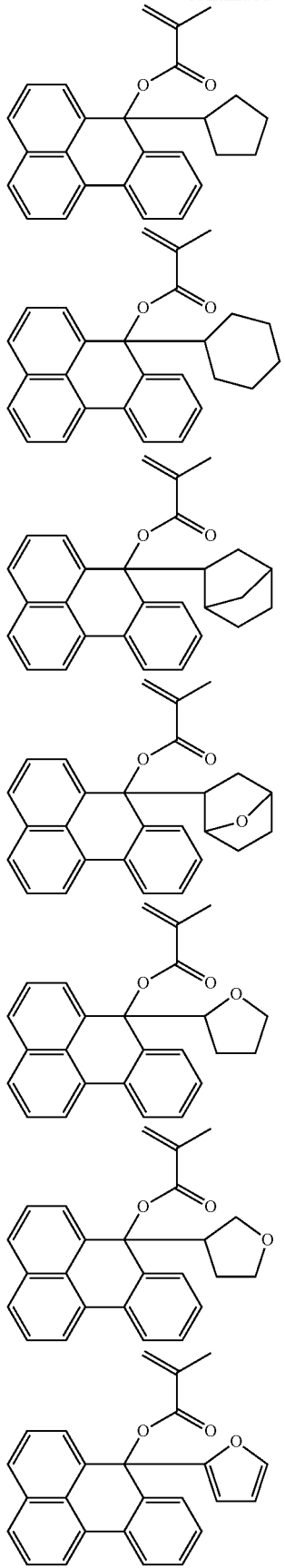
78
-continued
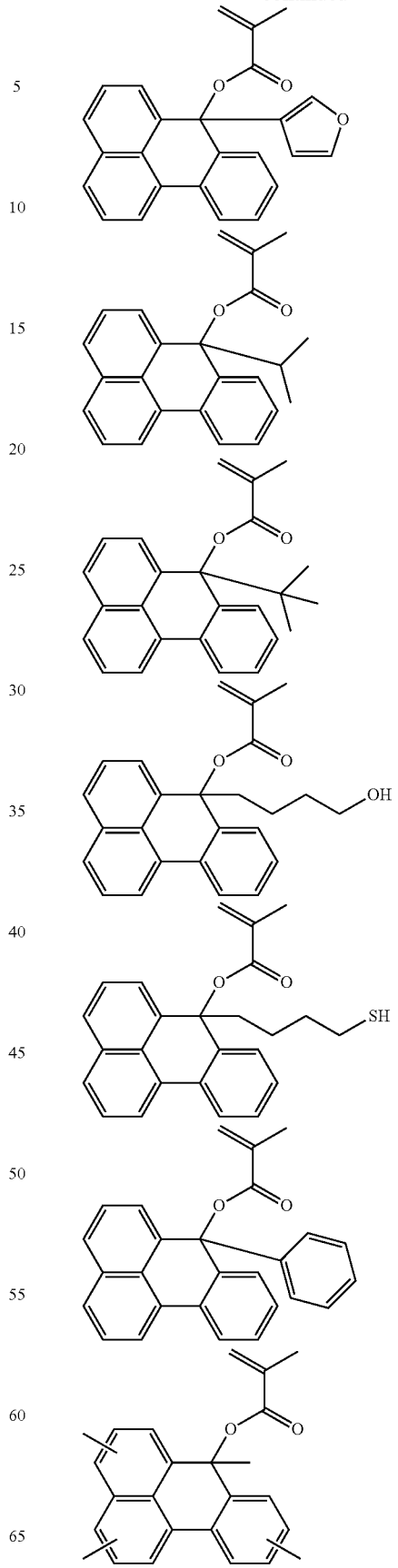

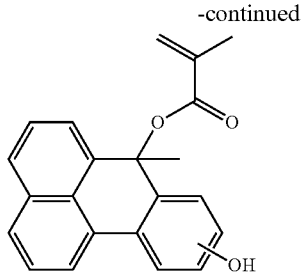
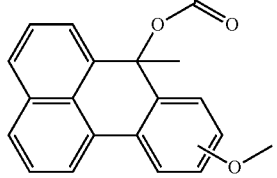
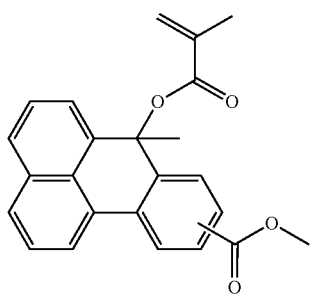
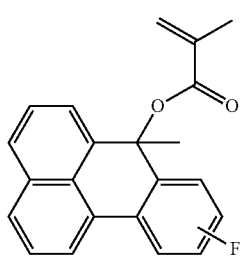
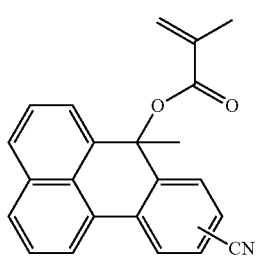
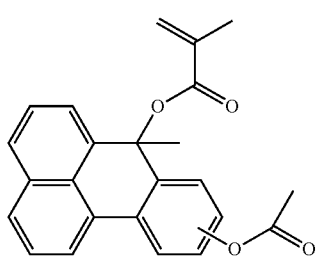

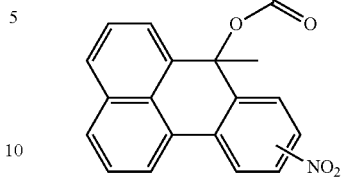

In the recurring unit (b1), the hydrogen atom of the carboxyl group may be substituted by an acid labile group having the general formula (A-3)-27.

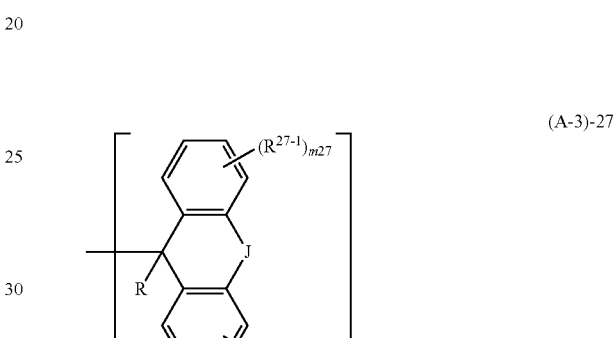

(A-3)-27

Herein $R^{27-1}$ and $R^{27-2}$ each are hydrogen, $C_1$-$C_4$ alkyl, alkoxy, alkanoyl, alkoxycarbonyl, hydroxyl, $C_6$-$C_{10}$ aryl, halogen, or cyano group; R is as defined above; J is methylene, ethylene, vinylene or —$CH_2$—S—; and m27 and n27 each are an integer of 1 to 4.

Examples of the monomer having a carboxyl group substituted with an acid labile group of formula (A-3)-27 are given below.

81
-continued
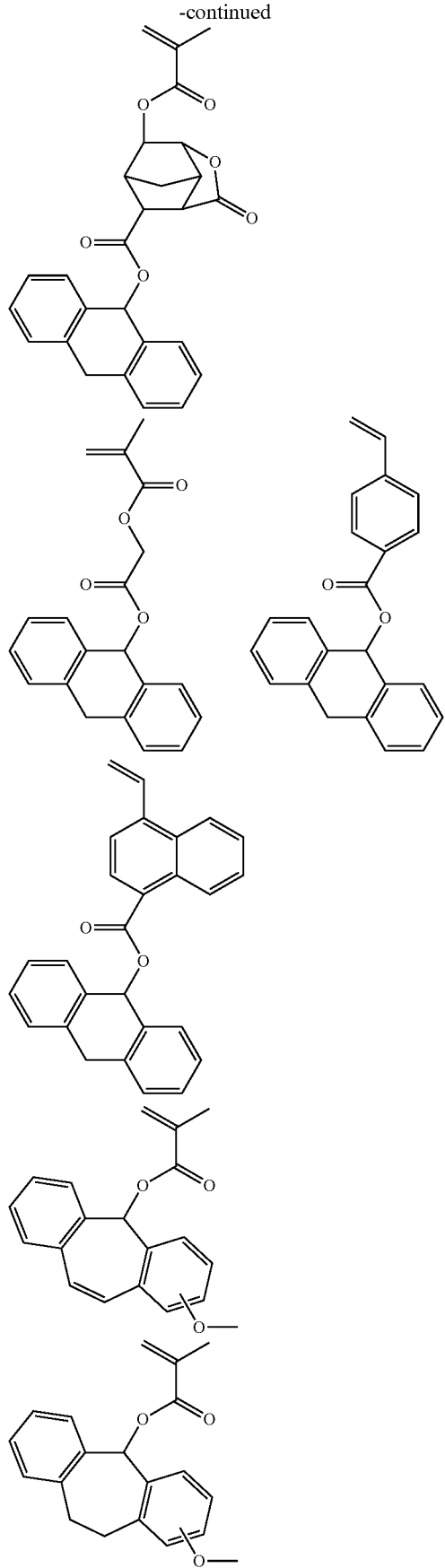
82
-continued
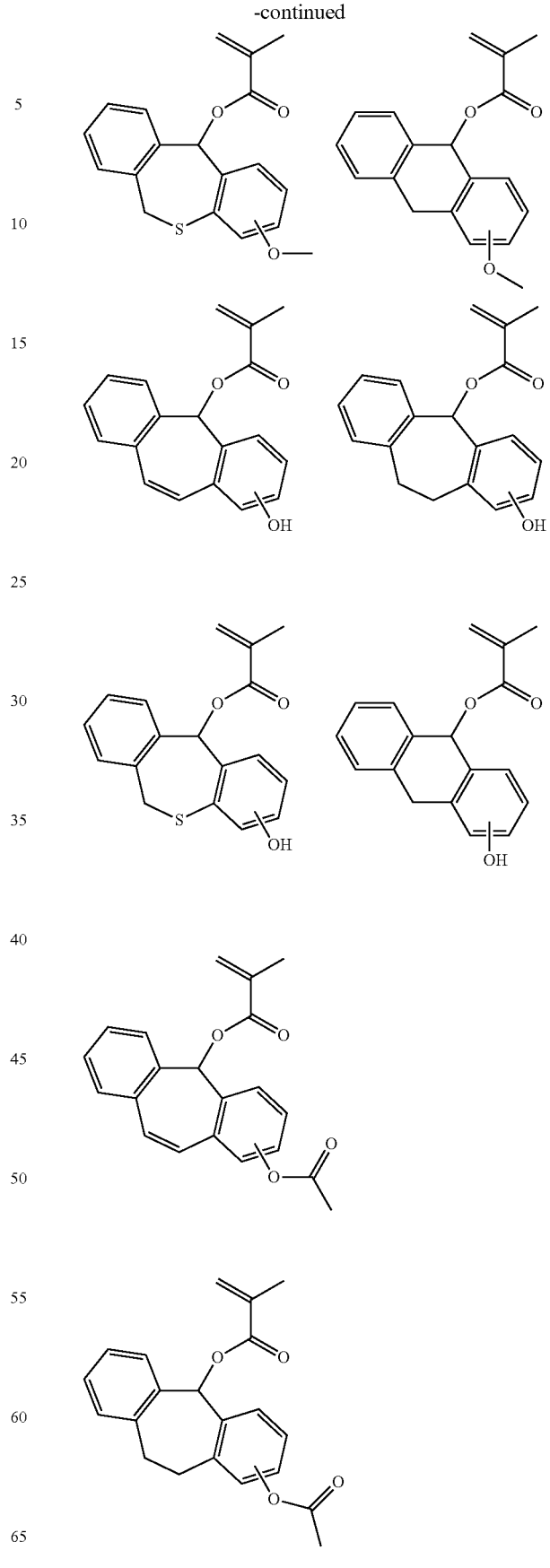

-continued
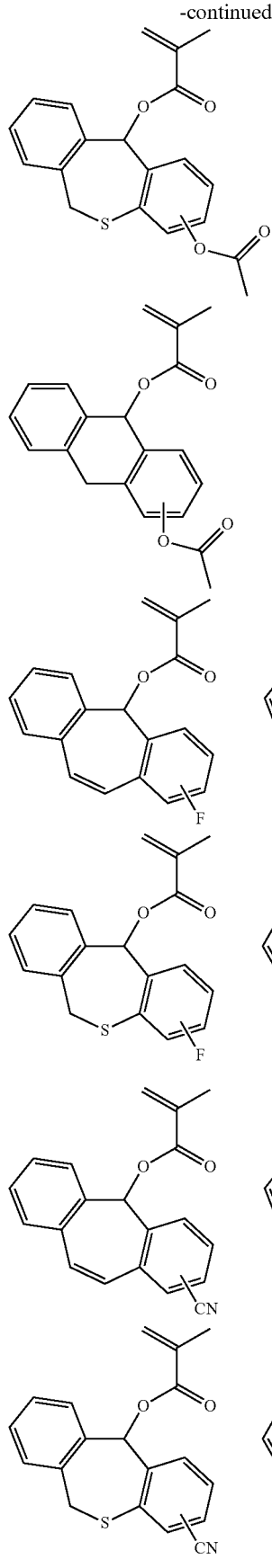
-continued
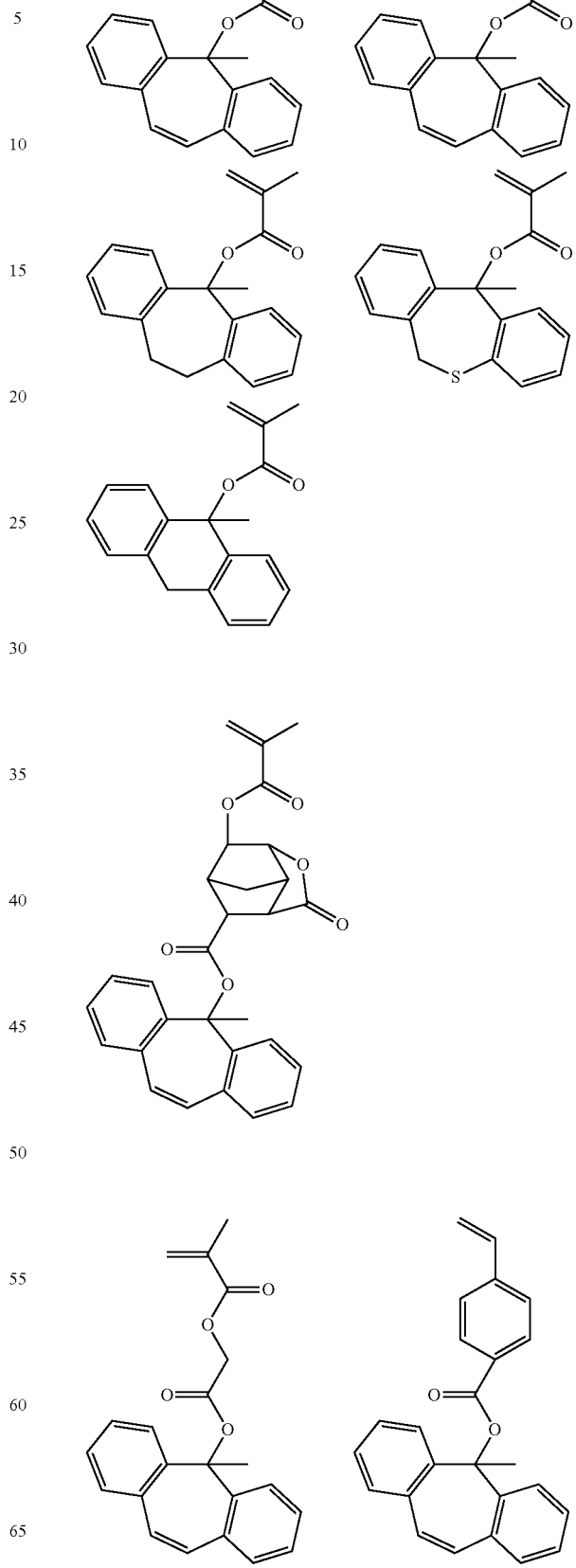

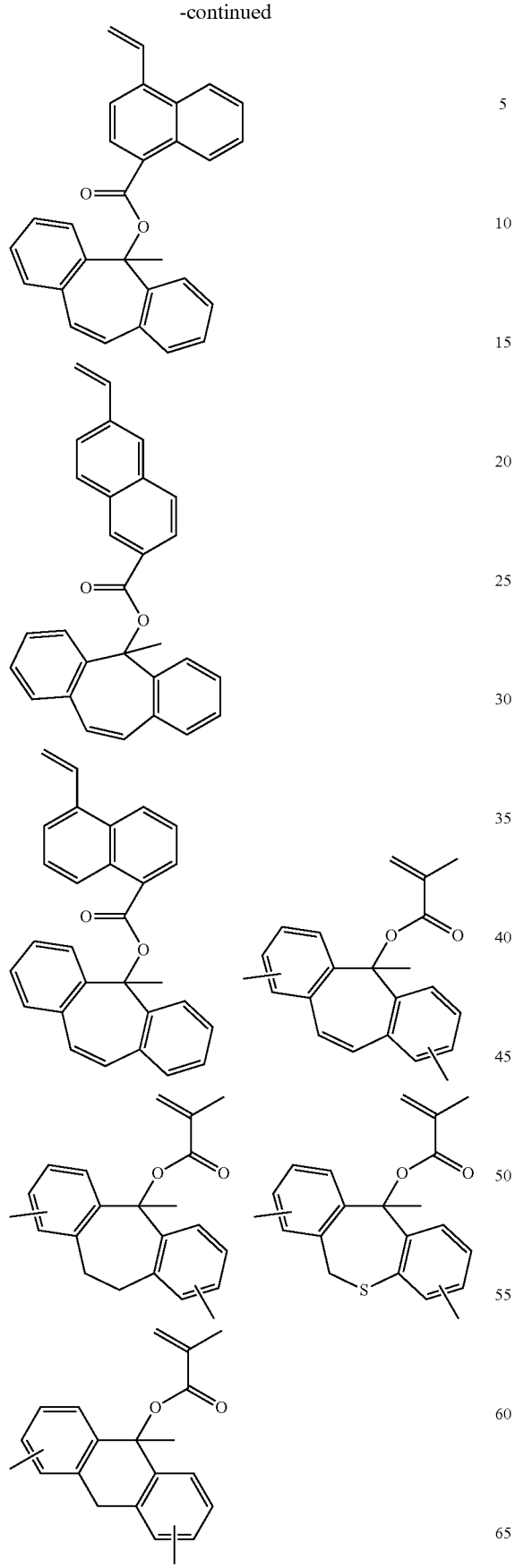
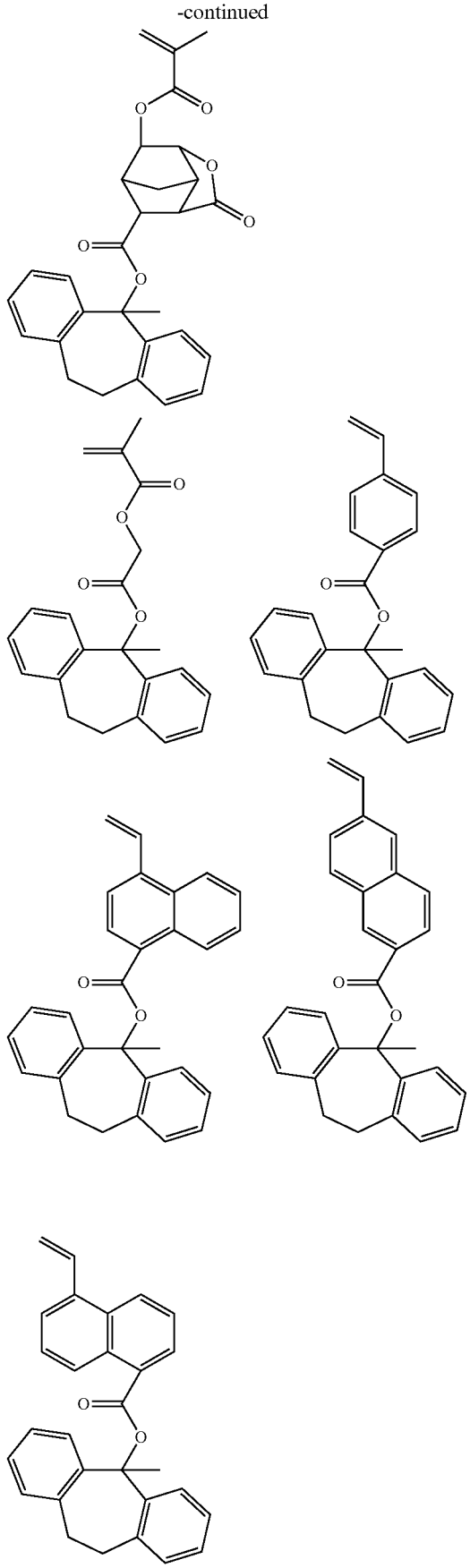

-continued
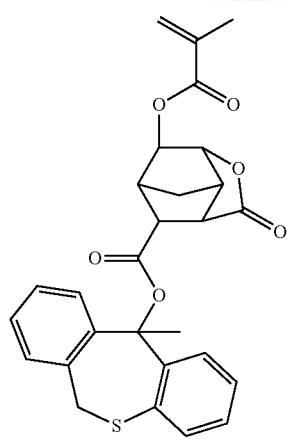
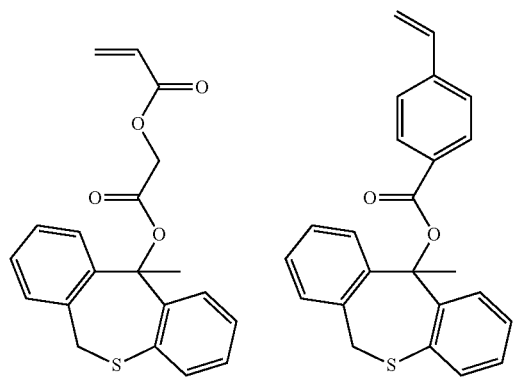
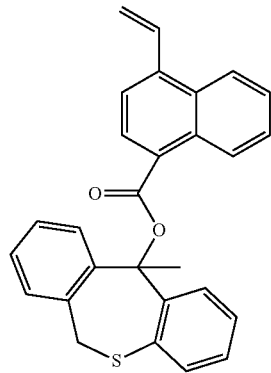
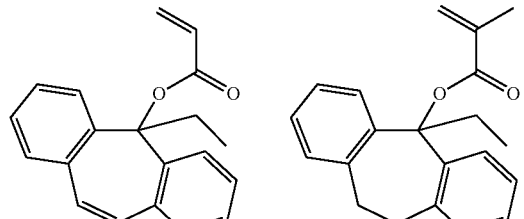
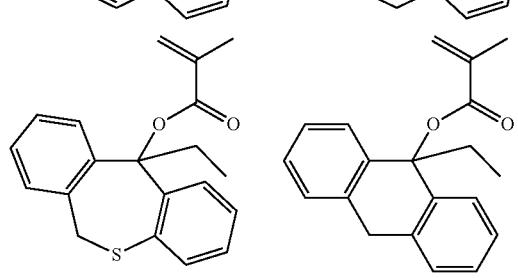
-continued
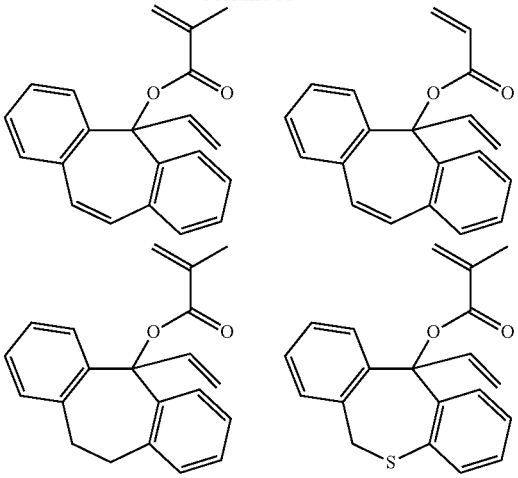
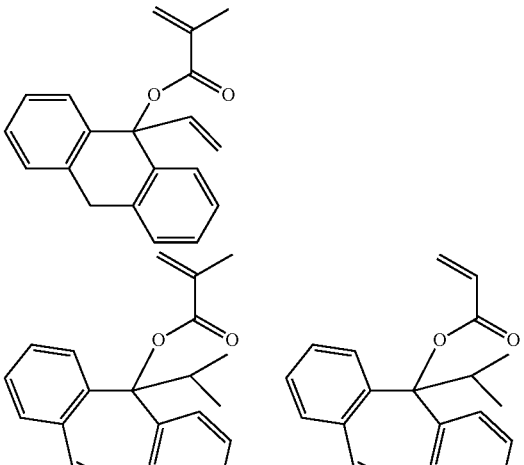
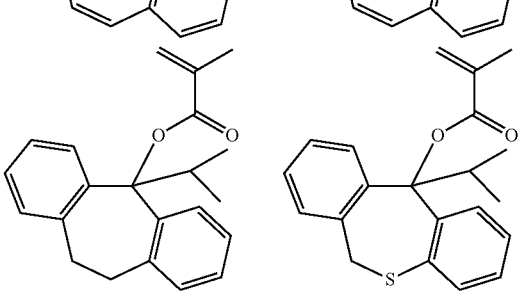
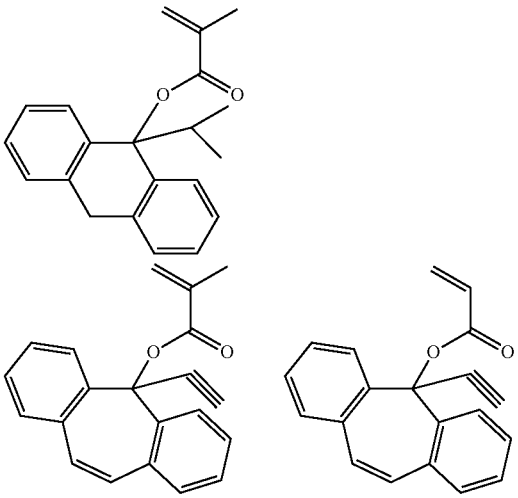

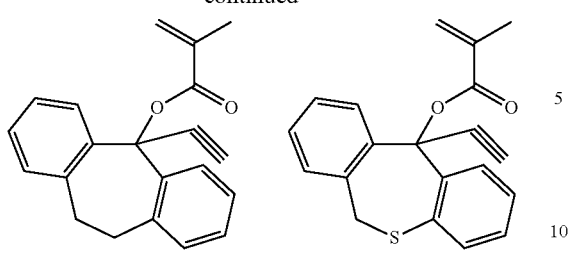

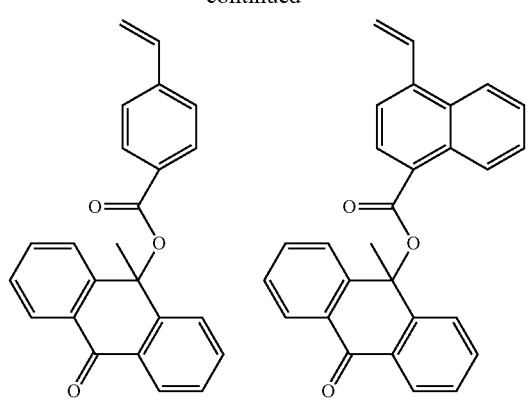

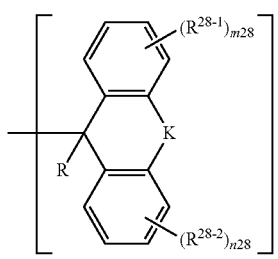

In the recurring unit (b1), the hydrogen atom of the carboxyl group may be substituted by an acid labile group having the general formula (A-3)-28.

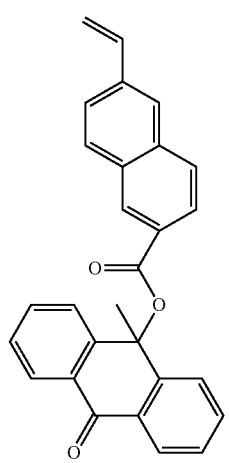

(A-3)-28

Herein $R^{28-1}$ and $R^{28-2}$ each are hydrogen, $C_1$-$C_4$ alkyl, alkoxy, alkanoyl, alkoxycarbonyl, hydroxyl, $C_6$-$C_{10}$ aryl, halogen, or cyano group; R is as defined above; K is carbonyl, ether, sulfide, —S(=O)— or —S(=O)$_2$—; and m28 and n28 each are an integer of 1 to 4.

Examples of the monomer having a carboxyl group substituted with an acid labile group of formula (A-3)-28 are given below.

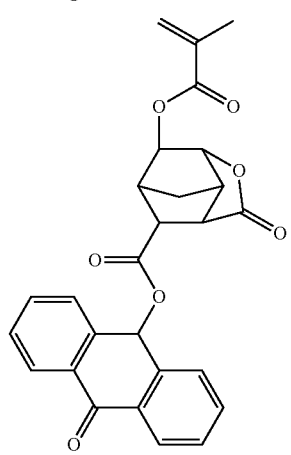

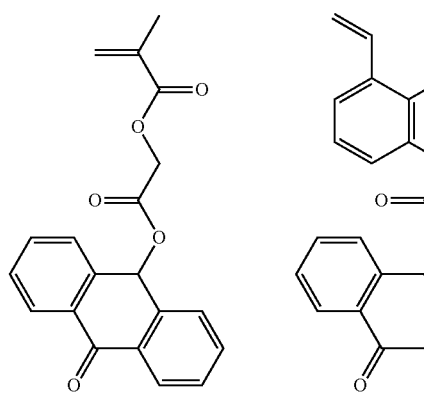

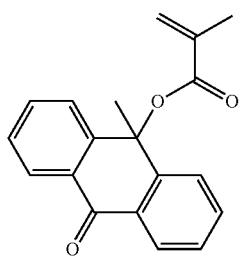 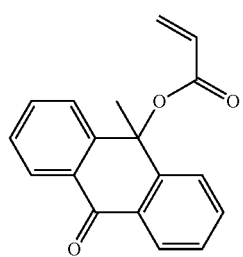 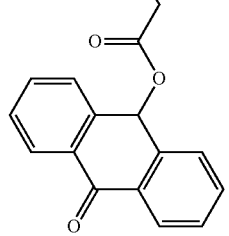

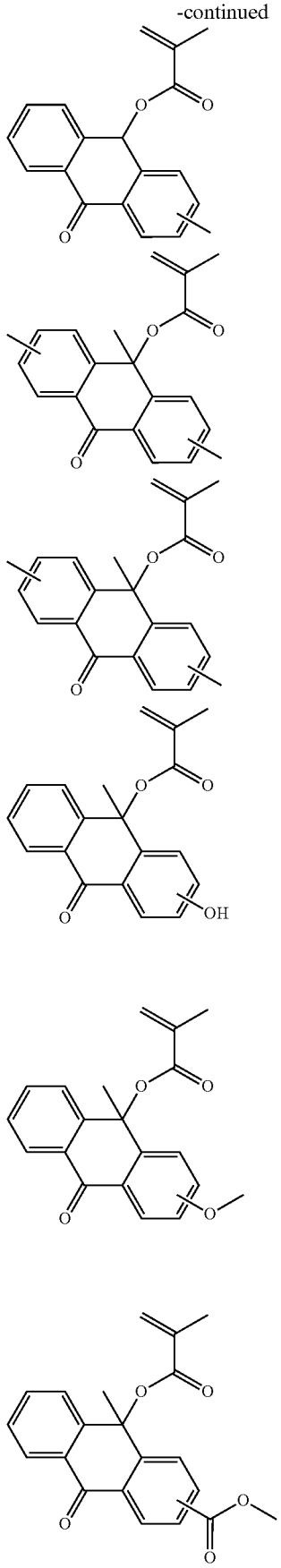
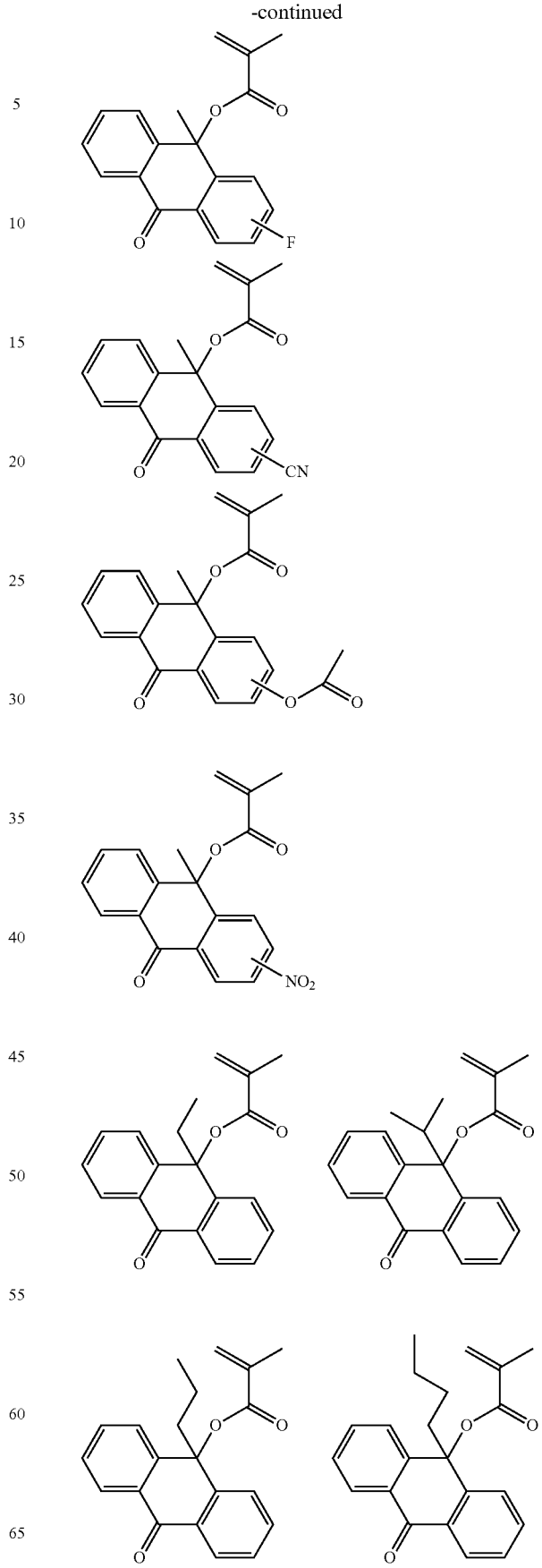

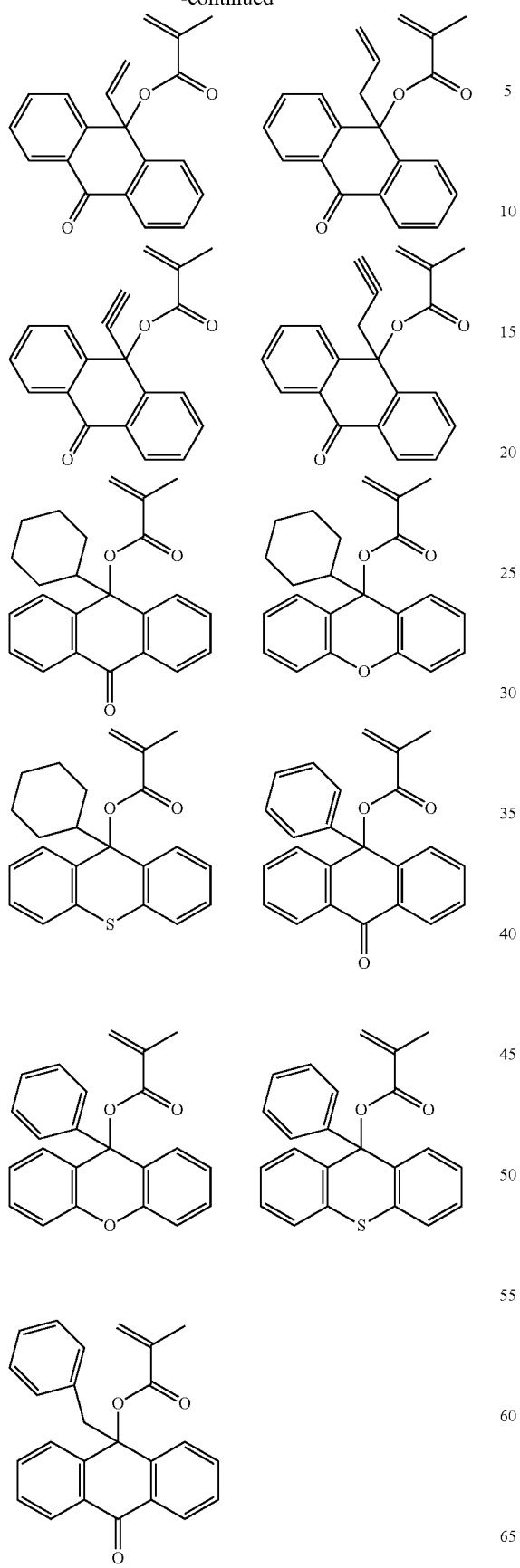
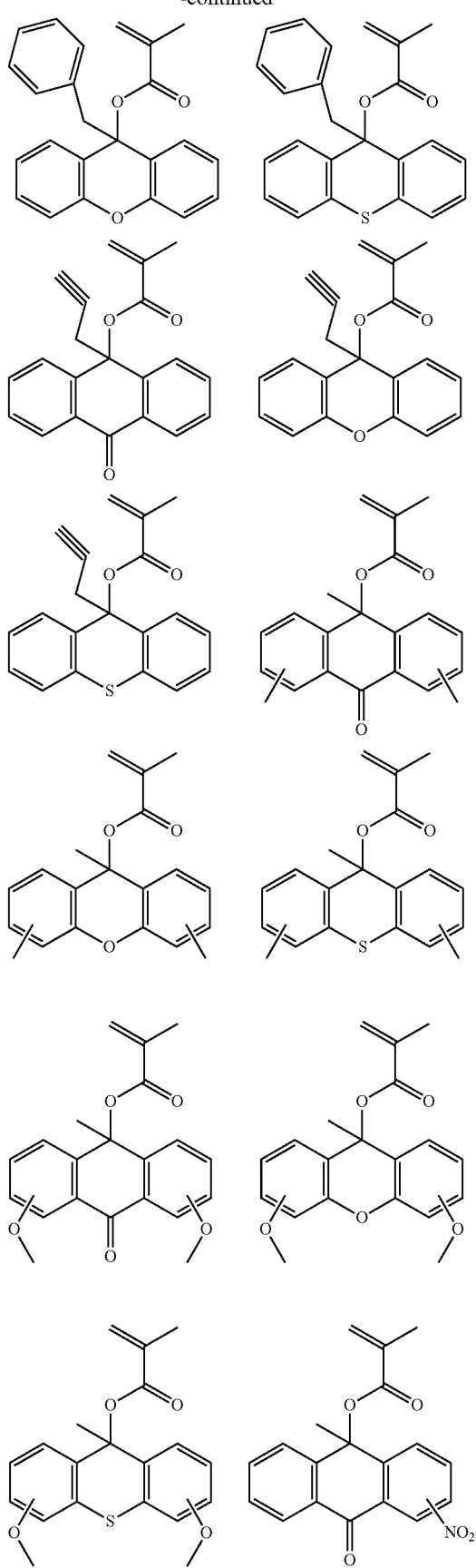

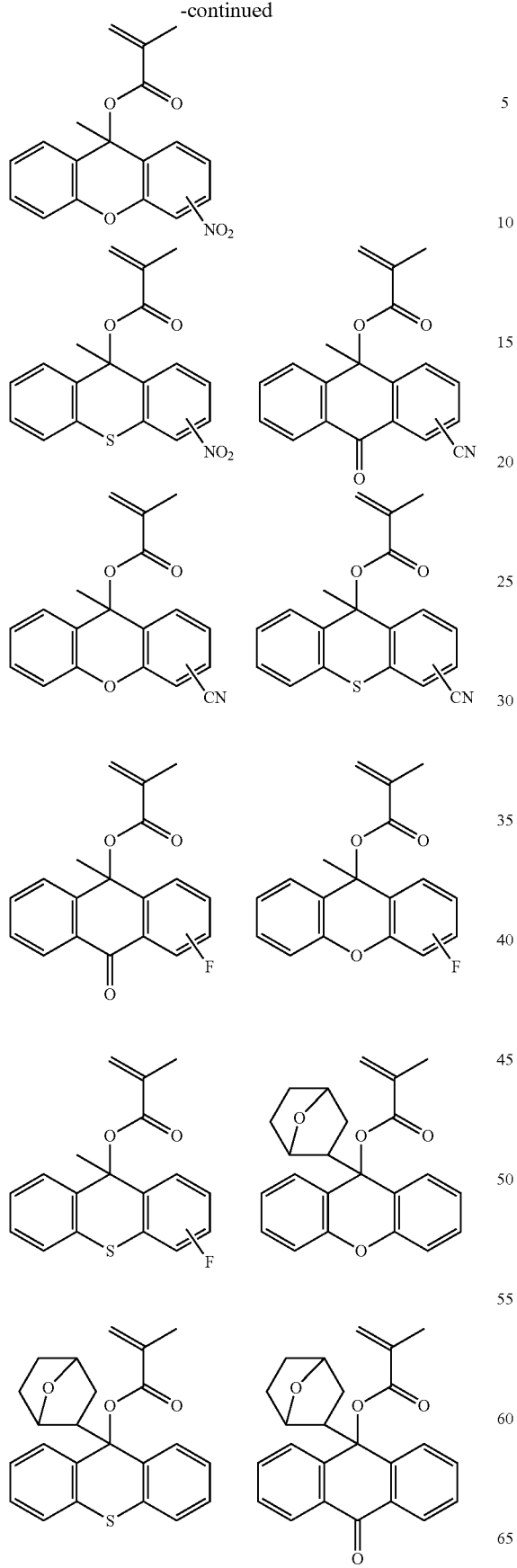
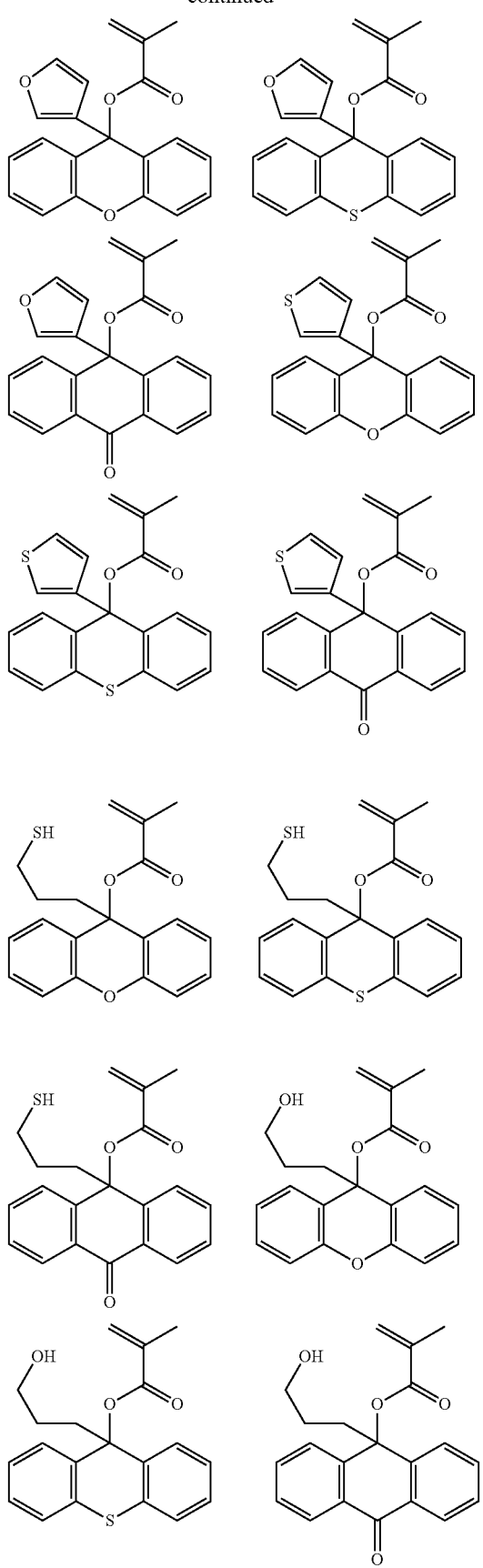

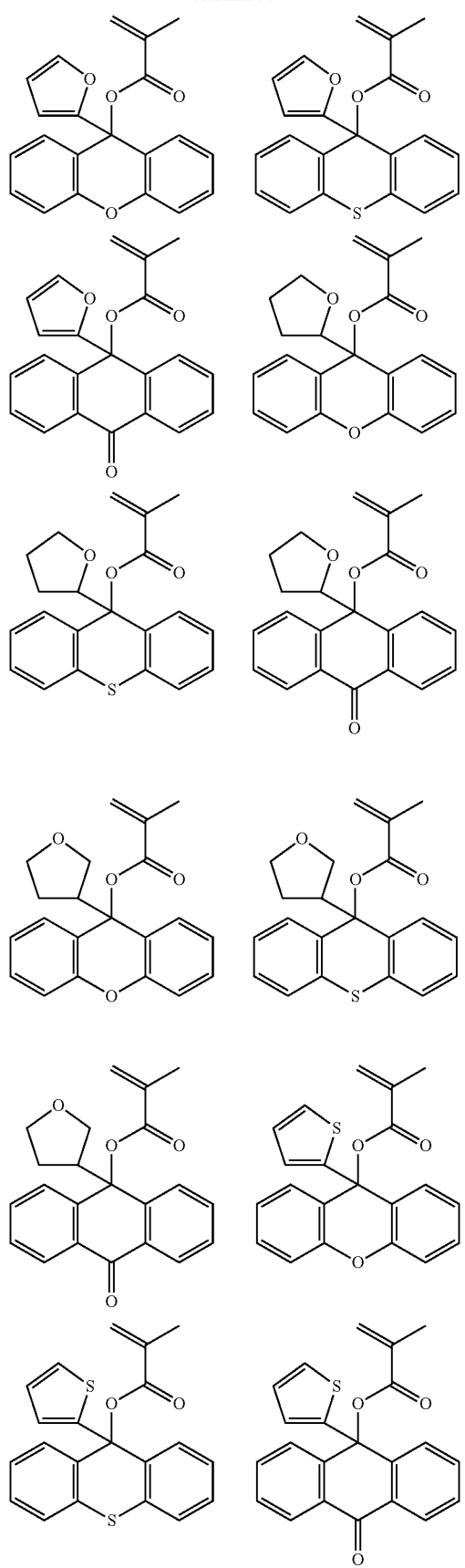
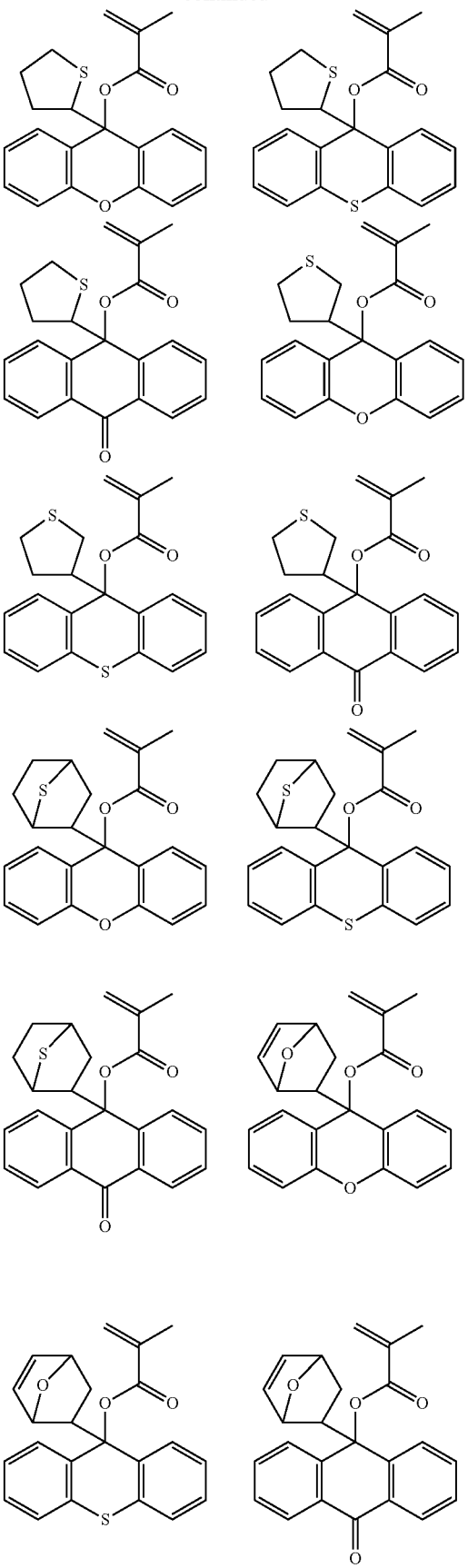

99
-continued
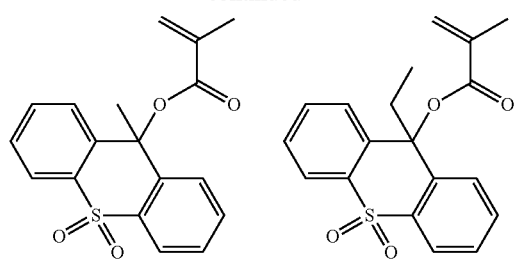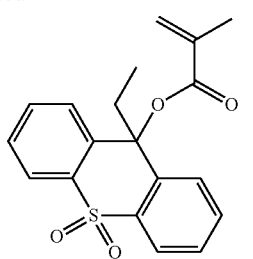
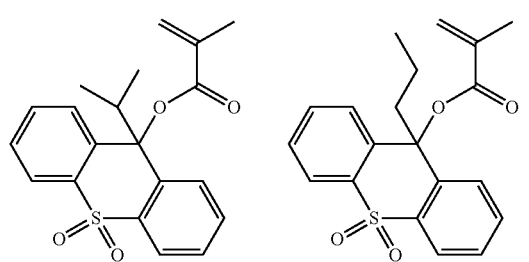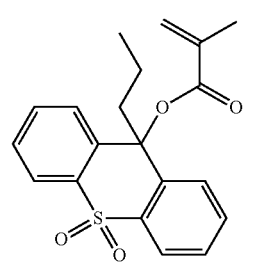
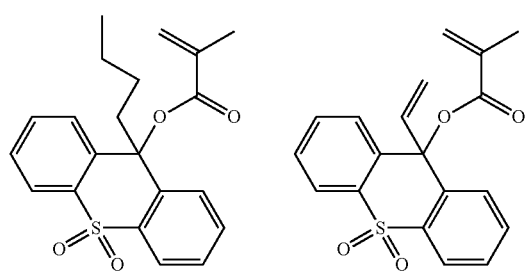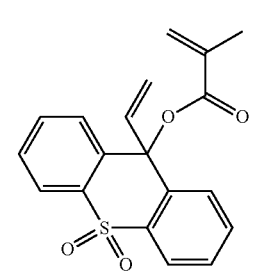
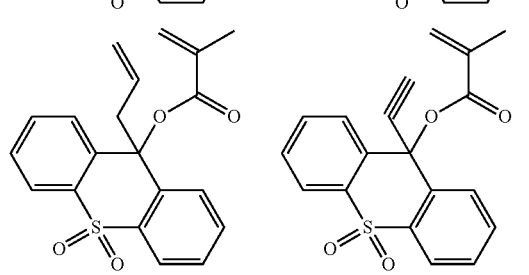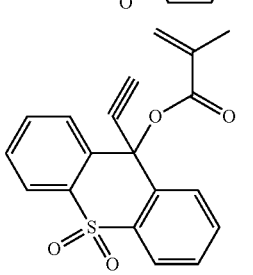
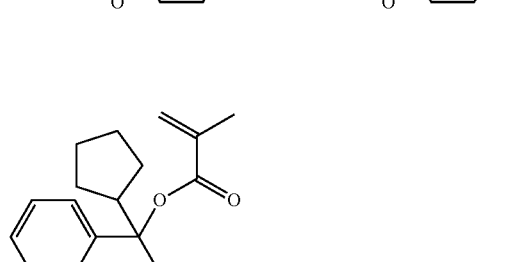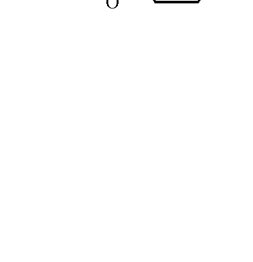
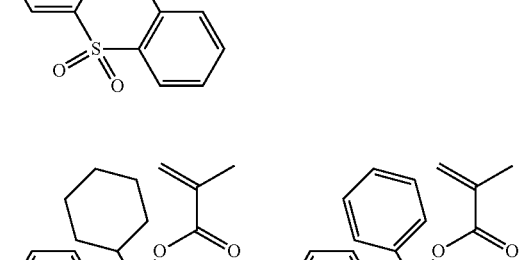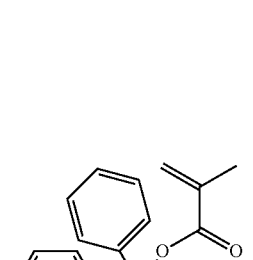
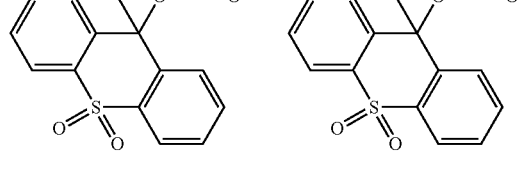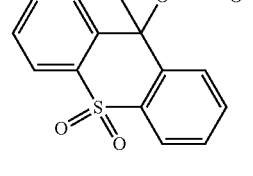
100
-continued
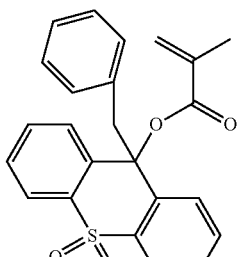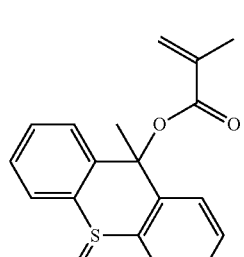
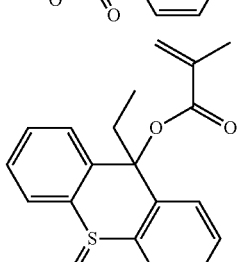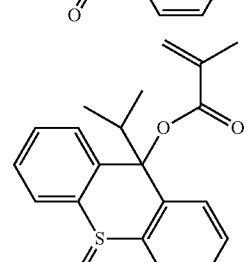
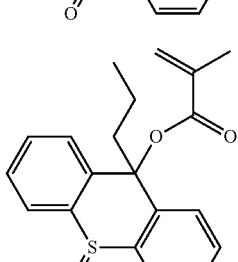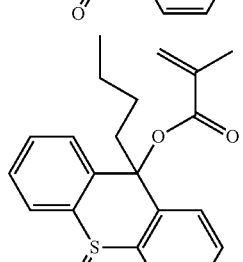
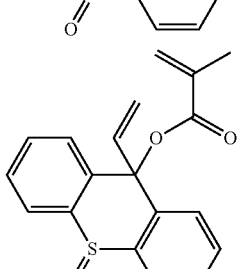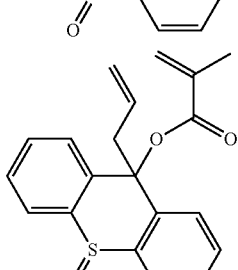
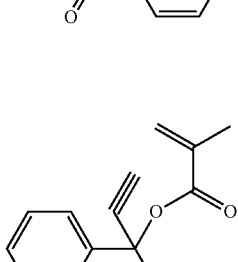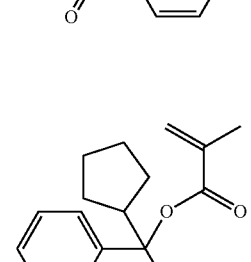
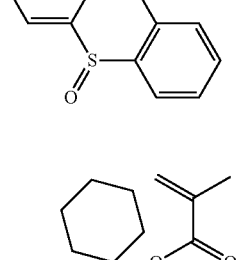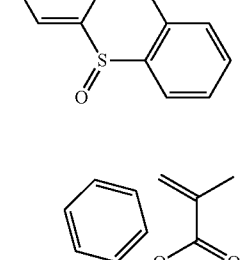
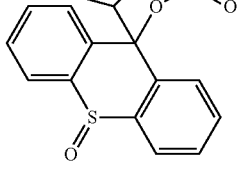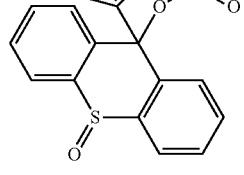

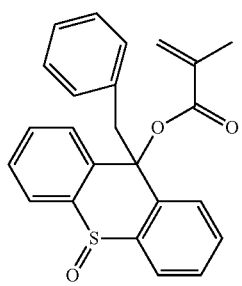

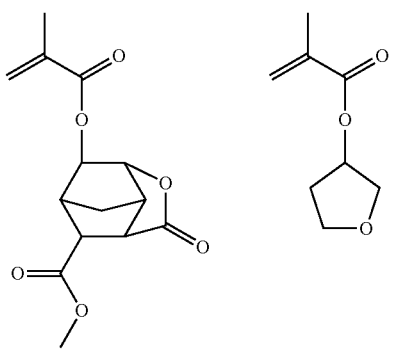

In a more preferred embodiment, the copolymer as the base resin may further comprise recurring units (c) having an adhesive group as copolymerized with the recurring units (a) and the recurring units (b1) having a carboxyl group substituted with an acid labile group and/or the recurring units (b2) having a phenolic hydroxyl group substituted with an acid labile group, as represented by formula (2). The adhesive group is selected from among hydroxyl (exclusive of hydroxyl in formula (1)), carboxyl, lactone ring, carbonate, thiocarbonate, carbonyl, cyclic acetal, ether, ester, sulfonic acid ester, cyano, amide, and —O—C(=O)-G- wherein G is sulfur or NH; and c is a number in the range: $0 < c \leq 0.9$ and $0.2 \leq a+b1+b2+c \leq 1.0$. The copolymer has a weight average molecular weight in the range of 1,000 to 500,000.

Shown below are examples of the monomer from which the recurring units (c) having an adhesive group selected from among hydroxyl (exclusive of hydroxyl in formula (1)), carboxyl, lactone ring, carbonate, thiocarbonate, carbonyl, cyclic acetal, ether, ester, sulfonic acid ester, cyano, amide, and —O—C(=O)-G- wherein G is sulfur or NH are derived.

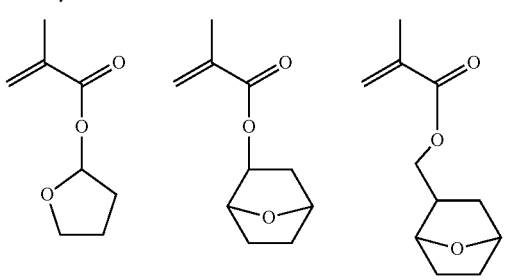

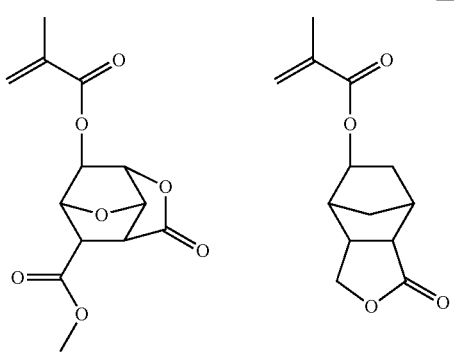

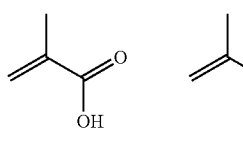

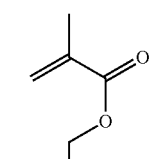

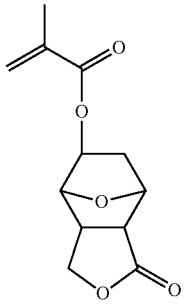

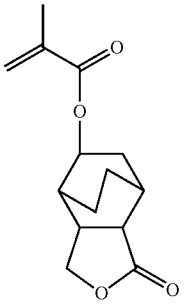

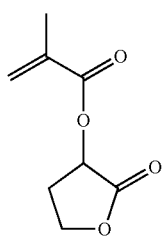

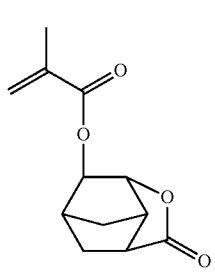

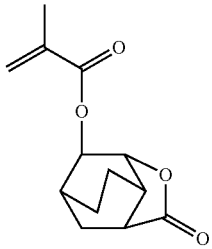

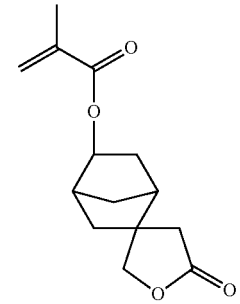

103
-continued
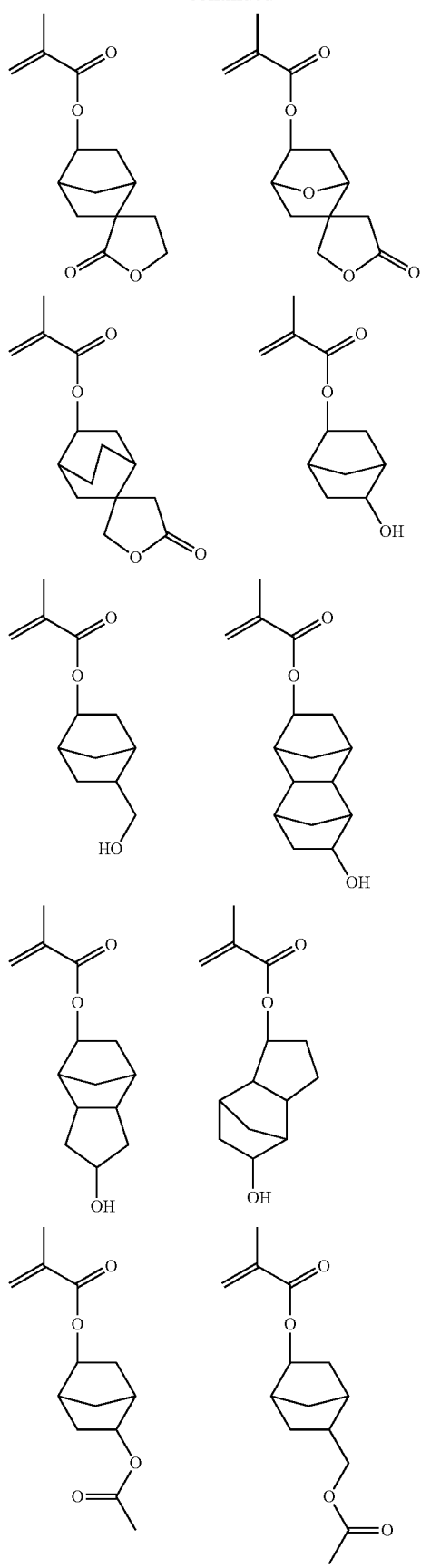
104
-continued
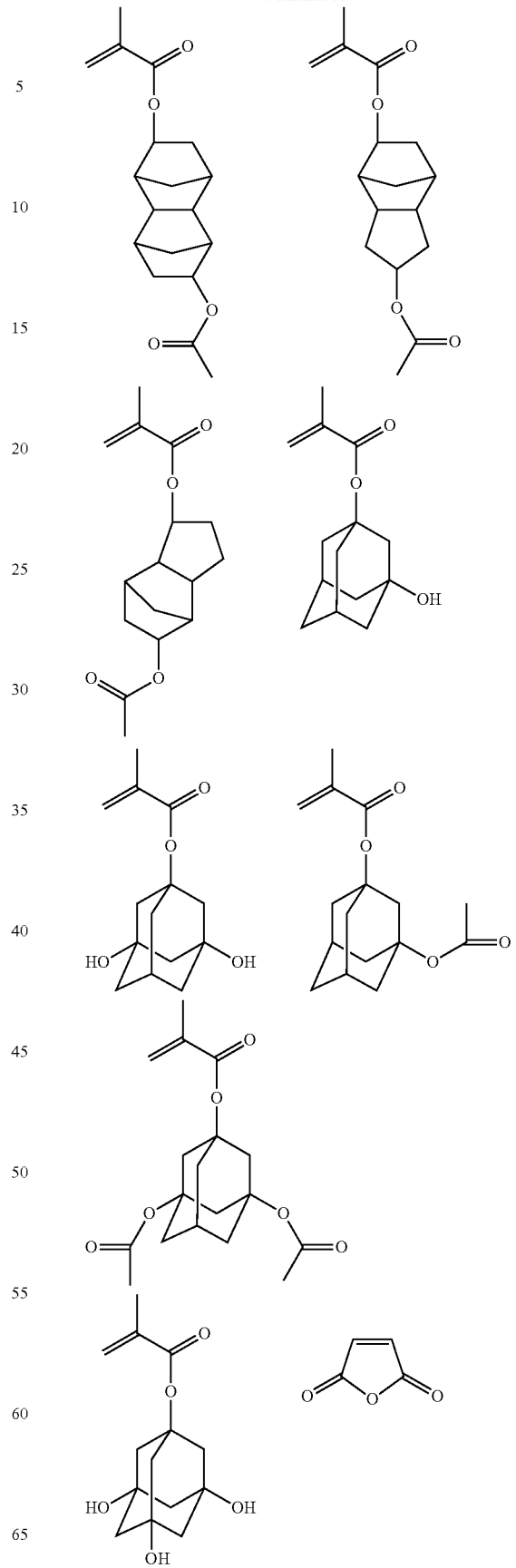

105
-continued
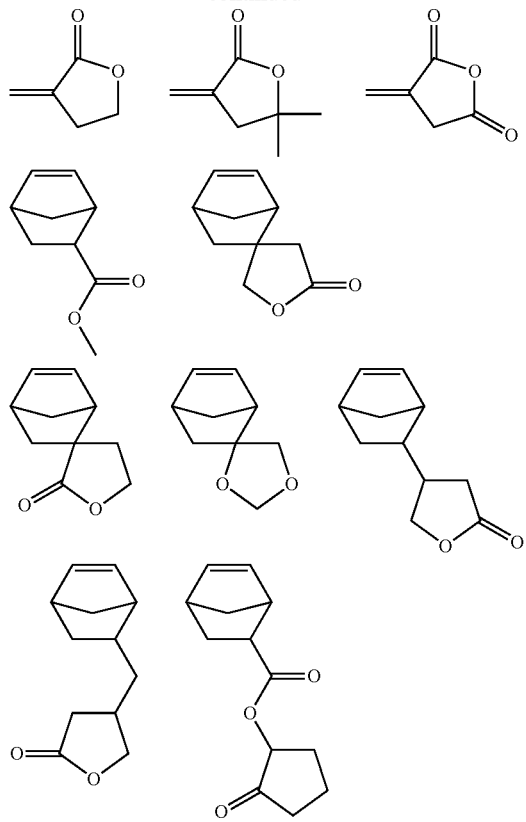
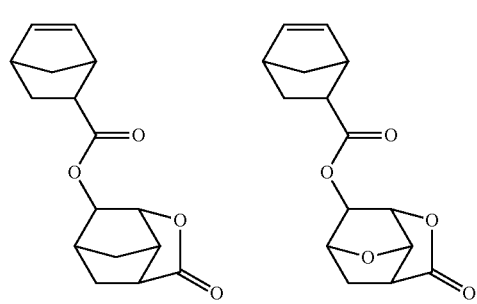
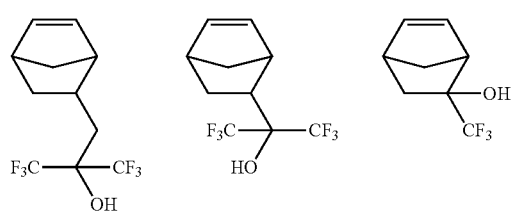
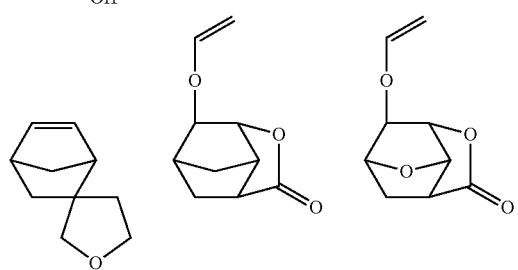
106
-continued
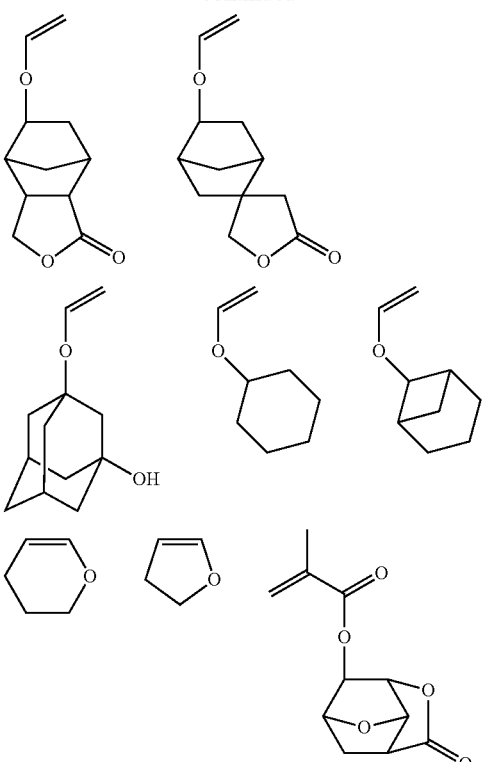
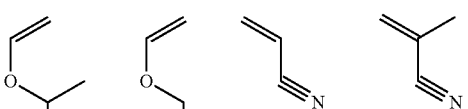
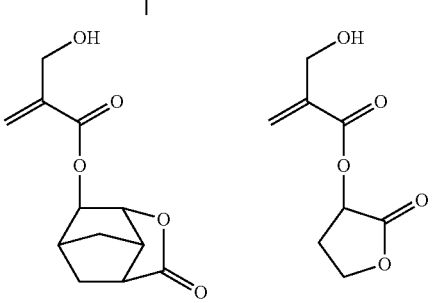

107
-continued
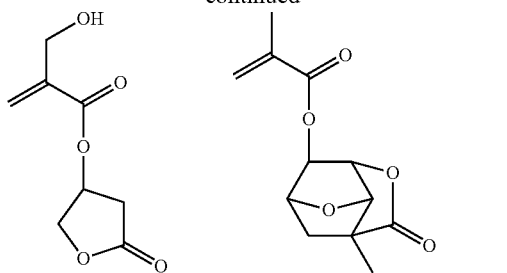
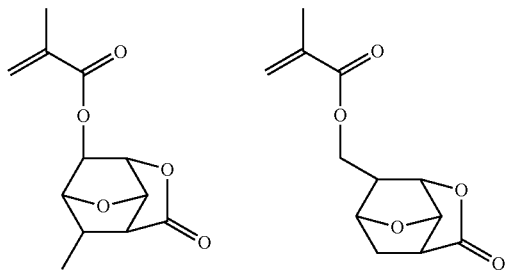
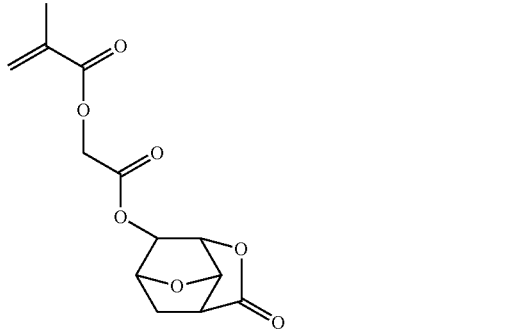
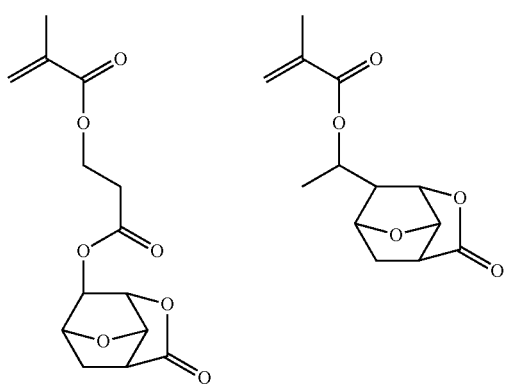
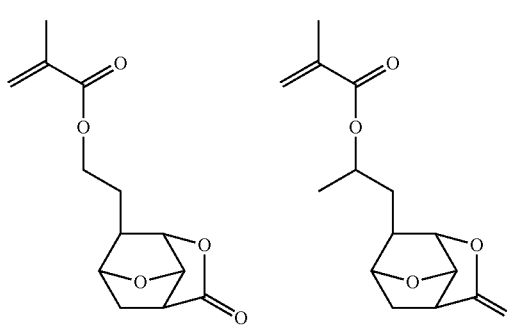
108
-continued
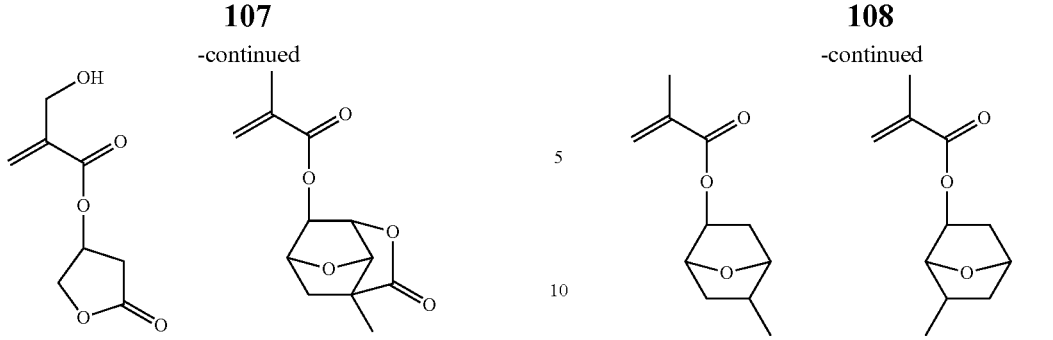
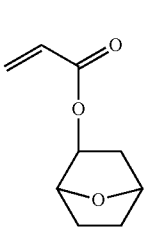
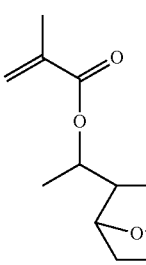
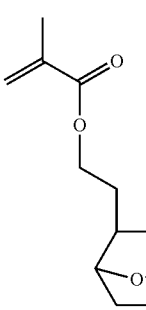
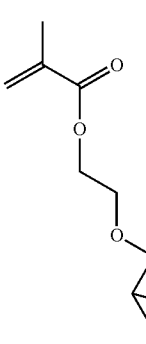

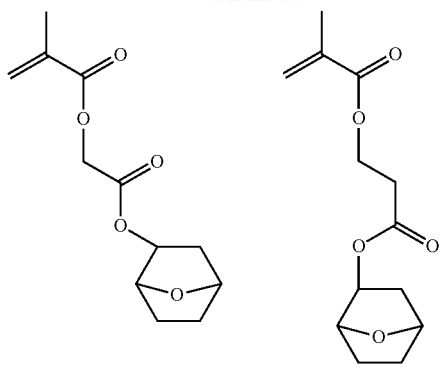
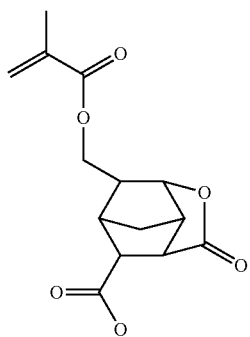
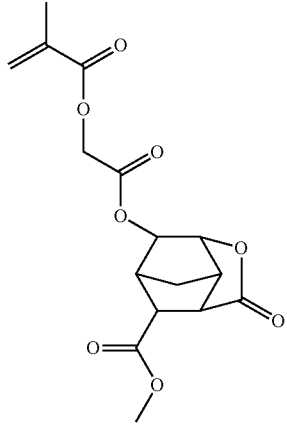
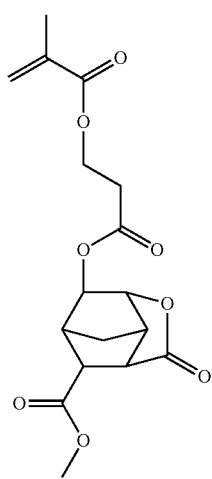
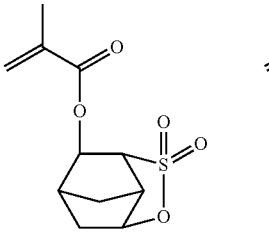
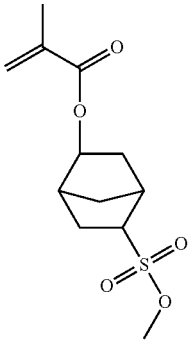
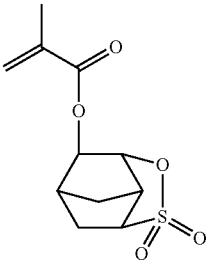
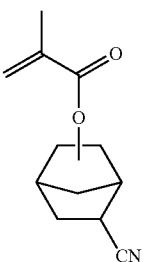
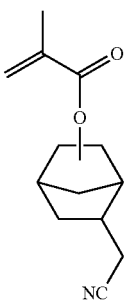
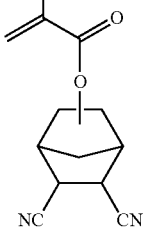
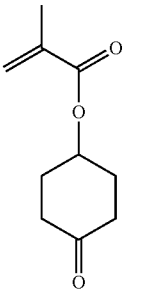
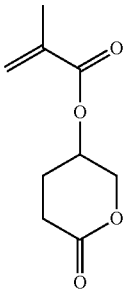
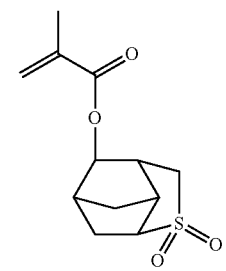
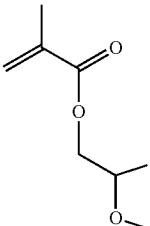
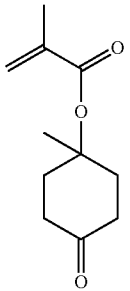

111
-continued
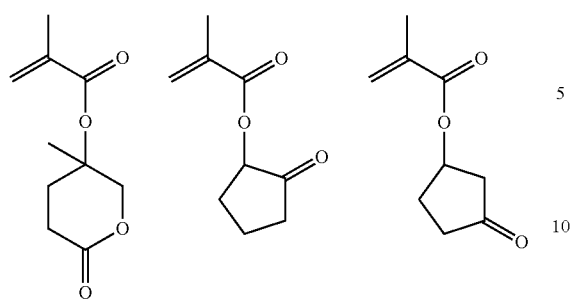
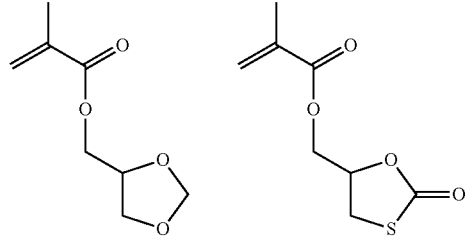
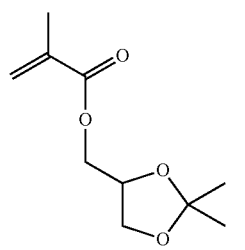
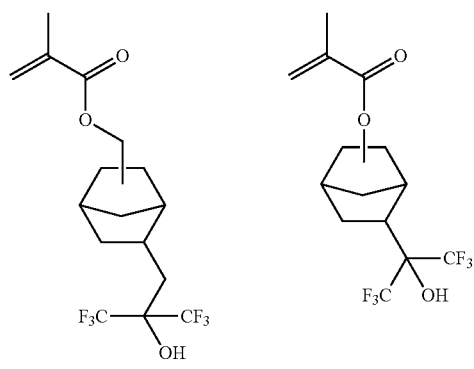
112
-continued
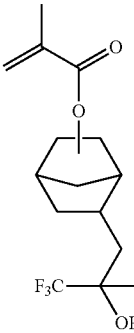
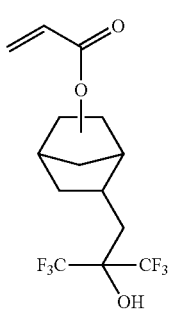
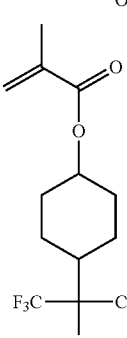
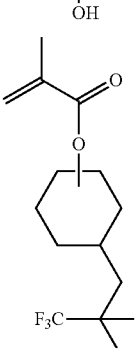
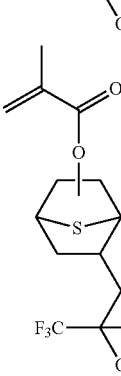
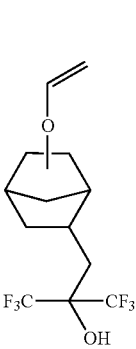
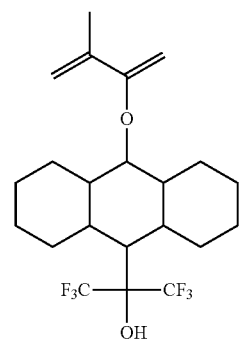

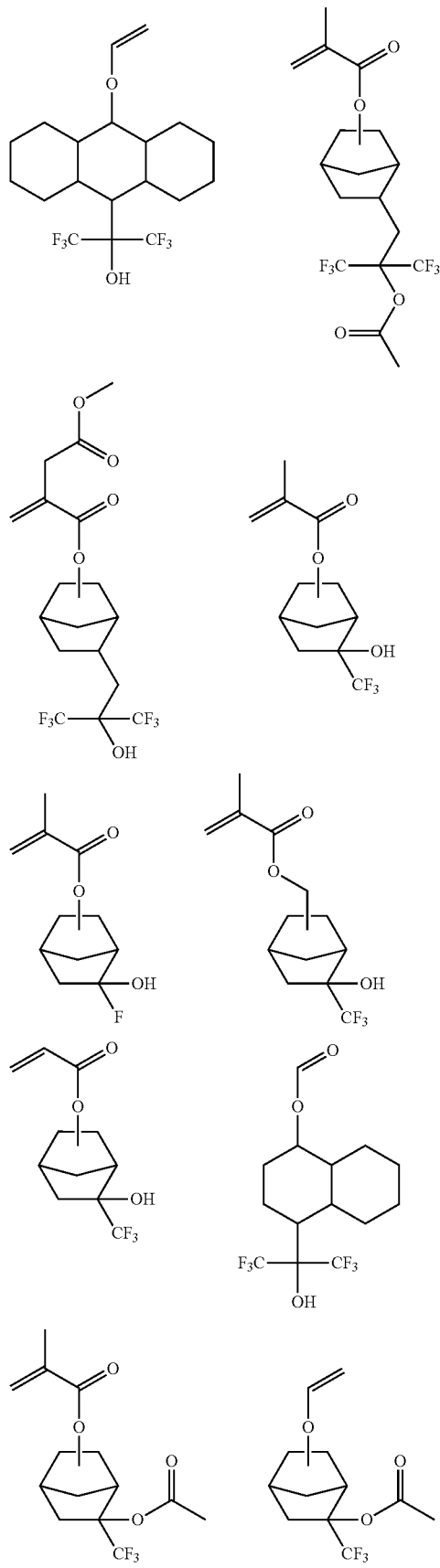

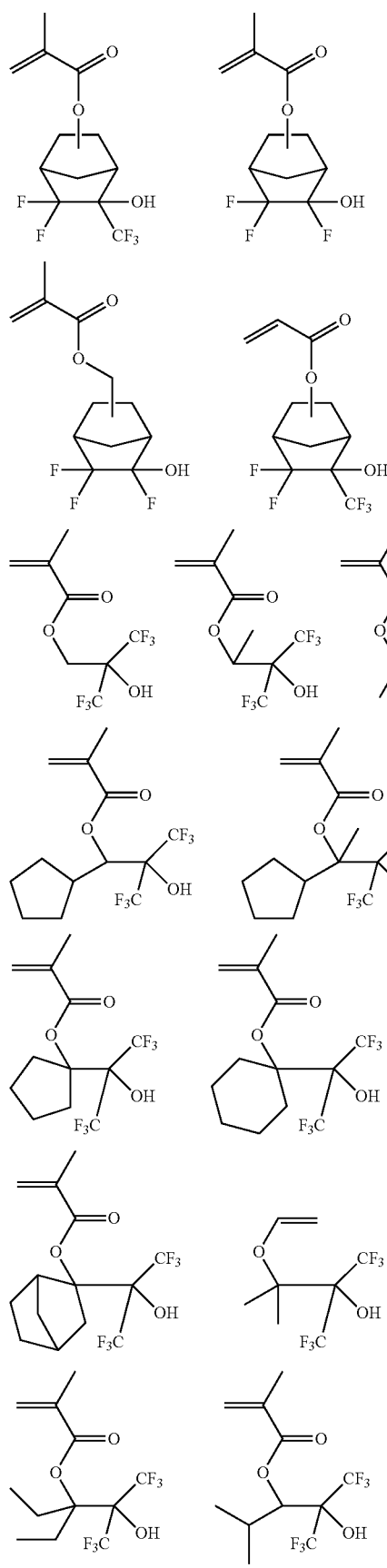
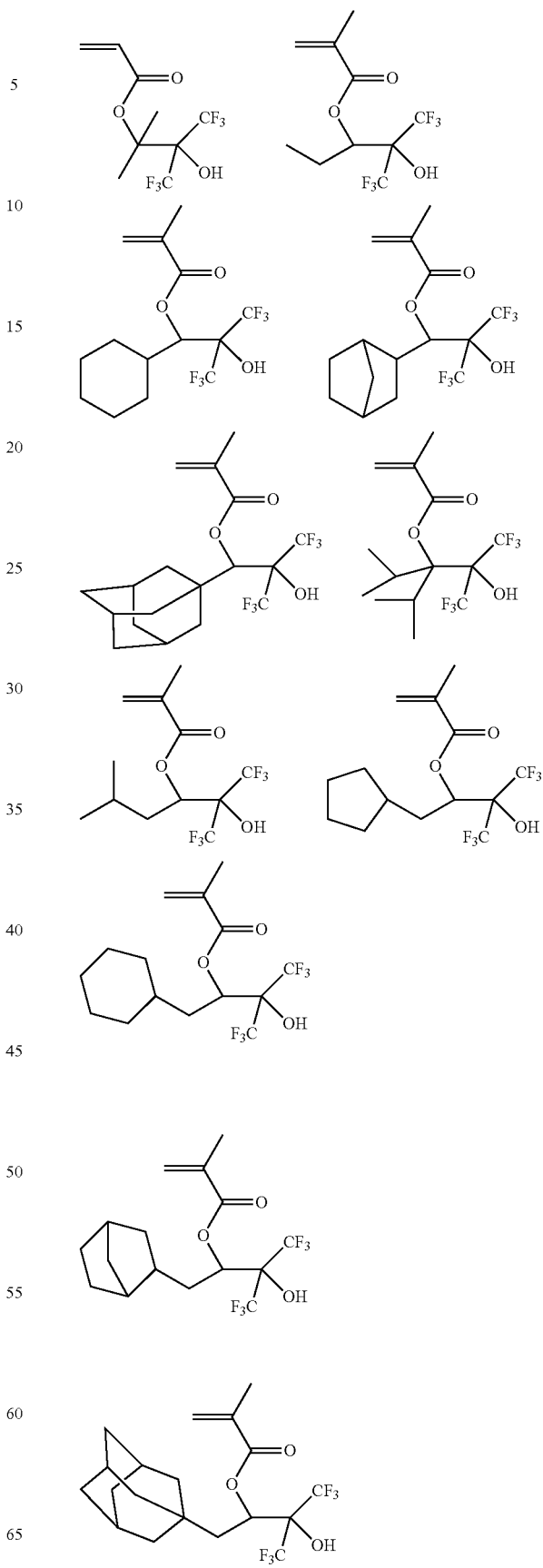

117
-continued
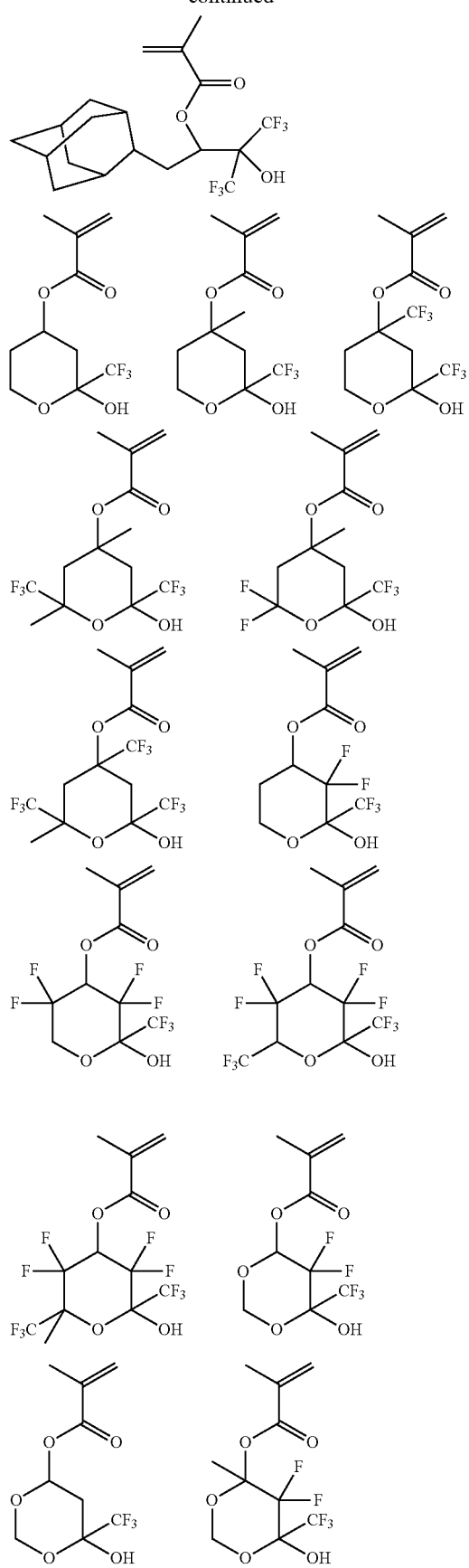
118
-continued
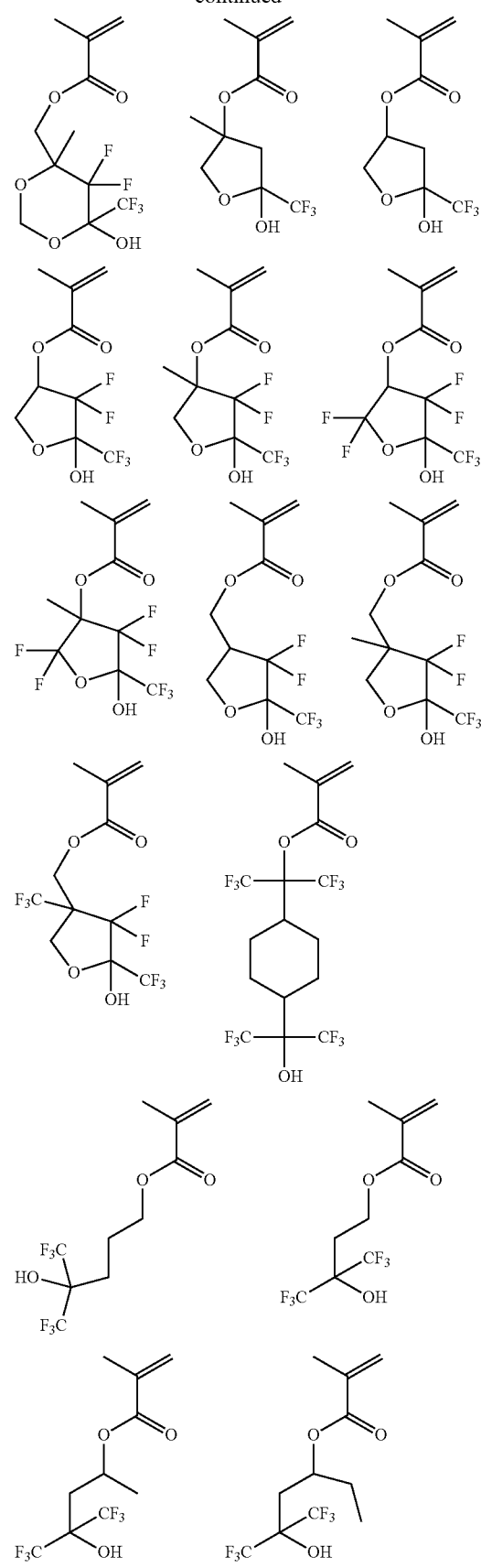

119
-continued
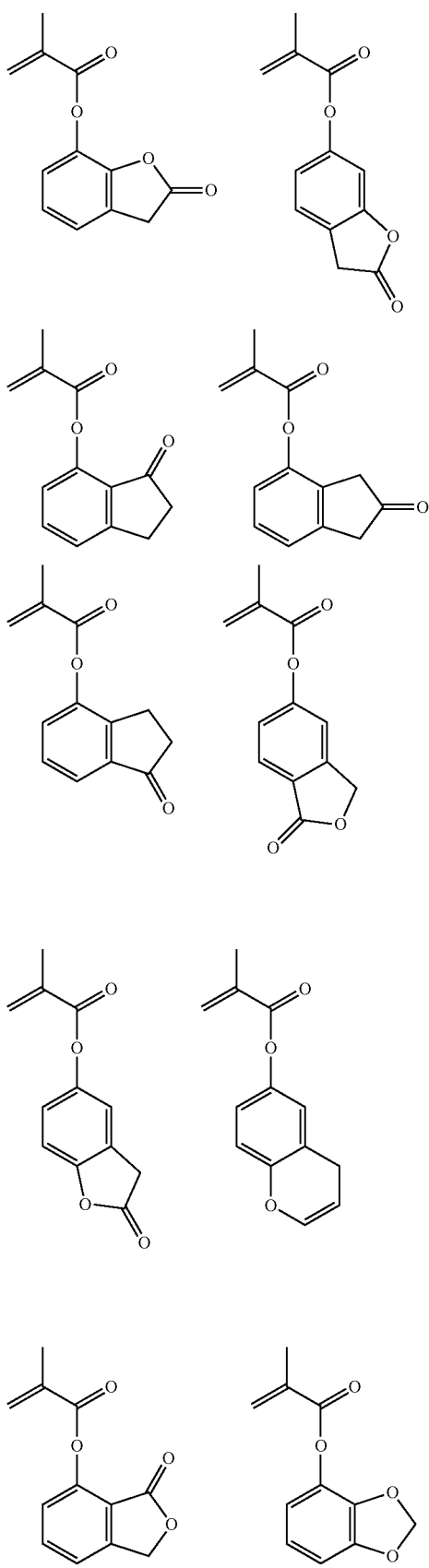
120
-continued
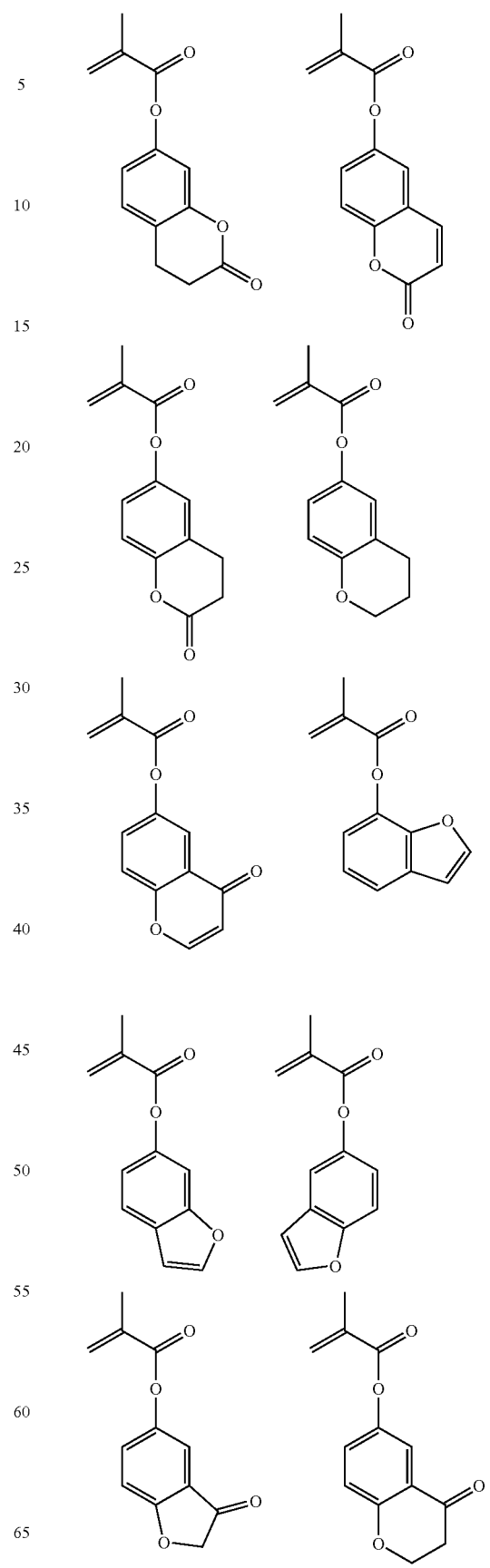

-continued
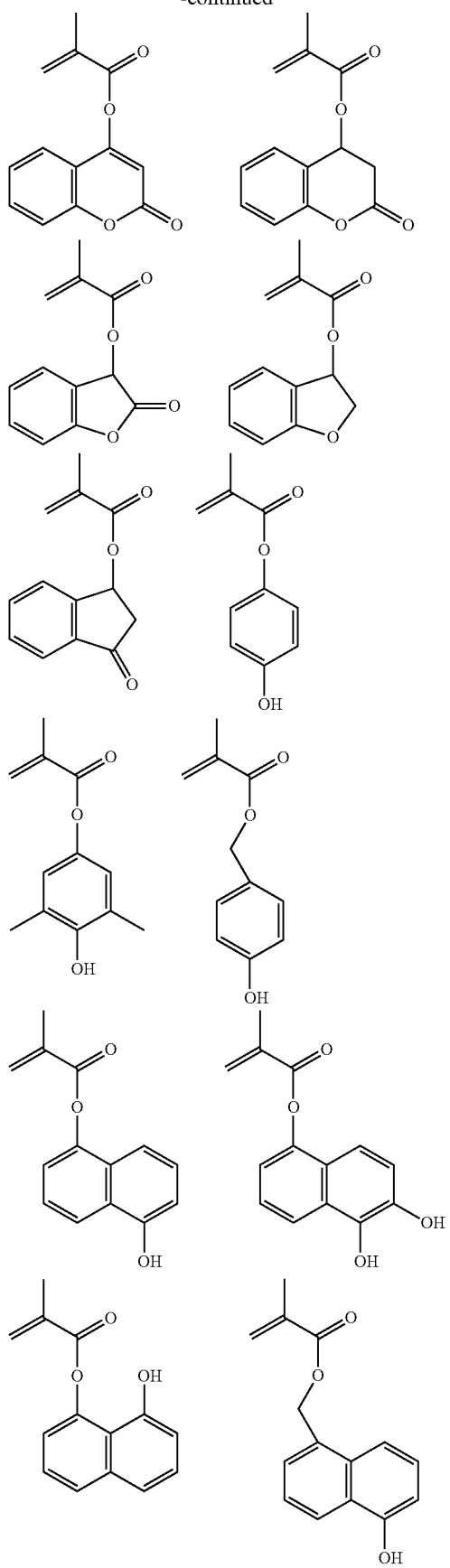
-continued
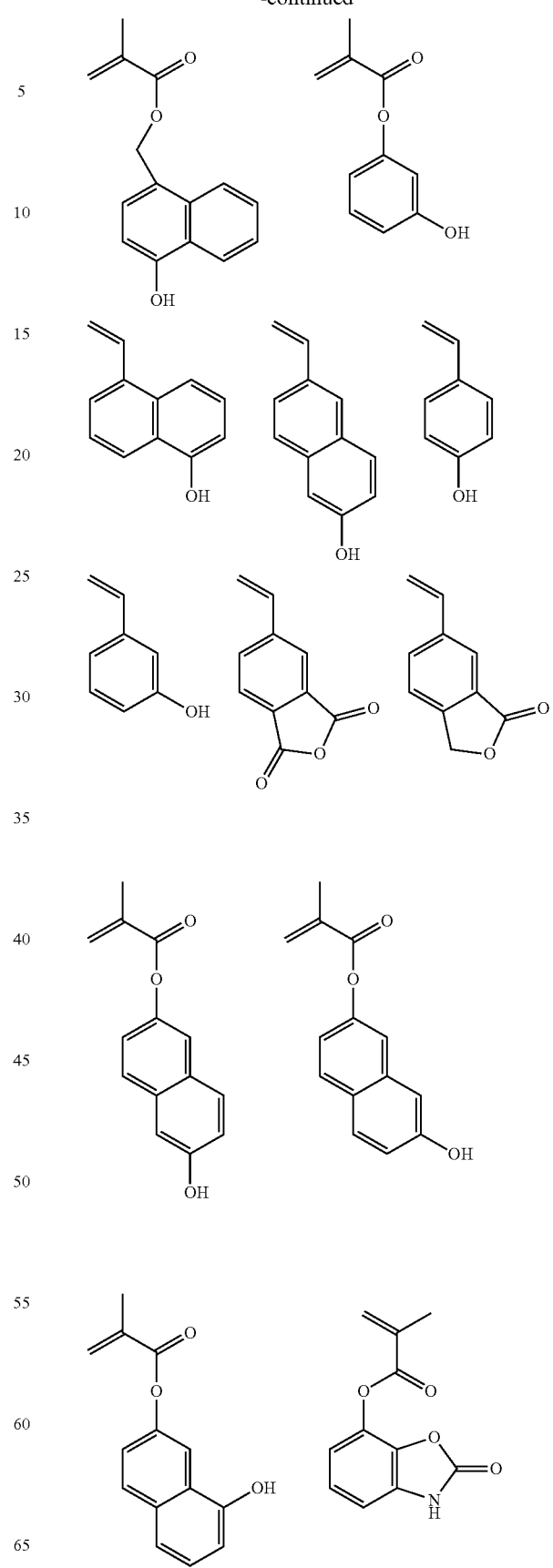

123
-continued
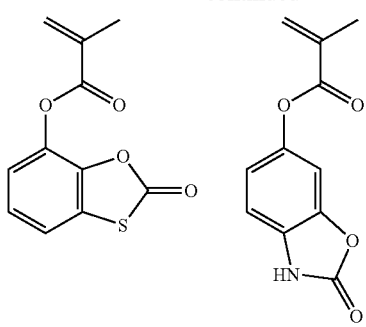
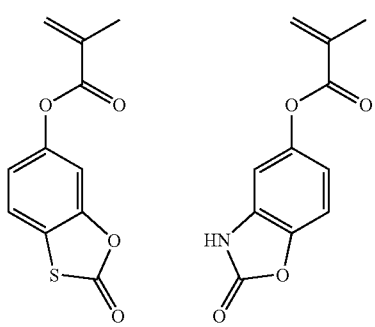
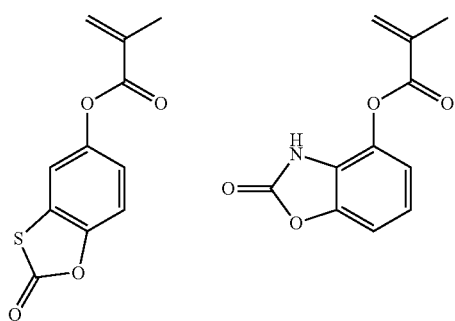
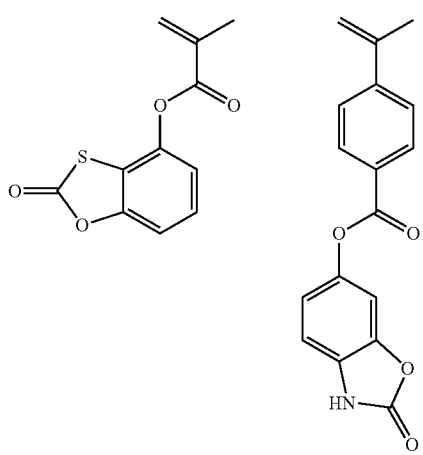
124
-continued
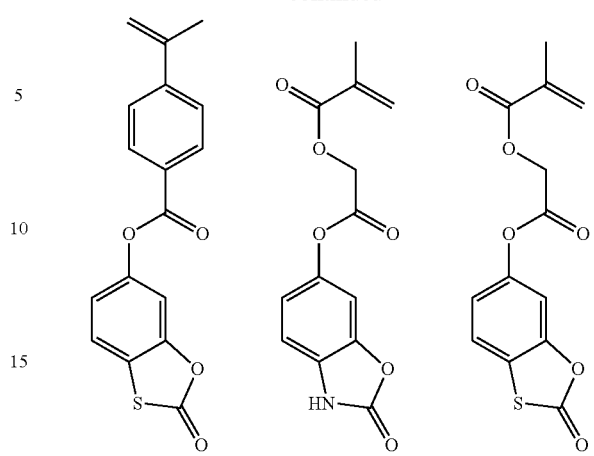
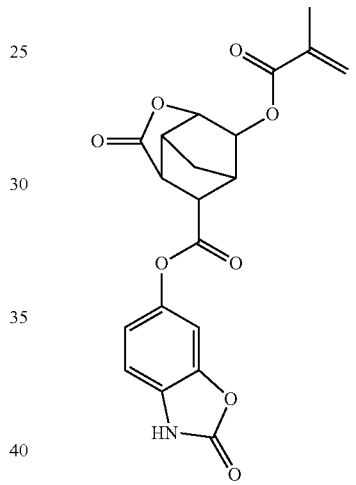
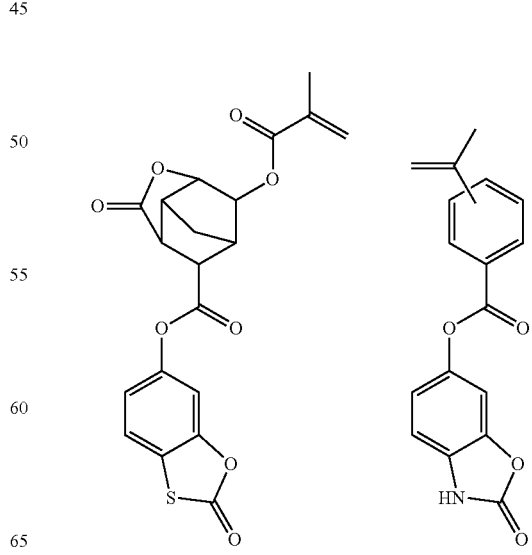

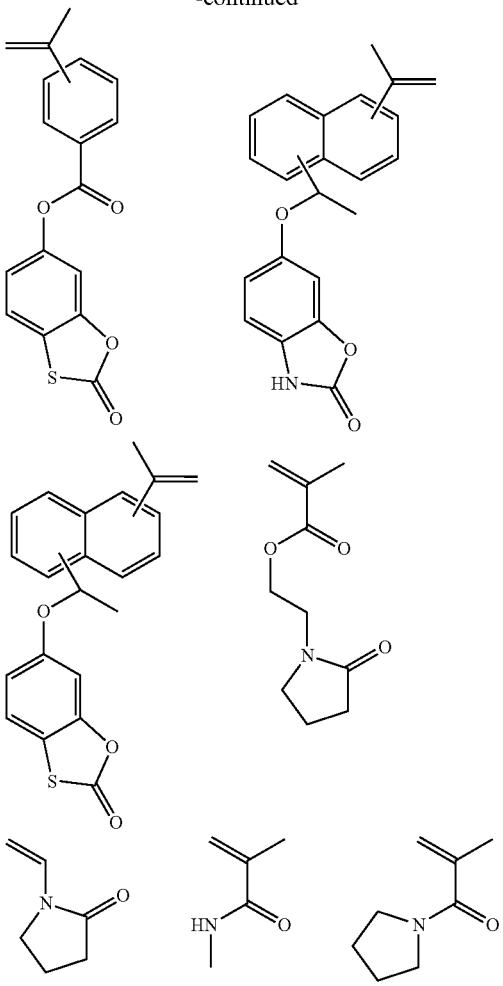

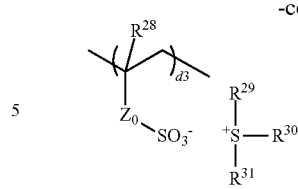

Herein $R^{20}$, $R^{24}$, and $R^{22}$ each are hydrogen or methyl. $R^{21}$ is a single bond, phenylene, —O—R—, or —C(=O)—$Y_0$—R—. $Y_0$ is oxygen or NH. R is a straight, branched or cyclic $C_1$-$C_6$ alkylene group, alkenylene group or phenylene group, which may contain a carbonyl (—CO—), ester (—COO—), ether (—O—), or hydroxyl moiety. $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether moiety, a $C_6$-$C_{12}$ aryl group, a $C_7$-$C_{20}$ aralkyl group, or a thiophenyl group. $Z_0$ is a single bond, methylene, ethylene, phenylene, fluorinated phenylene, —O—$R^{32}$—, or —C(=O)—$Z_1$—$R^{32}$—, wherein $Z_1$ is oxygen or NH, and $R^{32}$ is a straight, branched or cyclic $C_1$-$C_6$ alkylene group, alkenylene group or phenylene group, which may contain a carbonyl, ester, ether or hydroxyl moiety. M⁻ is a non-nucleophilic counter ion. Molar fractions d1, d2 and d3 are in the range: $0 \leq d1 \leq 0.5$, $0 \leq d2 \leq 0.5$, $0 \leq d3 \leq 0.5$, $0 \leq d1+d2+d3 \leq 0.5$. When recurring units (d1), (d2) or (d3) are incorporated, the preferred range is $0 < d1+d2+d3 \leq 0.5$ and $0.2 \leq a+b1+b2+c+d1+d2+d3 \leq 1.0$.

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Other non-nucleophilic counter ions include sulfonates having fluorine substituted at α-position as represented by the general formula (K-1) and sulfonates having fluorine substituted at α- and β-positions as represented by the general formula (K-2).

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In a more preferred embodiment, recurring units (d1), (d2) or (d3) having a sulfonium salt as represented by the following general formula (3) may be copolymerized. It is noted that JP-A 2006-045311 discloses a sulfonium or iodonium salt having polymerizable olefin capable of generating a specific sulfonic acid; and JP-A 2006-178317 discloses a sulfonium salt having sulfonic acid directly attached to the main chain.

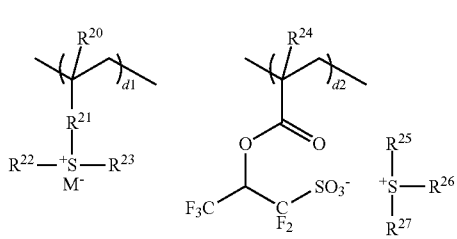

(3)

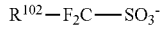 (K-1)

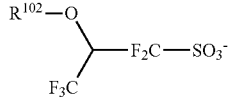 (K-2)

In formula (K-1), $R^{102}$ is hydrogen, or a straight, branched or cyclic $C_1$-$C_{20}$ alkyl group, $C_2$-$C_{20}$ alkenyl group, or $C_6$-$C_{20}$ aryl group, which may have an ether, ester, carbonyl moiety, lactone ring or fluorine. In formula (K-2), $R^{103}$ is hydrogen, or a straight, branched or cyclic $C_1$-$C_{30}$ alkyl or acyl group, $C_2$-$C_{20}$ alkenyl group, or $C_6$-$C_{20}$ aryl or aryloxy group, which may have an ether, ester, carbonyl moiety or lactone ring.

Understandably, when a polymer having copolymerized therein recurring units of any type as represented by formula (3) is used as the base resin in a resist composition, the addition of a photoacid generator to be described later may be omitted.

The polymer may have further copolymerized therein recurring units (e) of any type selected from indene units (e1), acenaphthylene units (e2), chromone units (e3), coumarin units (e4), and norbornadiene units (e5) as represented by the general formula (6).

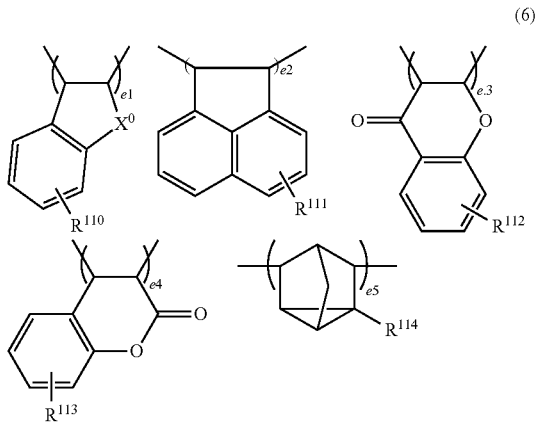

(6)

Herein $R^{110}$ to $R^{114}$ each are hydrogen, $C_1$-$C_{30}$ alkyl, partially or entirely halo-substituted alkyl, hydroxyl, alkoxy, alkanoyl, alkoxycarbonyl, $C_6$-$C_{10}$ aryl, halogen, or 1,1,1,3,3,3-hexafluoro-2-propanol group; $X^0$ is methylene, oxygen or sulfur atom; e1 to e5 are numbers in the range: $0 \leq e1 \leq 0.5$, $0 \leq e2 \leq 0.5$, $0 \leq e3 \leq 0.5$, $0 \leq e4 \leq 0.5$, $0 \leq e5 \leq 0.5$, and $0 < e1+e2+e3+e4+e5 \leq 0.5$.

Besides the recurring units (a) to (e), additional recurring units (f) may be copolymerized in the polymer. Exemplary are recurring units derived from styrene, vinylnaphthalene, vinylanthracene, vinylpyrene, methyleneindane, and the like.

The polymer used herein may be synthesized by any desired methods, for example, by dissolving suitable monomers selected from the monomers to form the recurring units (a) to (f) in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone, and γ-butyrolactone. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

In the copolymer, recurring units (a) to (d) may be incorporated in the following molar fraction: $0<a<1.0$, $0 \leq b1<1.0$, $0 \leq b2<1.0$, $0<b1+b2<1.0$, $0 \leq c \leq 0.9$, $0 \leq d1 \leq 0.5$, $0 \leq d2 \leq 0.5$, $0 \leq d3 \leq 0.5$, $0 \leq d1+d2+d3 \leq 0.5$;
preferably $0.02 \leq a \leq 0.8$, $0 \leq b1 \leq 0.8$, $0 \leq b2 \leq 0.8$, $0.1 \leq b1+b2 \leq 0.8$, $0.1 \leq c \leq 0.85$, $0 \leq d1 \leq 0.4$, $0 \leq d2 \leq 0.4$, $0 \leq d3 \leq 0.4$, $0 \leq d1+d2+d3 \leq 0.4$;
more preferably $0.05 \leq a \leq 0.75$, $0 \leq b1 \leq 0.7$, $0 \leq b2 \leq 0.7$, $0.1 \leq b1+b2 \leq 0.75$, $0.15 \leq c \leq 0.8$, $0 \leq d1 \leq 0.3$, $0 \leq d2 \leq 0.3$, $0 \leq d3 \leq 0.3$, $0 \leq d1+d2+d3 \leq 0.3$; and
even more preferably $0.07 \leq a \leq 0.7$, $0 \leq b1 \leq 0.65$, $0 \leq b2 \leq 0.65$, $0.1 \leq b1+b2 \leq 0.70$, $0.20 \leq c \leq 0.8$, $0 \leq d1 \leq 0.2$, $0 \leq d2 \leq 0.2$, $0 \leq d3 \leq 0.2$, $0 \leq d1+d2+d3 \leq 0.25$.

Also recurring units (e) and (f) may be incorporated in the following molar fraction:
$0 \leq e1 \leq 0.5$, $0 \leq e2 \leq 0.5$, $0 \leq e3 \leq 0.5$, $0 \leq e4 \leq 0.5$, and $0 \leq e5 \leq 0.5$;
preferably $0 \leq e1 \leq 0.4$, $0 \leq e2 \leq 0.4$, $0 \leq e3 \leq 0.4$, $0 \leq e4 \leq 0.4$, and $0 \leq e5 \leq 0.4$;
more preferably $0 \leq e1 \leq 0.3$, $0 \leq e2 \leq 0.3$, $0 \leq e3 \leq 0.3$, $0 \leq e4 \leq 0.3$, and $0 \leq e5 \leq 0.3$; and
$0 \leq f \leq 0.5$, preferably $0 \leq f \leq 0.4$, more preferably $0 \leq f \leq 0.3$. It is preferred that $a+b1+b2+c+d1+d2+d3+e1+e2+e3+e4+e5+f=1$.

The polymer serving as the base resin in the resist composition should have a weight average molecular weight (Mw) in the range of 1,000 to 500,000, and preferably 2,000 to 30,000, as measured by gel permeation chromatography (GPC) versus polystyrene standards using tetrahydrofuran as a solvent. With too low a Mw, the resist composition becomes less heat resistant. A polymer with too high a Mw loses alkaline solubility and gives rise to a footing phenomenon after pattern formation.

If a multi-component polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable as well as a blend of an inventive polymer and a polymer free of recurring units (a).

The polymer is advantageously used as a base resin in a resist composition, typically chemically amplified positive resist composition. Specifically, the polymer is used as a base resin and combined with any desired components including an organic solvent, acid generator, dissolution regulator, basic compound, surfactant, and acetylene alcohol to formulate a resist composition. This resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etching resistance, and minimal proximity bias because of restrained acid diffusion. By virtue of these advantages, the composition is fully useful in commercial application and suited as a pattern-forming material for the fabrication of VLSIs or photomasks.

Particularly when an acid generator is added to formulate a chemically amplified resist composition capable of utilizing acid catalyzed reaction, the composition has a higher sensitivity and is further improved in the properties described above. Typical of the acid generator used herein is a photoacid generator (PAG) capable of generating an acid in response to actinic light or radiation. It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. The acid generators may be used alone or in admixture of two or more. Exemplary acid generators are described in U.S. Pat. No. 7,537,880 (JP-A 2008-111103, paragraphs [0122] to [0142]).

Inclusion of a dissolution regulator may lead to an increased difference in dissolution rate between exposed and unexposed areas and a further improvement in resolution. Addition of a basic compound may be effective in suppressing the diffusion rate of acid in the resist film, achieving a further improvement in resolution. Addition of a surfactant may improve or control the coating characteristics of the resist composition.

Examples of the organic solvent used herein are described in JP-A 2008-111103, paragraphs [0144] to [0145] (U.S. Pat. No. 7,537,880). Exemplary basic compounds are described in JP-A 2008-111103, paragraphs [0146] to [0164]. Exemplary surfactants are described in JP-A 2008-111103, paragraphs [0155] to [0166]. Exemplary dissolution regulators are described in JP-A 2008-122932 (US 2008090172), paragraphs [0155] to [0178], and exemplary acetylene alcohols in paragraphs [0179] to [0182]. Also useful are quenchers of polymer type as described in JP-A 2008-239918. The polymeric quencher segregates at the resist surface after coating and thus enhances the rectangularity of resist pattern. When a protective film is applied, the polymeric quencher is also effective for preventing a film loss of resist pattern or rounding of pattern top.

An appropriate amount of the acid generator used is 0.01 to 100 parts, and preferably 0.1 to 80 parts. An appropriate amount of the organic solvent used is 50 to 10,000 parts, especially 100 to 5,000 parts. The dissolution regulator may be blended in an amount of 0 to 50 parts, preferably 0 to 40 parts, the basic compound in an amount of 0 to 100 parts, preferably 0.001 to 50 parts, and the surfactant in an amount of 0 to 10 parts, preferably 0.0001 to 5 parts. All amounts are expressed in parts by weight relative to 100 parts by weight of the base resin.

Process

The resist composition, typically chemically amplified positive resist composition is used in the fabrication of various integrated circuits. Pattern formation using the resist composition may be performed by well-known lithography processes. The process generally involves coating, heat treatment (or prebaking), exposure, heat treatment (PEB), and development. If necessary, any additional steps may be added.

The resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, or MoSi) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 µm thick.

If desired, a protective film may be formed on the resist film. The protective film is preferably formed of an alkaline developer-soluble composition so that both formation of a resist pattern and stripping of the protective film may be achieved during development. The protective film has the functions of restraining outgassing from the resist film, filtering or cutting off out-of-band (OOB) light having a wavelength of 140 to 300 nm emitted by the EUV laser (other than 13.5 nm), and preventing the resist film from assuming T-top profile or from losing its thickness under environmental impacts.

The resist film is then exposed to a desired pattern of high-energy radiation such as UV, deep-UV, electron beam, x-ray, excimer laser light, γ-ray, synchrotron radiation or EUV (soft x-ray), directly or through a mask. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle or spray techniques. Suitable developers are 0.1 to 10 wt %, preferably 2 to 5 wt % aqueous solutions of tetramethylammonium hydroxide (TMAH), tetraethylammonium hydroxide (TEAH), tetrapropylammonium hydroxide (TPAH) and tetrabutylammonium hydroxide (TBAH). The resist film in the exposed area is dissolved in the developer whereas the resist film in the unexposed area is not dissolved. In this way, the desired positive pattern is formed on the substrate. It is appreciated that the resist composition of the invention is best suited for micro-patterning using such high-energy radiation as KrF excimer laser, ArF excimer laser, EB, EUV (soft x-ray), x-ray, γ-ray and synchrotron radiation among others.

Although TMAH aqueous solution is generally used as the developer, TEAH, TPAH and TBAH having a longer alkyl chain are effective in inhibiting the resist film from being swollen during development and thus preventing pattern collapse. JP 3429592 describes an example using an aqueous TBAH solution for the development of a polymer comprising recurring units having an alicyclic structure such as adamantane methacrylate and recurring units having an acid labile group such as tert-butyl methacrylate, the polymer being water repellent due to the absence of hydrophilic groups.

The TMAH developer is most often used as 2.38 wt % aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 nm or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

In another embodiment, a negative pattern can be formed from the resist composition by organic solvent development. The developer used to this end is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-t-amyl ether, and di-n-hexyl ether. Suitable aromatic solvents include toluene, xylene, ethylbenzene, isopropylbenzene, t-butylbenzene, and mesitylene. The solvents may be used alone or in admixture.

After development, the underlying layer may be processed by dry etching, using the resist pattern as mask. Examples of the underlying layer include an organic antireflective coating, SOG film, Si, $SiO_2$, SiON, SiN, p-Si, α-Si, W, W—Si, Al, Cu, Al—Si, various low dielectric films, etch stop films, and stepped substrates for Fin-FET. The underlying layer is typically formed to a thickness of 2 to 10,000 nm, especially 3 to 5,000 nm. Ion implantation using the resist pattern as mask is also possible. Since the methacrylate-based resist according to the invention does not undergo crosslinking upon ion implantation, it may be readily stripped off after ion implantation. Furthermore, the resist having copolymerized therein methacrylate units having a substituted phenol group according to the invention is suppressed in film thickness loss of pattern after development as compared with the resist having copolymerized therein methacrylate units having an unsubstituted phenol group. The resist pattern is thus fully amenable to ion implantation.

EXAMPLE

Synthesis Examples, Comparative Synthesis Examples, Examples and Comparative Examples are given below for further illustrating the invention, but they should not be construed as limiting the invention thereto. Mw is a weight average molecular weight as measured by gel permeation chromatography (GPC) versus polystyrene standards using tetrahydrofuran as a solvent, and Mw/Mn designates molecular weight distribution or dispersity. All parts (pbw) are by weight.

Monomer Synthesis Example 1

Monomer 1: 3-hydroxy-2-methylphenyl methacrylate

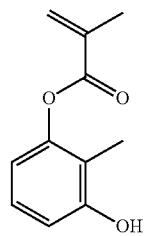

In 200 g of 1,4-dioxane were dissolved 100 g of 2-methylresorcinol and 43 g of methacrylic anhydride. Methanesulfonic acid, 0.52 g, was added dropwise to the solution, which was further stirred at 60° C. for 24 hours. Once the reaction solution was cooled down, 105 g of 15 wt % sodium hydroxide aqueous solution was added dropwise to quench the reaction. Toluene, 500 g, was added to the solution, followed by standard aqueous workup. The solvent was distilled off, and the resulting crude product was dissolved in 40 g of toluene again. The solution was added dropwise to 1,000 g of hexane, whereupon crystals precipitated out. The crystals were collected by filtration and dried, obtaining 44 g (yield 85%) of Monomer 1.

The target compound was analyzed by infrared absorption spectroscopy (IR) and proton nuclear magnetic resonance spectroscopy ($^1$H-NMR), with the results shown below.

IR (D-ATR): ν=3361, 1699, 1628, 1615, 1595, 1505, 1469, 1404, 1379, 1329, 1284, 1229, 1176, 1157, 1062, 1000, 962, 950, 916, 863, 815, 782, 721, 706, 644, 622 cm$^{-1}$ $^1$H-NMR (600 MHz in DMSO-d$_6$):

δ=1.89 (3H, s), 2.00 (3H, s), 5.87 (1H, m), 6.27 (1H, m), 6.52 (1H, d), 6.72 (1H, d), 7.01 (1H, t), 9.62 (1H, s) ppm Monomer Synthesis Example 2

Monomer 2: 3-hydroxy-5-methylphenyl methacrylate

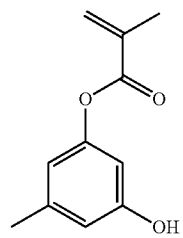

Monomer 2 was synthesized as in Monomer Synthesis Example 1 aside from using 5-methylresorcinol instead of 2-methylresorcinol. Yield 80%.

Additionally, Monomers 3 to 11 were similarly synthesized.
Monomers 1 to 11, Adhesive Monomers 1 and 2, and PAG Monomers 1 to 6 used in the following Synthesis Examples are identified below. The mixing ratio (e.g., 50:50) indicated below is a molar ratio.
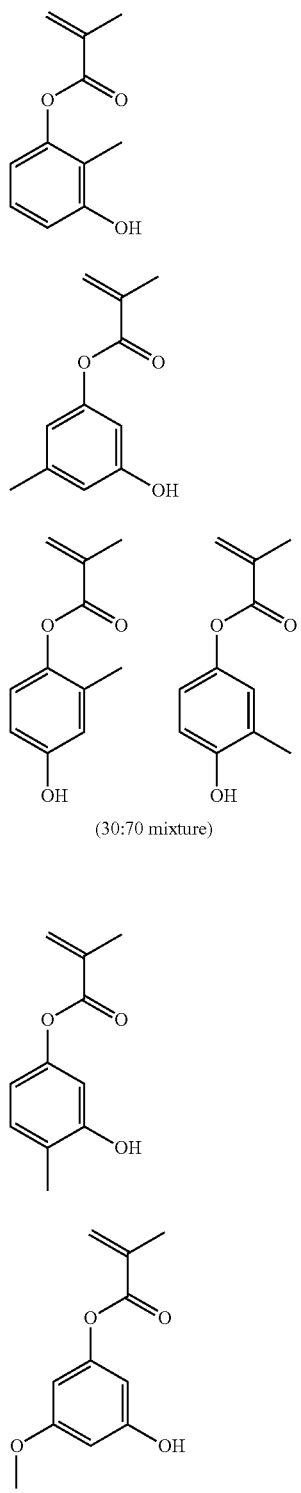
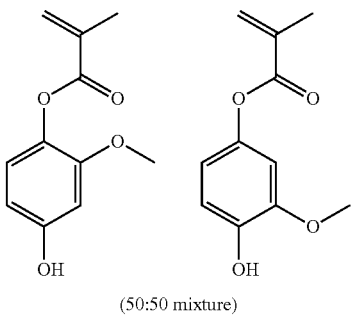

-continued

Monomer 11

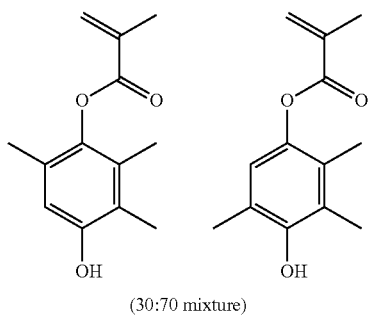

(30:70 mixture)

Monomer 1: 3-hydroxy-2-methylphenyl methacrylate
Monomer 2: 3-hydroxy-5-methylphenyl methacrylate
Monomer 3: a 30:70 mixture of
    4-hydroxy-2-methylphenyl methacrylate and
    4-hydroxy-3-methylphenyl methacrylate
Monomer 4: 3-hydroxy-4-methylphenyl methacrylate
Monomer 5: 3-hydroxy-5-methoxyphenyl methacrylate
Monomer 6: a 50:50 mixture of
    4-hydroxy-2-methoxyphenyl methacrylate and
    4-hydroxy-3-methoxyphenyl methacrylate
Monomer 7: 3-hydroxy-5-ethylphenyl methacrylate
Monomer 8: 3-hydroxy-5-ethoxyphenyl methacrylate
Monomer 9: 4-hydroxy-2,3-dimethylphenyl methacrylate
Monomer 10: 4-hydroxy-3,5-dimethylphenyl methacrylate
Monomer 11: a 30:70 mixture of
    4-hydroxy-2,3,6-trimethylphenyl methacrylate and
    4-hydroxy-2,3,5-trimethylphenyl methacrylate Adhesive Monomer 1

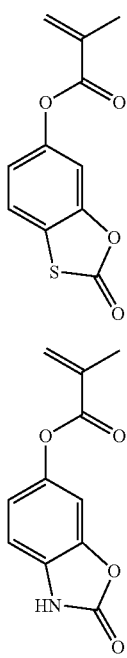

Adhesive Monomer 1: 2-oxo-1,3-benzoxathiol-5-yl methacrylate
Adhesive Monomer 2: 2-oxo-2,3-dihydrobenzoxazol-5-yl methacrylate PAG Monomer 1

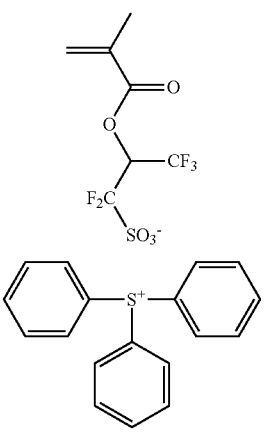

PAG Monomer 2

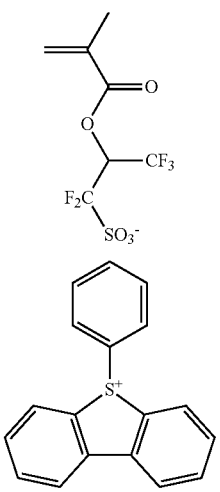

PAG Monomer 3

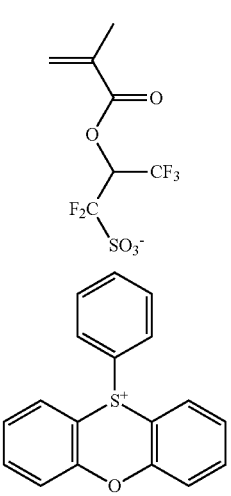

PAG Monomer 4

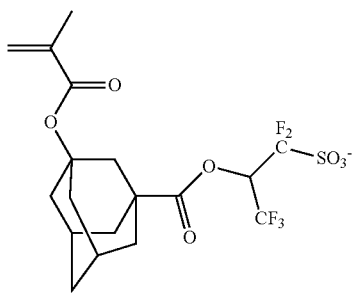

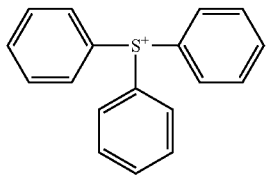

PAG Monomer 5

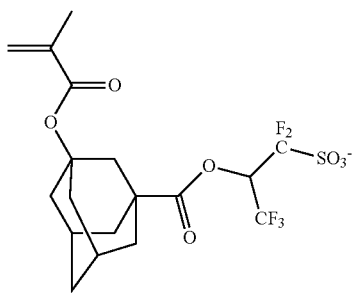

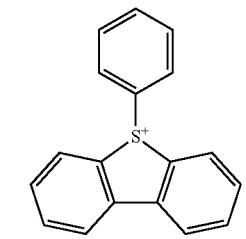

PAG Monomer 6

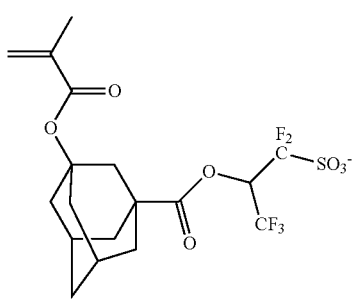

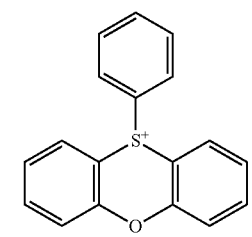

PAG Monomer 1: triphenylsulfonium 1,1,3,3,3-pentafluoro-2-(methacryloyloxy)propane-1-sulfonate PAG Monomer 2: 5-phenyldibenzothiophenium 1,1,3,3,3-penta-fluoro-2-(methacryloyloxy)propane-1-sulfonate PAG Monomer 3: 10-phenylphenoxathiinium 1,1,3,3,3-penta-fluoro-2-(methacryloyloxy)propane-1-sulfonate PAG Monomer 4: triphenylsulfonium 1,1,3,3,3-pentafluoro-2-(3-methacryloyloxy-adamantane-1-carbonyloxy)-propane-1-sulfonate PAG Monomer 5: 5-phenyldibenzothiophenium 1,1,3,3,3-penta-fluoro-2-(3-methacryloyloxy-adamantane-1-carbonyloxy)propane-1-sulfonate PAG Monomer 6: 10-phenylphenoxathiinium 1,1,3,3,3-penta-fluoro-2-(3-methacryloyloxy-adamantane-1-carbonyloxy)propane-1-sulfonate Synthesis Example 1

A 2-L flask was charged with 8.2 g of 3-ethyl-3-exo-tetracyclo[4.4.0.1$^{2,5}$.1$^{7,10}$]dodecanyl methacrylate, 13.4 g of Monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of azobisisobutyronitrile (AIBN) was added as a polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.

Copolymer Composition (Molar Ratio)
3-ethyl-3-exo-tetracyclo[4.4.0.1$^{2,5}$.1$^{7,10}$]dodecanyl methacrylate:Monomer 1=0.30:0.70
Mw=11,700
Mw/Mn=2.01
This is designated Polymer 1.

Polymer 1

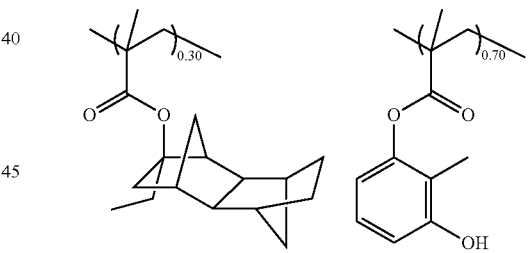

Synthesis Example 2

A 2-L flask was charged with 6.3 g of 3-ethyl-3-exo-tetracyclo[4.4.0.1$^{2,5}$.1$^{7,10}$]dodecanyl methacrylate, 5.8 g of Monomer 2, 1.7 g of indene, 6.0 g of 4-acetoxystyrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 2:indene:4-hydroxystyrene=0.23:0.30: 0.10:0.37

Mw=8,400

Mw/Mn=1.74

This is designated Polymer 2.

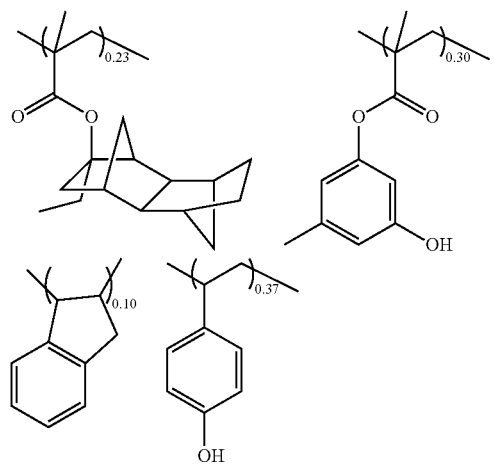

Polymer 2

Synthesis Example 3

A 2-L flask was charged with 6.2 g of 2-ethyl-2-adamantyl methacrylate, 5.8 g of Monomer 3, 1.7 g of acenaphthylene, 6.0 g of 4-acetoxystyrene, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dissolved again in a mixture of 100 mL of methanol and 200 mL of tetrahydrofuran, to which 10 g of triethylamine and 10 g of water were added. Deprotection reaction of acetyl group was conducted at 70° C. for 5 hours, followed by neutralization with acetic acid. The reaction solution was concentrated and dissolved in 100 mL of acetone. By similar precipitation, filtration, and drying at 60° C., a white polymer was obtained.

The polymer was analyzed by $^{13}$C-NMR, $^{1}$H-NMR, and GPC, with the analytical data shown below.

Copolymer Composition (Molar Ratio)

2-ethyl-2-adamantyl methacrylate:Monomer 3:acenaphthylene:4-hydroxystyrene=0.25:0.30:0.10:0.35

Mw=9,400

Mw/Mn=1.86

This is designated Polymer 3.

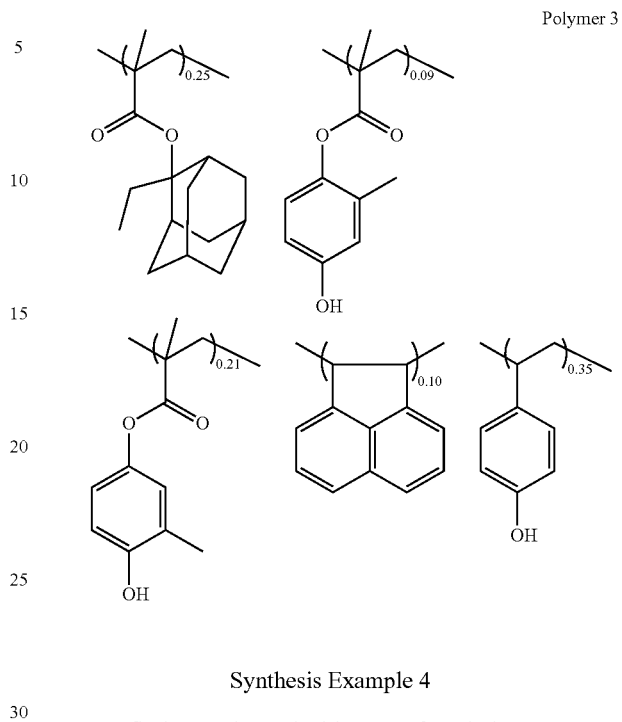

Polymer 3

Synthesis Example 4

A 2-L flask was charged with 8.2 g of 3-ethyl-3-exo-tetracyclo[4.4.0.1$^{2,5}$.1$^{7,10}$]dodecanyl methacrylate, 3.8 g of Monomer 4, 11.1 g of 5-oxo-4-oxatricyclo[4.2.1.0$^{3,7}$]-nonan-2-yl methacrylate, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 4:5-oxo-4-oxatricyclo[4.2.1.0$^{3,7}$]-nonan-2-yl methacrylate=0.30:0.20:0.50

Mw=7,600

Mw/Mn=1.81

This is designated Polymer 4.

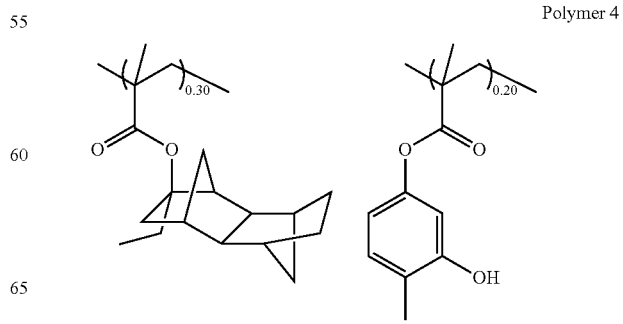

Polymer 4

-continued

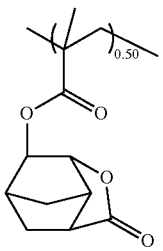

Synthesis Example 5

A 2-L flask was charged with 8.2 g of 3-ethyl-3-exo-tetracyclo[4.4.0.1$^{2,5}$.1$^{7,10}$]dodecanyl methacrylate, 5.8 g of Monomer 2, 7.1 g of Adhesive Monomer 1, 5.6 g of PAG Monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.
Copolymer Composition (Molar Ratio)
3-ethyl-3-exo-tetracyclo[4.4.0.1$^{2,5}$.1$^{7,10}$]dodecanyl methacrylate:Monomer 2:Adhesive Monomer 1:PAG Monomer 1=0.30:0.30:0.30:0.10
Mw=7,200
Mw/Mn=1.72
This is designated Polymer 5.

Polymer 5

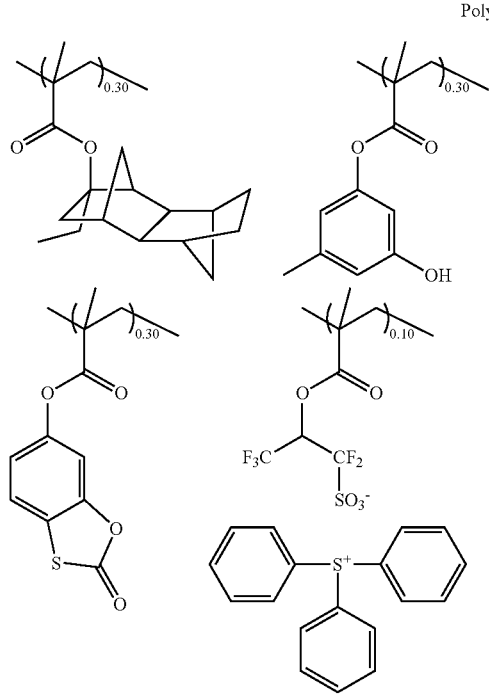

Synthesis Example 6

A 2-L flask was charged with 8.2 g of 3-ethyl-3-exo-tetracyclo[4.4.0.1$^{2,5}$.1$^{7,10}$]dodecanyl methacrylate, 9.7 g of Monomer 8, 4.4 g of Adhesive Monomer 2, 5.6 g of PAG Monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.
Copolymer Composition (Molar Ratio)
3-Ethyl-3-Exo-Tetracyclo[4.4.0.1$^{2,5}$.1$^{7,10}$]Dodecanyl methacrylate:Monomer 8:Adhesive Monomer 2:PAG Monomer 1=0.30:0.40:0.20:0.10
Mw=7,000
Mw/Mn=1.70
This is designated Polymer 6.

Polymer 6

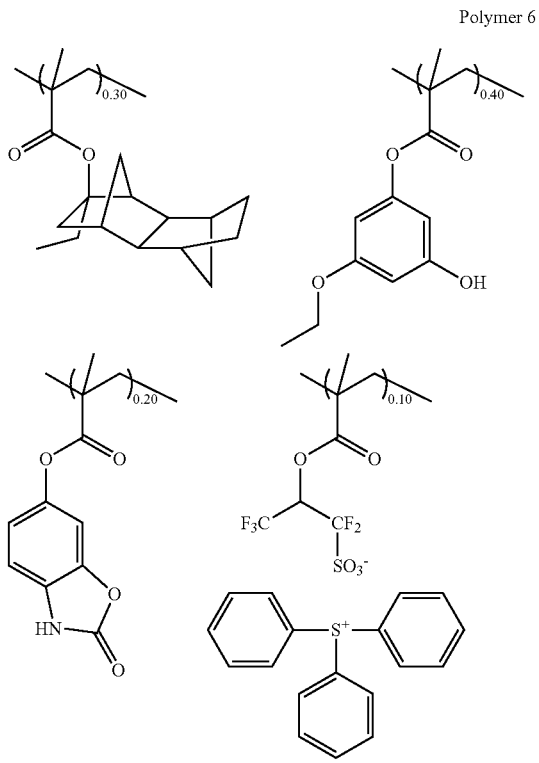

Synthesis Example 7

A 2-L flask was charged with 5.5 g of 3-ethyl-3-exo-tetracyclo[4.4.0.1$^{2,5}$.1$^{7,10}$]dodecanyl methacrylate, 3.5 g of 4-tert-butoxyphenyl methacrylate, 5.8 g of Monomer 2, 5.5 g of 3-oxo-2,7-dioxatricyclo[4.2.1.0$^{4,8}$]nonan-9-yl methacrylate, 5.6 g of PAG Monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.
Copolymer Composition (Molar Ratio)
3-ethyl-3-exo-tetracyclo[4.4.0.1$^{2,5}$.1$^{7,10}$]dodecanyl methacrylate:4-tert-butoxyphenyl methacrylate:Monomer 2:3-oxo-2,7-dioxatricyclo[4.2.1.0$^{4,8}$]nonan-9-yl methacrylate:PAG Monomer 1=0.20:0.15:0.30:0.25:0.10
Mw=7,800
Mw/Mn=1.77
This is designated Polymer 7.

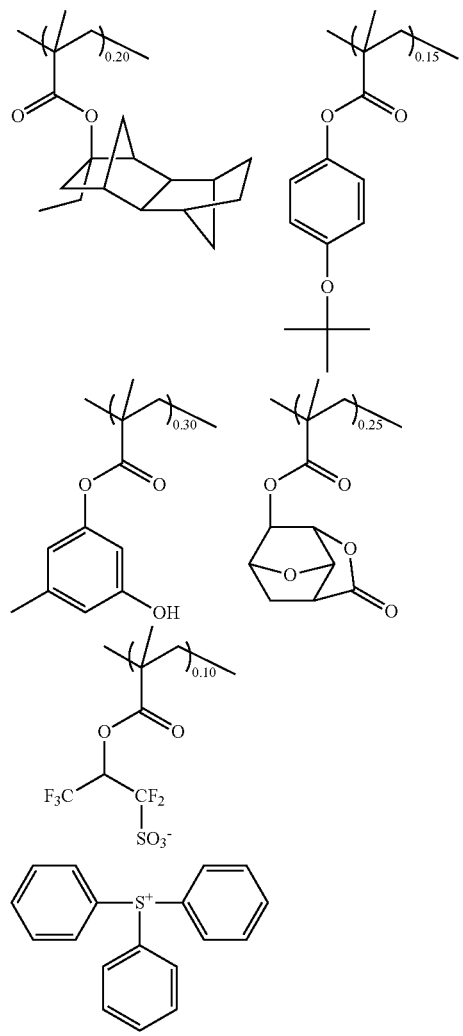

Polymer 7

Synthesis Example 8

A 2-L flask was charged with 5.5 g of 3-ethyl-3-exo-tetracyclo[4.4.0.1$^{2,5}$.1$^{7,10}$]dodecanyl methacrylate, 2.9 g of tert-amyloxystyrene, 6.7 g of Monomer 1, 4.4 g of 3-oxo-2,7-dioxatricyclo[4.2.1.0$^{4,8}$]nonan-9-yl methacrylate, 5.6 g of PAG Monomer 2, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.
Copolymer Composition (Molar Ratio)
3-ethyl-3-exo-tetracyclo[4.4.0.1$^{2,5}$.1$^{7,10}$]dodecanyl methacrylate:tert-amyloxystyrene:Monomer 1:3-oxo-2,7-dioxatricyclo[4.2.1.0$^{4,8}$]nonan-9-yl methacrylate:PAG Monomer 2=0.20:0.15:0.35:0.20:0.10
Mw=9,100
Mw/Mn=1.91
This is designated Polymer 8.

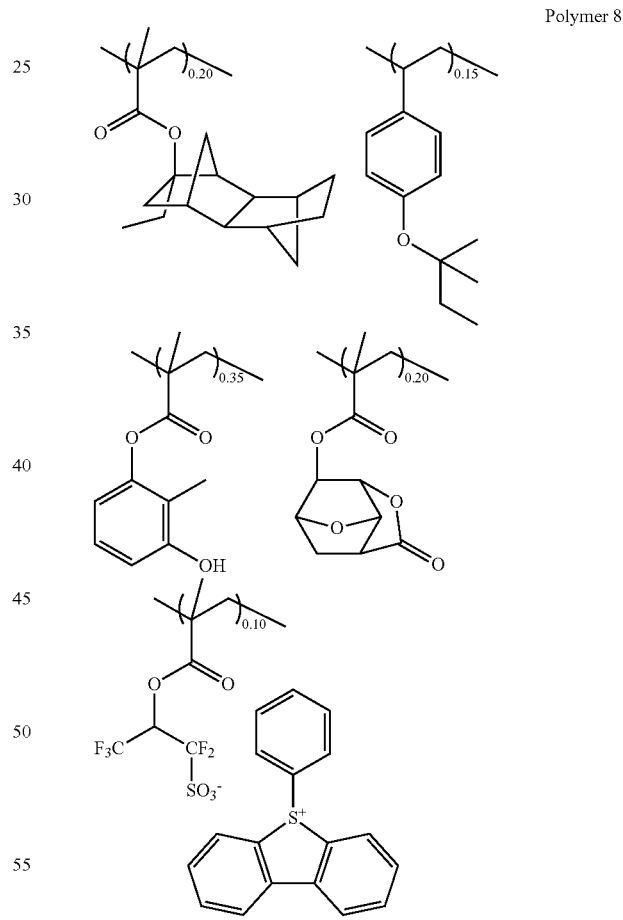

Polymer 8

Synthesis Example 9

A 2-L flask was charged with 5.5 g of 3-ethyl-3-exo-tetracyclo[4.4.0.1$^{2,5}$.1$^{7,10}$]dodecanyl methacrylate, 3.6 g of 6-tert-butoxy-2-vinylnaphthalene, 7.3 g of Monomer 5, 4.4 g of 3-oxo-2,7-dioxatricyclo[4.2.1.0$^{4,8}$]nonan-9-yl methacrylate, 5.7 g of PAG Monomer 3, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.
Copolymer Composition (Molar Ratio)
3-ethyl-3-exo-tetracyclo[4.4.0.1$^{2,5}$.1$^{7,10}$]dodecanyl methacrylate:6-tert-butoxy-2-vinylnaphthalene:Monomer 5:3-oxo-2,7-dioxatricyclo[4.2.1.0$^{4,8}$]nonan-9-yl methacrylate: PAG Monomer 3=0.20:0.15:0.35:0.20:0.10
Mw=9,500
Mw/Mn=1.91
This is designated Polymer 9.

drofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.
Copolymer Composition (Molar Ratio)
6,7,8,9-tetrahydro-5H-benzocyclohepten-5-yl methacrylate:Monomer 4:3-oxo-2,7-dioxatricyclo[4.2.1.0$^{4,8}$]nonan-9-yl methacrylate:PAG Monomer 1=0.30:0.30:0.30:0.10
Mw=9,300
Mw/Mn=1.83
This is designated Polymer 10.

Polymer 9

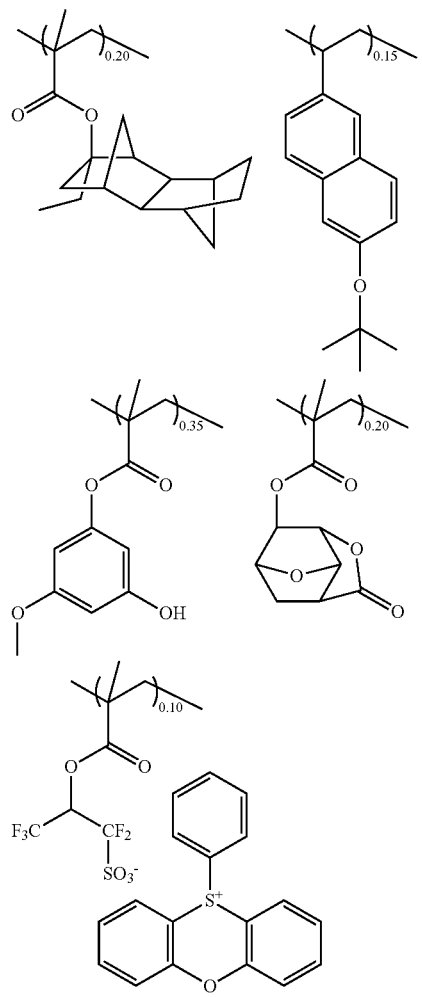

Polymer 10

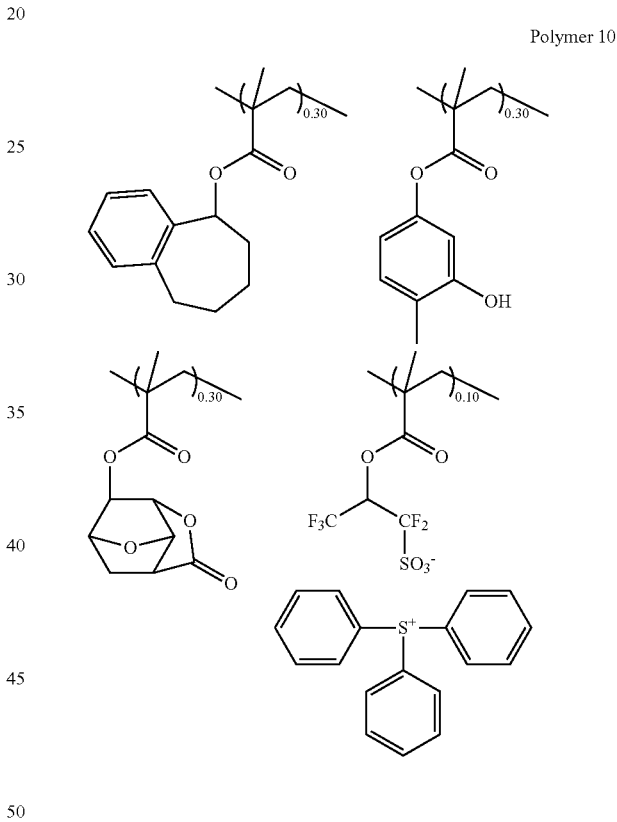

Synthesis Example 10

A 2-L flask was charged with 6.9 g of 6,7,8,9-tetrahydro-5H-benzocyclohepten-5-yl methacrylate, 5.8 g of Monomer 4, 6.6 g of 3-oxo-2,7-dioxatricyclo[4.2.1.0$^{4,8}$]-nonan-9-yl methacrylate, 5.6 g of PAG Monomer 1, and 40 g of tetrahy- Synthesis Example 11

A 2-L flask was charged with 5.2 g of 1-(adamantan-1-yl)-1-methylethyl methacrylate, 2.9 g of tert-amyloxystyrene, 6.2 g of Monomer 5, 4.5 g of 3-oxo-2,7-dioxatricyclo [4.2.1.0$^{4,8}$]nonan-9-yl methacrylate, 11.0 g of PAG Monomer 4, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.

Copolymer Composition (Molar Ratio)

1-(adamantan-1-yl)-1-methylethyl methacrylate:tert-amyloxystyrene:Monomer 5:3-oxo-2,7-dioxatricyclo-[4.2.1.0$^{4,8}$]nonan-9-yl methacrylate:PAG Monomer 4=0.20:0.15:0.30:0.20:0.15

Mw=9,100

Mw/Mn=1.84

This is designated Polymer 11.

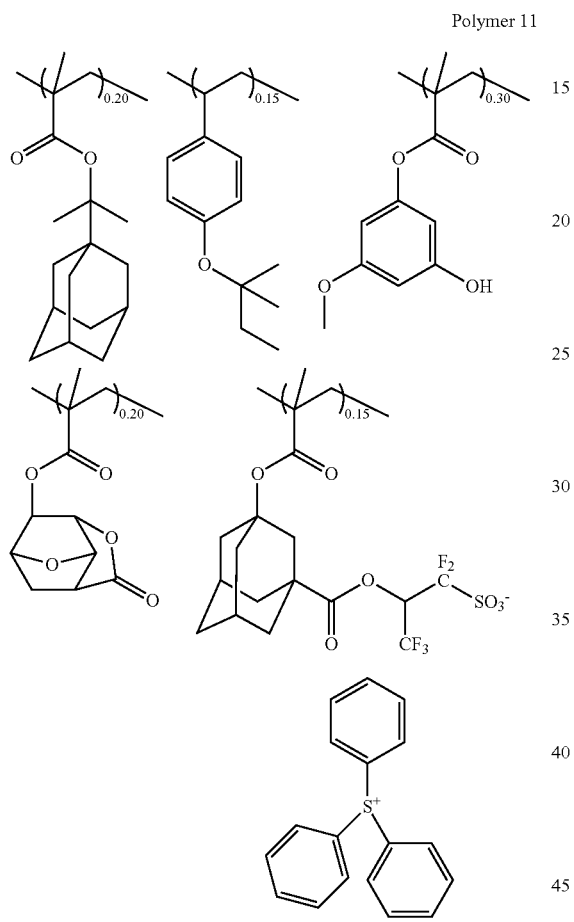

Polymer 11

Synthesis Example 12

A 2-L flask was charged with 5.2 g of 1-(adamantan-1-yl)-1-methylethyl methacrylate, 2.9 g of tert-amyloxystyrene, 6.2 g of Monomer 6, 4.5 g of 3-oxo-2,7-dioxatricyclo [4.2.1.04,8]nonan-9-yl methacrylate, 11.0 g of PAG Monomer 5, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.

Copolymer Composition (Molar Ratio)

1-(adamantan-1-yl)-1-methylethyl methacrylate:tert-amyloxystyrene:Monomer 6:3-oxo-2,7-dioxatricyclo-[4.2.1.0$^{4,8}$]nonan-9-yl methacrylate:PAG Monomer 5=0.20:0.15:0.30:0.20:0.15

Mw=9,200

Mw/Mn=1.78

This is designated Polymer 12.

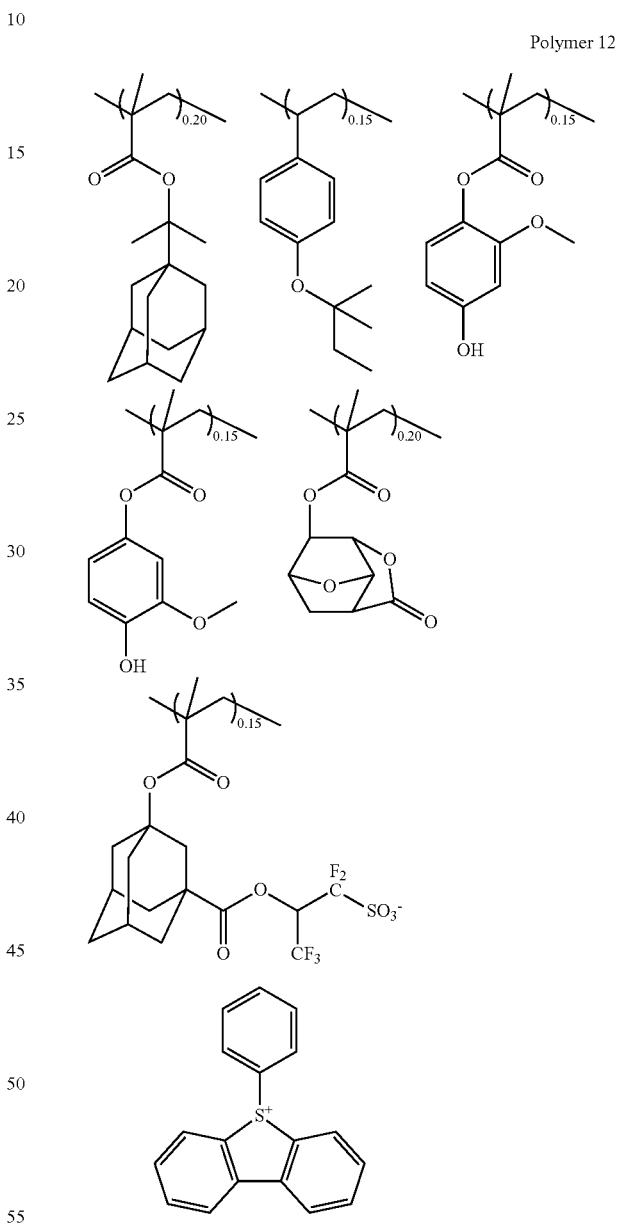

Polymer 12

Synthesis Example 13

A 2-L flask was charged with 5.2 g of 1-(adamantan-1-yl)-1-methylethyl methacrylate, 2.9 g of tert-amyloxystyrene, 6.1 g of Monomer 7, 3.4 g of 2-oxooxolan-3-yl methacrylate, 11.0 g of PAG Monomer 6, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.

Copolymer Composition (Molar Ratio)

1-(adamantan-1-yl)-1-methylethyl methacrylate:tert-amyloxystyrene:Monomer 7:2-oxooxolan-3-yl methacrylate:PAG Monomer 6=0.20:0.15:0.30:0.20:0.15

Mw=8,800

Mw/Mn=1.88

This is designated Polymer 13.

The polymer was analyzed by $^{13}$C-NMR, $^{1}$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 2:3-oxo-2,7-dioxatricyclo-[4.2.1.0$^{4,8}$]nonan-9-yl methacrylate:PAG Monomer 1=0.30:0.30:0.30:0.10

Mw=7,500

Mw/Mn=1.75

This is designated Polymer 14.

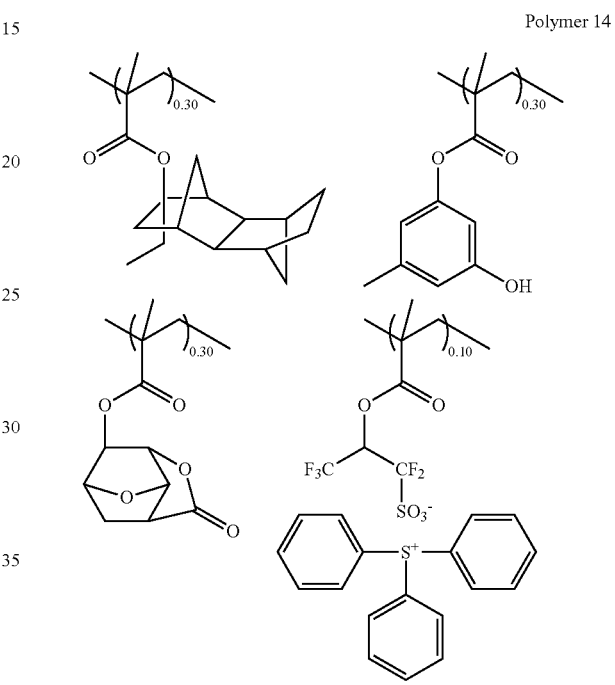

Polymer 14

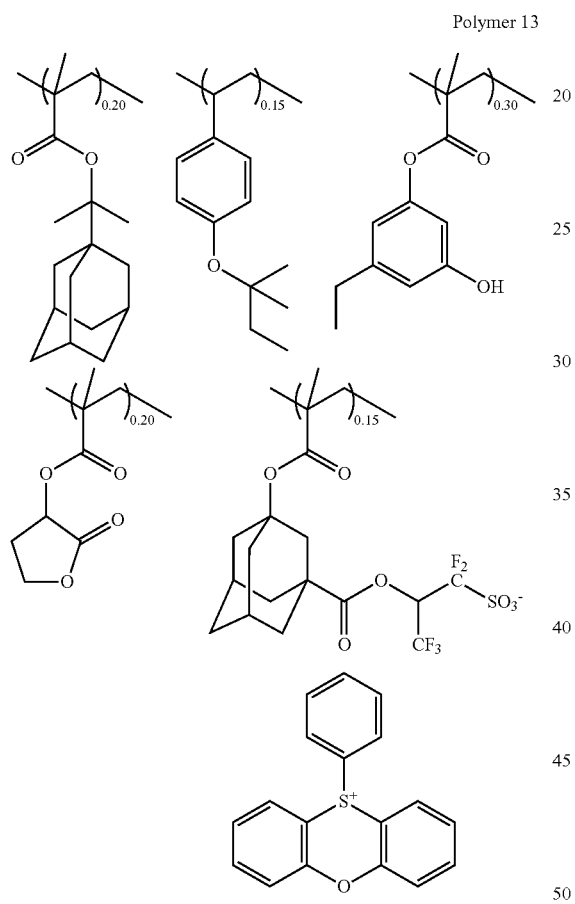

Polymer 13

Synthesis Example 14

A 2-L flask was charged with 8.2 g of 3-ethyl-3-exo-tetracyclo[4.4.0.1$^{2,5}$.1$^{7,10}$]dodecanyl methacrylate, 5.8 g of Monomer 2, 6.7 g of 3-oxo-2,7-dioxatricyclo-[4.2.1.0$^{4,8}$]nonan-9-yl methacrylate, 5.6 g of PAG Monomer 1, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

Synthesis Example 15

A 2-L flask was charged with 8.2 g of 3-ethyl-3-exo-tetracyclo[4.4.0.1$^{2,5}$.1$^{7,10}$]dodecanyl methacrylate, 4.1 g of Monomer 9, 6.0 g of 2-oxooxolan-3-yl methacrylate, 11.0 g of PAG Monomer 5, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^{1}$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 9:2-oxooxolan-3-yl methacrylate:PAG Monomer 5=0.30:0.20:0.35:0.15

Mw=8,800

Mw/Mn=1.71

151

This is designated Polymer 15.

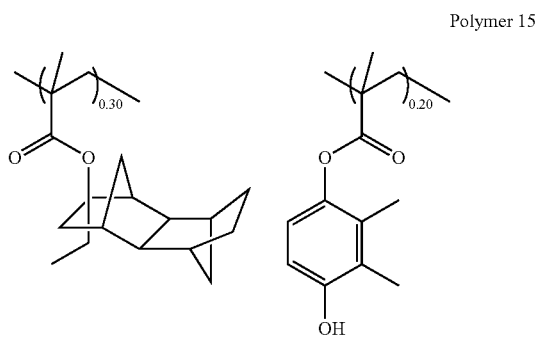

Polymer 15

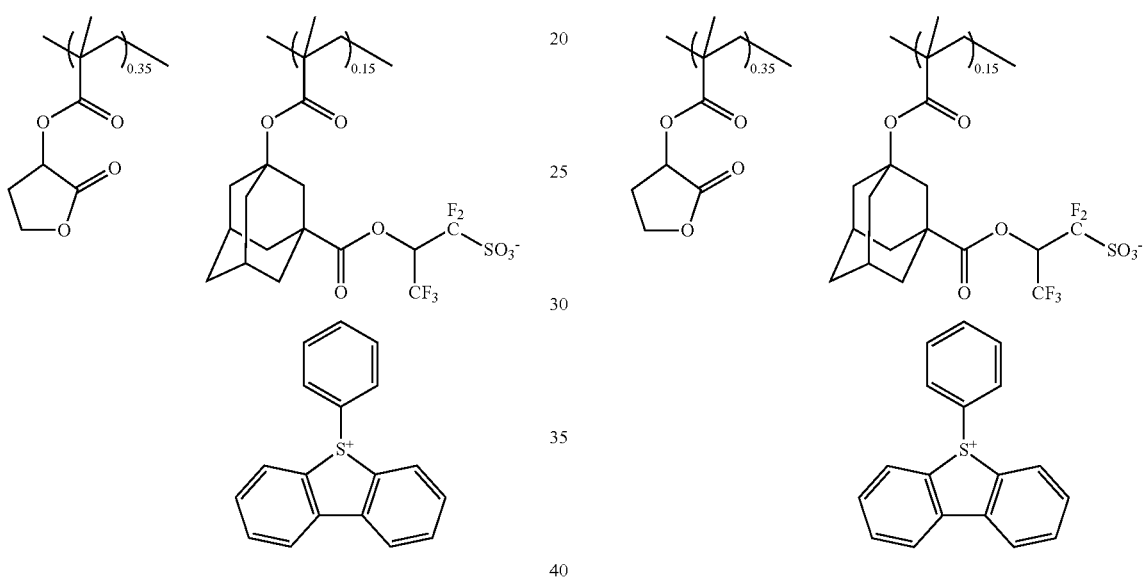

Synthesis Example 16

A 2-L flask was charged with 8.2 g of 3-ethyl-3-exo-tetracyclo[4.4.0.1$^{2,5}$.1$^{7,10}$]dodecanyl methacrylate, 4.1 g of Monomer 10, 6.0 g of 2-oxooxolan-3-yl methacrylate, 11.0 g of PAG Monomer 5, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 10:2-oxooxolan-3-yl methacrylate:PAG Monomer 5=0.30:0.20:0.35:0.15

Mw=8,300

Mw/Mn=1.73

152

This is designated Polymer 16.

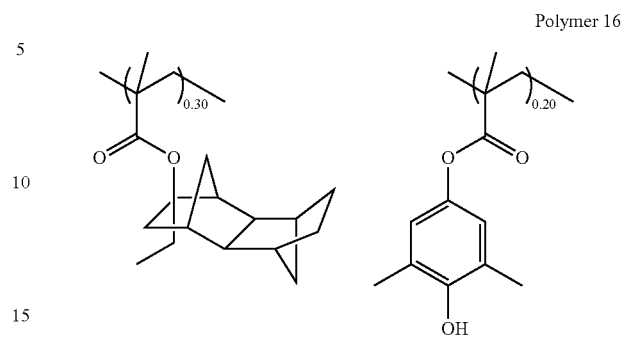

Polymer 16

Synthesis Example 17

A 2-L flask was charged with 8.2 g of 3-ethyl-3-exo-tetracyclo[4.4.0.1$^{2,5}$.1$^{7,10}$]dodecanyl methacrylate, 4.4 g of Monomer 11, 6.0 g of tetrahydro-2-oxofuran-3-yl methacrylate, 11.0 g of PAG Monomer 5, and 40 g of tetrahydrofuran as solvent. The reactor was cooled to −70° C. in a nitrogen atmosphere, whereupon vacuum evacuation and nitrogen blow were repeated three times. The reactor warmed up to room temperature whereupon 1.2 g of AIBN was added as polymerization initiator. The reactor was heated at 60° C. and reaction run for 15 hours. The reaction solution was precipitated from 1 L of isopropyl alcohol. The white solid was collected by filtration and dried in vacuum at 60° C., yielding a white polymer.

The polymer was analyzed by $^{13}$C-NMR, $^1$H-NMR, and GPC, with the analytical data shown below.

Copolymer Composition (Molar Ratio)

3-ethyl-3-exo-tetracyclo[4.4.0.1$^{2,5}$.1$^{7,10}$]dodecanyl methacrylate:Monomer 11:tetrahydro-2-oxofuran-3-yl methacrylate:PAG Monomer 5=0.30:0.20:0.35:0.15

Mw=8,900

Mw/Mn=1.78

This is designated Polymer 17.

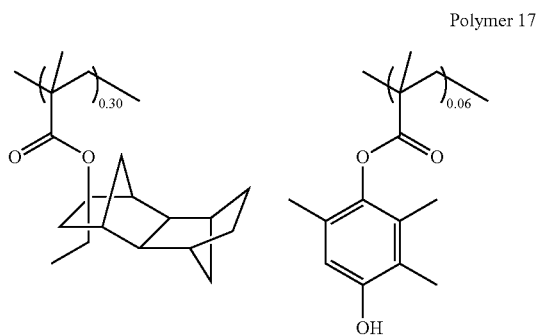
Polymer 17

This is designated Comparative Polymer 1.

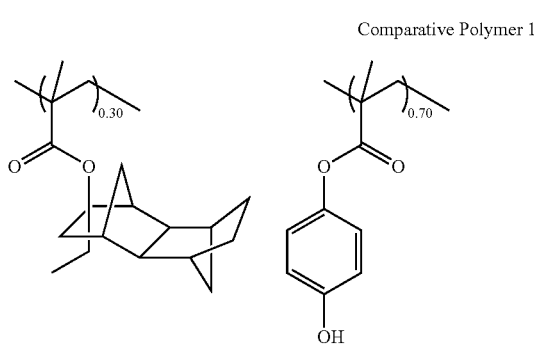
Comparative Polymer 1

Comparative Synthesis Example 2

A polymer was synthesized by the same procedure as above.

Copolymer Composition (Molar Ratio)

3-ethyl-3-exo-tetracyclo[4.4.0.1$^{2,5}$.1$^{7,10}$]dodecanyl methacrylate:4-methoxy-3-hydroxystyrene=0.30:0.70

Mw=9,700

Mw/Mn=1.79

This is designated Comparative Polymer 2.

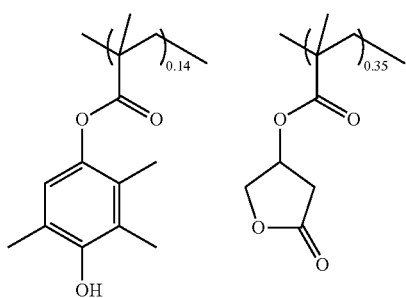

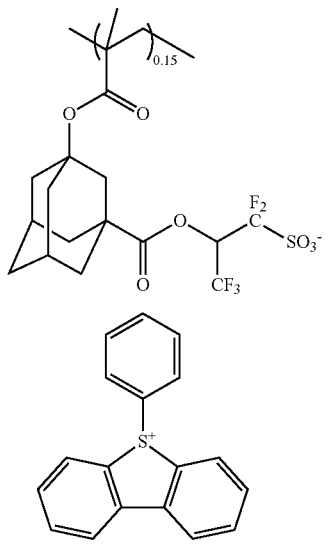

Comparative Polymer 2

Comparative Synthesis Example 1

A polymer was synthesized by the same procedure as above.

Copolymer Composition (Molar Ratio)

3-ethyl-3-exo-tetracyclo[4.4.0.1$^{2,5}$.1$^{7,10}$]dodecanyl methacrylate:4-hydroxyphenyl methacrylate=0.30:0.70

Mw=9,900

Mw/Mn=1.99

Comparative Synthesis Example 3

A polymer was synthesized by the same procedure as above.

Copolymer Composition (Molar Ratio)

3-ethyl-3-exo-tetracyclo[4.4.0.1$^{2,5}$.1$^{7,10}$]dodecanyl methacrylate:4-hydroxy-3,5-dimethylbenzyl methacrylamide=0.30:0.70

Mw=9,300

Mw/Mn=1.72

This is designated Comparative Polymer 3.

Comparative Polymer 3

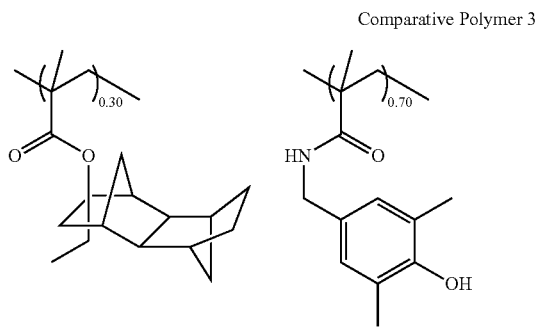

Comparative Synthesis Example 4

A polymer was synthesized by the same procedure as above.
Copolymer Composition (Molar Ratio)
3-ethyl-3-exo-tetracyclo[4.4.0.1$^{2,5}$.1$^{7,10}$]dodecanyl methacrylate:4-hydroxyphenyl methacrylate:3-oxo-2,7-dioxatricyclo[4.2.1.0$^{4,8}$]nonan-9-yl methacrylate:PAG Monomer 1=0.30:0.20:0.40:0.10
Mw=7,300
Mw/Mn=1.88
This is designated Comparative Polymer 4.

Comparative Polymer 4

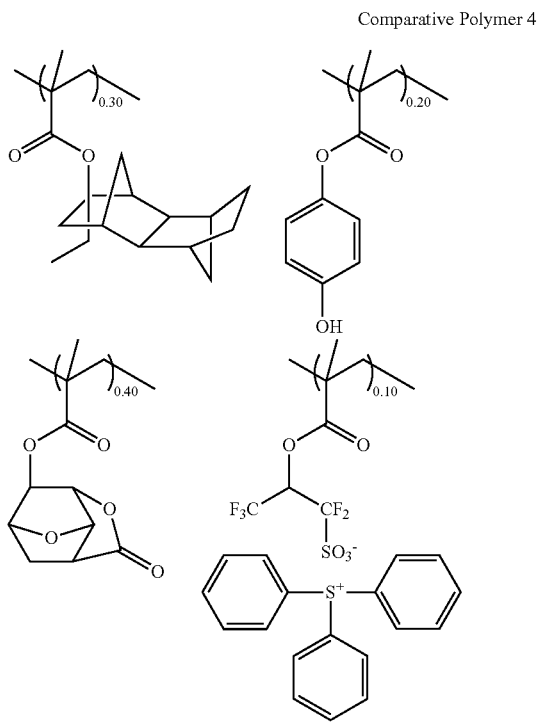

Examples and Comparative Examples

Positive resist compositions were prepared by dissolving each of the polymers synthesized above and selected components in a solvent in accordance with the recipe shown in Tables 1 and 2, and filtering through a filter having a pore size of 0.2 μm. The solvent contained 100 ppm of a surfactant FC-4430 (3M Sumitomo Co., Ltd.).

The components in Tables 1 and 2 are as identified below.
Polymers 1 to 17: polymers synthesized in Synthesis Examples 1 to 17
Comparative Polymers 1 to 4:
  polymers synthesized in Comparative Synthesis Examples 1 to 4
Organic solvents: propylene glycol monomethyl ether acetate (PGMEA)
  propylene glycol monomethyl ether (PGME)
  cyclohexanone (CyH)
  cyclopentanone (CyP)
Acid generators: PAG1 and PAG2 of the structural formulae shown below

PAG1

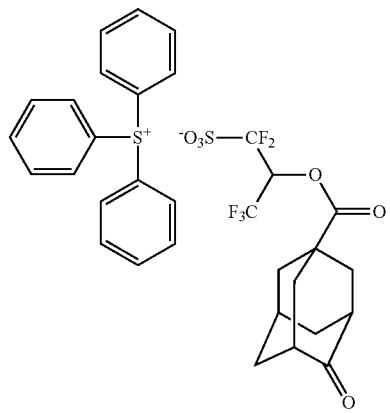

PAG2

Basic compound: Amine 1 of the structural formula shown below

Amine 1

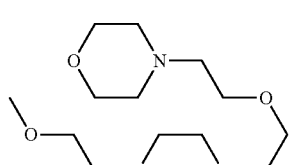

EB Writing Test

Using a coater/developer system Clean Track Mark 5 (Tokyo Electron Ltd.), the positive resist composition was spin coated onto a silicon substrate (diameter 6 inches, vapor primed with hexamethyldisilazane (HMDS)) and pre-baked on a hot plate at 110° C. for 60 seconds to form a resist film of 100 nm thick. Using a system HL-800D (Hitachi Ltd.) at a HV voltage of 50 kV, the resist film was exposed imagewise to EB in a vacuum chamber.

Using Clean Track Mark 5, immediately after the imagewise exposure, the wafer was baked (PEB) on a hot plate at the temperature shown in Tables 1 and 2 for 60 seconds and puddle developed in a 2.38 wt % TMAH aqueous solution for 30 seconds to form a positive pattern.

Resolution is a minimum size at the exposure dose (sensitivity) that provides a 1:1 resolution of a 100-nm line-and-space pattern. The 100-nm line-and-space pattern was measured for line width roughness (LWR) under SEM.

The resist composition is shown in Tables 1 and 2 together with the sensitivity, resolution, and LWR of EB lithography.

TABLE 1

| | | Polymer (pbw) | Acid generator (pbw) | Basic compound (pbw) | Organic solvent (pbw) | PEB temperature (°C.) | Sensitivity ($\mu C/cm^2$) | Resolution (nm) | LWR (nm) |
|---|---|---|---|---|---|---|---|---|---|
| Example | 1-1 | Polymer 1 (100) | PAG 1 (20) | Amine 1 (1.0) | PGMEA (1,500) CyH (200) | 90 | 25.6 | 75 | 6.5 |
| | 1-2 | Polymer 2 (1003) | PAG 1 (20) | Amine 1 (1.0) | PGMEA (1,500) CyH (200) | 95 | 24.4 | 75 | 6.9 |
| | 1-3 | Polymer 3 (100) | PAG 1 (20) | Amine 1 (1.0) | PGMEA (1,500) CyH (200) | 95 | 26.3 | 75 | 6.8 |
| | 1-4 | Polymer 4 (100) | PAG 1 (20) | Amine 1 (1.0) | PGMEA (1,500) CyH (200) | 90 | 26.0 | 75 | 6.2 |
| | 1-5 | Polymer 5 (100) | — | Amine 1 (0.8) | PGMEA (500) CyH (1,450) PGME (50) | 95 | 21.3 | 70 | 4.5 |
| | 1-6 | Polymer 6 (100) | — | Amine 1 (0.8) | PGMEA (500) CyH (1,450) PGME (50) | 95 | 22.1 | 70 | 4.8 |
| | 1-7 | Polymer 7 (100) | — | Amine 1 (0.8) | PGMEA (500) CyH (1,450) PGME (50) | 90 | 22.3 | 70 | 4.4 |
| | 1-8 | Polymer 8 (100) | — | Amine 1 (0.8) | PGMEA (500) CyH (1,450) PGME (50) | 90 | 23.2 | 70 | 4.1 |
| | 1-9 | Polymer 9 (100) | — | Amine 1 (0.8) | PGMEA (500) CyH (1,450) PGME (50) | 95 | 22.3 | 70 | 4.8 |
| | 1-10 | Polymer 10 (100) | — | Amine 1 (0.8) | PGMEA (500) CyH (1,450) PGME (50) | 90 | 24.1 | 70 | 4.3 |
| | 1-11 | Polymer 11 (100) | — | Amine 1 (0.8) | PGMEA (300) CyH (1,450) CyP (250) | 95 | 22.3 | 70 | 4.6 |
| | 1-12 | Polymer 12 (100) | — | Amine 1 (0.8) | PGMEA (300) CyH (1,450) CyP (250) | 95 | 22.6 | 70 | 4.1 |
| | 1-13 | Polymer 13 (100) | — | Amine 1 (0.8) | PGMEA (300) CyH (1,450) CyP (250) | 95 | 23.9 | 70 | 3.8 |
| | 1-14 | Polymer 14 (100) | — | Amine 1 (0.9) | PGMEA (500) CyH (1,450) PGME (50) | 90 | 23.9 | 70 | 4.1 |
| | 1-15 | Polymer 15 (100) | — | Amine 1 (0.8) | PGMEA (300) CyH (1,450) CyP (250) | 85 | 28.6 | 70 | 3.1 |
| | 1-16 | Polymer 16 (100) | — | Amine 1 (0.8) | PGMEA (300) CyH (1,450) CyP (250) | 85 | 28.9 | 70 | 3.2 |
| | 1-17 | Polymer 17 (100) | — | Amine 1 (0.9) | PGMEA (500) CyH (1,450) PGME (50) | 85 | 29.9 | 70 | 3.3 |

TABLE 2

| | | Polymer (pbw) | Acid generator (pbw) | Basic compound (pbw) | Organic solvent (pbw) | PEB temperature (°C.) | Sensitivity ($\mu C/cm^2$) | Resolution (nm) | LWR (nm) |
|---|---|---|---|---|---|---|---|---|---|
| Comparative Example | 1-1 | Comparative Polymer 1 (100) | PAG 1 (12) | Amine 1 (1.0) | PGMEA (1,500) CyH (200) | 90 | 23.5 | 90 | 8.9 |
| | 1-2 | Comparative Polymer 2 (100) | PAG 1 (12) | Amine 1 (1.0) | PGMEA (1,500) CyH (200) | 90 | 30.5 | 90 | 8.8 |

TABLE 2-continued

|  |  | Polymer (pbw) | Acid generator (pbw) | Basic compound (pbw) | Organic solvent (pbw) | PEB temperature (° C.) | Sensitivity (µC/cm$^2$) | Resolution (nm) | LWR (nm) |
|---|---|---|---|---|---|---|---|---|---|
|  | 1-3 | Comparative Polymer 3 (100) | PAG 1 (12) | Amine 1 (1.0) | PGMEA (1,500) CyH (200) | 95 | 33.5 | 90 | 8.8 |
|  | 1-4 | Comparative Polymer 4 (100) | — | Amine 1 (0.8) | PGMEA (500) CyH (1,450) PGME (50) | 90 | 32.0 | 75 | 6.1 |

EUV Exposure Test

A positive resist composition was prepared by dissolving each of the polymers synthesized above and selected components in a solvent in accordance with the recipe shown in Table 3, and filtering through a filter having a pore size of 0.2 µm. The resist composition was spin coated on a silicon substrate (diameter 4 inches, HMDS vapor primed) and prebaked on a hot plate at 105° C. for 60 seconds to form a resist film of 40 nm thick. EUV exposure was performed by dipole illumination at NA 0.3.

Immediately after the exposure, the wafer was baked (PEB) on a hot plate at the temperature shown in Table 3 for 60 seconds and puddle developed with a 2.38 wt % TMAH aqueous solution for 30 seconds to form a positive pattern.

Resolution is a minimum size at the exposure dose (sensitivity) that provides a 1:1 resolution of a 30-nm line-and-space pattern. The 35-nm line-and-space pattern was measured for LWR under SEM.

The resist composition is shown in Table 3 together with the sensitivity, resolution, and LWR of EUV lithography.

TABLE 3

|  | Polymer (pbw) | Acid generator (pbw) | Basic compound (pbw) | Organic solvent (pbw) | PEB temperature (° C.) | Sensitivity (mJ/cm$^2$) | Resolution (nm) | LWR (nm) |
|---|---|---|---|---|---|---|---|---|
| Example 2-1 | Polymer 14 (100) | — | Amine 1 (0.8) | PGMEA (1,000) CyH (2,000) PGME (500) | 90 | 9 | 22 | 4.0 |
| Comparative Example 2-1 | Comparative Polymer 4 (100) | — | Amine 1 (0.8) | PGMEA (1,000) CyH (2,000) PGME (500) | 90 | 12 | 26 | 5.1 |

KrF Exposure Test

A resist composition was formulated according to Table 4 and coated on an antireflective coating (DUV-42 by Nissan Chemical Industries, Ltd., 61 nm thick) on a 8-inch wafer to form a resist film of 200 nm thick. Using a KrF scanner S203B (Nikon Corp., NA 0.68, σ 0.75, ⅔ annular illumination, 6% halftone phase shift mask), the resist film was exposed, baked (PEB) at the temperature shown in Table 4, and developed in 2.38 wt % TMAH aqueous solution for 30 seconds, yielding a positive 130 nm line-and-space pattern. The wafer was sectioned, and the profile of the L/S pattern was observed under SEM.

The resist composition is shown in Table 4 together with the sensitivity and profile of KrF lithography.

TABLE 4

|  | Polymer (pbw) | Acid generator (pbw) | Basic compound (pbw) | Organic solvent (pbw) | PEB temperature (° C.) | Sensitivity (mJ/cm$^2$) | Profile |
|---|---|---|---|---|---|---|---|
| Example 3-1 | Polymer 1 (100) | PAG 2 (6) | Amine 1 (1.0) | PGMEA (800) CyH (200) | 90 | 30 | rectangular pattern |
| Comparative Example 3-1 | Comparative Polymer 1 (100) | PAG 2 (6) | Amine 1 (1.0) | PGMEA (800) CyH (200) | 90 | 28 | pattern of reduced film thickness |

It is evident from Tables 1 to 4 that the resist compositions using the inventive polymers having copolymerized therein a hydroxyphenyl methacrylate having one alkyl or alkoxy group substituted thereon meet satisfactory resolution, sensitivity and edge roughness and are effective for suppressing a pattern film thickness loss. By further copolymerizing an acid generator therein, more improvements in resolution and edge roughness are attained.

Japanese Patent Application No. 2012-112272 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising as a base resin a polymer comprising recurring units having a carboxyl and/or phenolic hydroxyl group substituted with an acid labile group, recurring units having the general formula (1):

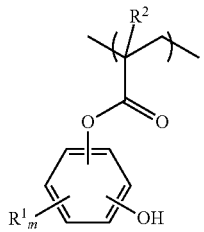
(1)

wherein $R^1$ is methyl, ethyl, propyl, methoxy, ethoxy or propoxy, $R^2$ is hydrogen or methyl, and m is an integer of 1 to 4, and recurring units selected from the following formulae (d2-1) and (d2-2):

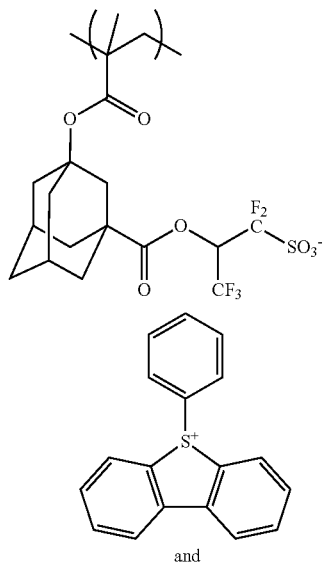
(d2-1)

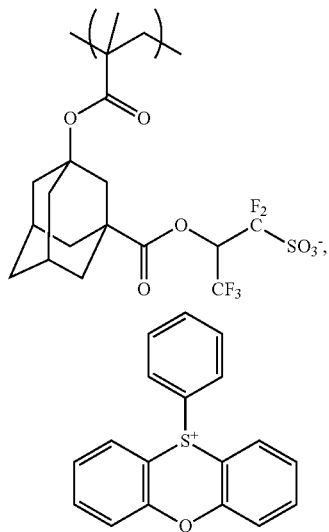
(d2-2)

the polymer having a weight average molecular weight of 1,000 to 500,000.

2. The resist composition of claim 1 wherein the recurring units having a carboxyl and/or phenolic hydroxyl group substituted with an acid labile group are acid labile group-substituted recurring units (b1) and/or (b2):

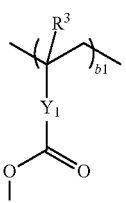
(b1)

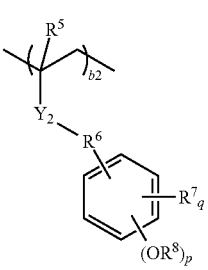
(b2)

wherein $R^3$ and $R^5$ each are hydrogen or methyl, $R^4$ and $R^8$ each are an acid labile group, $R^6$ is a single bond or a straight or branched $C_1$-$C_6$ alkylene group, $R^7$ is hydrogen, fluorine, trifluoromethyl, cyano, or straight, branched or cyclic $C_1$-$C_6$ alkyl group, p is 1 or 2, q is an integer of 0 to 4, $Y_1$ is a single bond, a divalent $C_1$-$C_{12}$ linking group having an ester radical, ether radical or lactone ring, phenylene group or naphthylene group, and $Y_2$ is a single bond, —C(=O)—O— or —C(=O)—NH.

3. The resist composition of claim 2 wherein in addition to the recurring units (a) and acid labile group-substituted recurring units (b1) and/or (b2), as represented by the general formula (2), the polymer further comprises recurring units (c) having an adhesive group selected from the class consisting of hydroxyl (exclusive of hydroxyl in formula (1)), carboxyl, lactone ring, carbonate, thiocarbonate, carbonyl, cyclic acetal, ether, ester, sulfonic acid ester, cyano, amide, and —O—C(=O)-G- wherein G is sulfur or NH and c is a number in the range: 0<c≤0.9 and 0.2≤a+b1+b2+c≤1.0.

4. The resist composition of claim 1, further comprising an organic solvent and an acid generator, the composition being a chemically amplified resist composition.

5. The resist composition of claim 4, further comprising a basic compound and/or a surfactant as an additive.

6. A pattern forming process comprising the steps of applying the resist composition of claim 1 onto a substrate to form a coating, baking, exposing the coating to high-energy radiation, and developing the exposed coating in a developer.

7. The process of claim 6 wherein the high-energy radiation is KrF excimer laser, ArF excimer laser, electron beam or soft X-ray having a wavelength of 3 to 15 nm.

8. A polymer comprising recurring units (a') of at least one type selected from units (a1) to (a8), acid labile group-containing recurring units (b1) and/or (b2), and recurring units selected from formulae (d2-1) and (d2-2) as copolymerized:

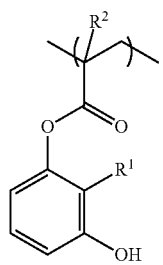
(a1)

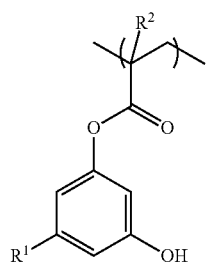
(a2)

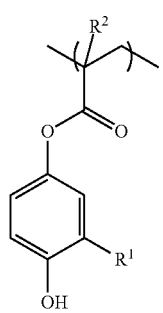
(a3)

-continued

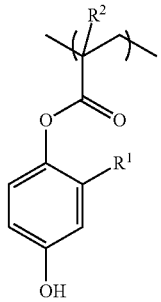
(a4)

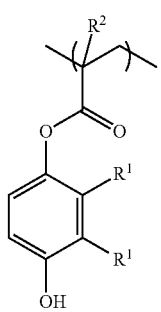
(a5)

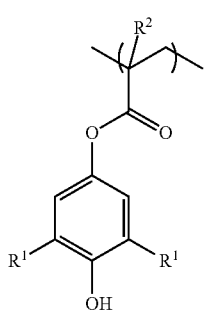
(a6)

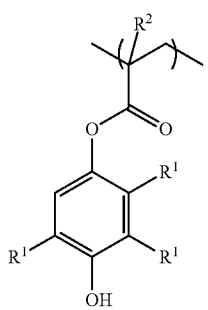
(a7)

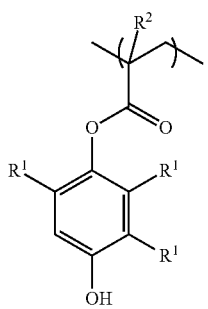
(a8)

(b1)

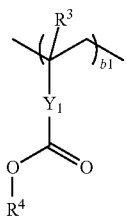

(b2)

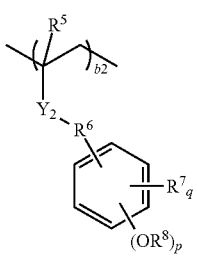

wherein R¹ is methyl, ethyl, propyl, methoxy, ethoxy or propoxy, R² is hydrogen or methyl, R³ and R⁵ each are hydrogen or methyl, R⁴ and R⁸ each are an acid labile group, R⁶ is a single bond or a straight or branched $C_1$-$C_6$ alkylene group, R⁷ is hydrogen, fluorine, trifluoromethyl, cyano, or straight, branched or cyclic $C_1$-$C_6$ alkyl group, p is 1 or 2, q is an integer of 0 to 4, $Y_1$ is a single bond, a divalent $C_1$-$C_{12}$ linking group having an ester radical, ether radical or lactone ring, phenylene group or naphthylene group, $Y_2$ is a single bond, —C(=O)—O— or —C(=O)—NH—, a', b1 and b2 are numbers in the range: 0<a'<1.0, 0≤b<1<1.0, 0≤b2<1.0, 0<b1+b2<1.0, and 0.1≤a'+b1+b2≤1.0, the polymer having a weight average molecular weight of 1,000 to 500,000, (d2-1)

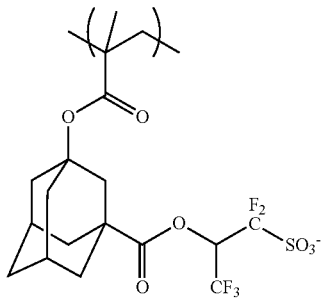

and (d2-2)

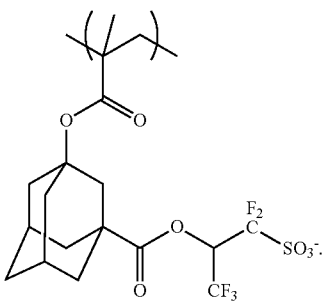

* * * * *